US011071823B2

(12) United States Patent
    Cassim

(10) Patent No.: US 11,071,823 B2
(45) Date of Patent: Jul. 27, 2021

(54) WEARABLE BAND FOR AUTOMATIC INJECTION OF MEDICINE

(71) Applicant: Medicabiome Inc., Toronto (CA)

(72) Inventor: Zachary Cassim, Toronto (CA)

(73) Assignee: Medicabiome Inc., Toronto (CA)

( * ) Notice: Subject to any disclaimer, the term of this patent is extended or adjusted under 35 U.S.C. 154(b) by 172 days.

(21) Appl. No.: 16/234,536

(22) Filed: Dec. 27, 2018

(65) Prior Publication Data

US 2020/0206422 A1 Jul. 2, 2020

(51) Int. Cl.
    *A61M 5/20* (2006.01)
    *G06N 20/00* (2019.01)
    *G16H 50/20* (2018.01)

(52) U.S. Cl.
    CPC ........ *A61M 5/2033* (2013.01); *A61M 5/2046* (2013.01); *G06N 20/00* (2019.01); *G16H 50/20* (2018.01); *A61M 2205/0288* (2013.01); *A61M 2205/18* (2013.01); *A61M 2205/3303* (2013.01); *A61M 2205/3313* (2013.01); *A61M 2205/3337* (2013.01); *A61M 2205/3553* (2013.01);
    (Continued)

(58) Field of Classification Search
    CPC .............. A61M 5/2033; A61M 5/2046; A61M 2205/3553; A61M 2209/088; A61M 2230/06; A61M 2230/50; A61M 2205/3313; A61M 2230/30; A61M 2205/3303; A61M 2205/0288; A61M 2205/3337; A61M 2205/50; A61M 2205/3584; A61M 2205/581; A61M 2205/18; A61M 2205/502; A61M 2205/8206; A61M 5/20; A61M 5/31565; A61M 5/31576; A61M 5/3158; A61M 5/31581; A61M 5/31583; A61M 5/31586; A61M 2005/14252; A61M 2005/206; A61M 2025/0206; A61M 2025/0213; A61M 2025/0253; A61M 2025/0126; A61M 25/02; G06N 20/00; G16H 50/20; A44C 5/0023
    See application file for complete search history.

(56) References Cited

U.S. PATENT DOCUMENTS 5,860,957 A  1/1999 Jacobsen et al.
6,824,529 B2 11/2004 Gross et al.
(Continued)

*Primary Examiner* — Theodore J Stigell
*Assistant Examiner* — Rachel T. Smith
(74) *Attorney, Agent, or Firm* — Ridout & Maybee LLP

(57) ABSTRACT

A system for automatically injecting a substance. The system includes an injecting device, which includes an injecting cartridge, a biasing mechanism and a latch. The injecting cartridge includes a syringe having a needle and a plunger, and an injecting mechanism for moving the syringe and pushing the plunger of the syringe. The injecting cartridge includes a needle and a plunger, and an injecting mechanism for moving the syringe and pushing the plunger of the syringe. The biasing mechanism pivots the injecting cartridge from a storage position into an injecting position. The latch is moveable from a holding position for holding the biasing mechanism in the storage position to a release position for releasing the biasing mechanism. The system may further comprise sensors to measuring physical signs of a user. The system may also include controller to control the automatic injection of the substance.

49 Claims, 47 Drawing Sheets

(52) U.S. Cl.
CPC . *A61M 2205/3584* (2013.01); *A61M 2205/50* (2013.01); *A61M 2205/502* (2013.01); *A61M 2205/581* (2013.01); *A61M 2205/8206* (2013.01); *A61M 2209/088* (2013.01); *A61M 2230/06* (2013.01); *A61M 2230/30* (2013.01); *A61M 2230/50* (2013.01)

(56) References Cited

U.S. PATENT DOCUMENTS

| | | |
|---|---|---|
| 9,061,097 B2 | 6/2015 | Holt et al. |
| 9,072,827 B2 | 7/2015 | Cabiri |
| 9,180,244 B2 | 11/2015 | Anderson et al. |
| 9,463,280 B2 | 10/2016 | Cabiri |
| 9,636,457 B2 * | 5/2017 | Newberry ............ A61M 5/3298 |
| 10,646,643 B2 * | 5/2020 | Cabiri ............... A61M 5/14248 |
| 2014/0296782 A1 | 10/2014 | Ulrich et al. |
| 2016/0074062 A1 | 3/2016 | Krupnick et al. |
| 2016/0256106 A1 | 9/2016 | Krasnow et al. |
| 2016/0363479 A1 * | 12/2016 | Dumont ................ G01J 1/0403 |
| 2017/0172522 A1 * | 6/2017 | Insler ................. A61B 5/14551 |
| 2017/0239418 A1 * | 8/2017 | Levine .................. A61K 31/137 |
| 2017/0246390 A1 * | 8/2017 | Tchao ................... A61K 38/28 |
| 2018/0000206 A1 * | 1/2018 | Nakamura ............ A44C 5/0023 |
| 2018/0140236 A1 | 5/2018 | Brister et al. |
| 2020/0138377 A1 * | 5/2020 | Huijbregts ............ A61B 5/4266 |

* cited by examiner

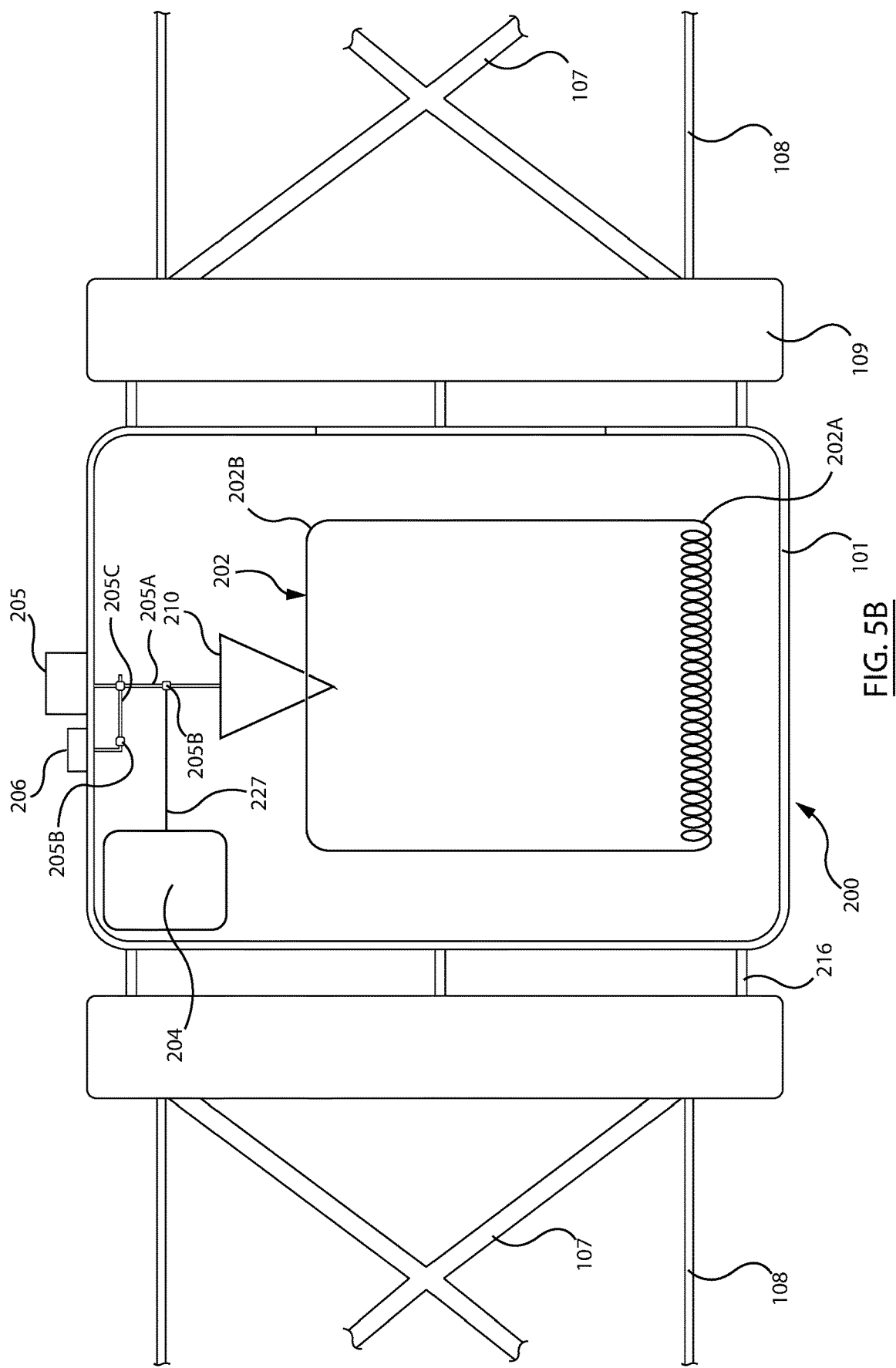

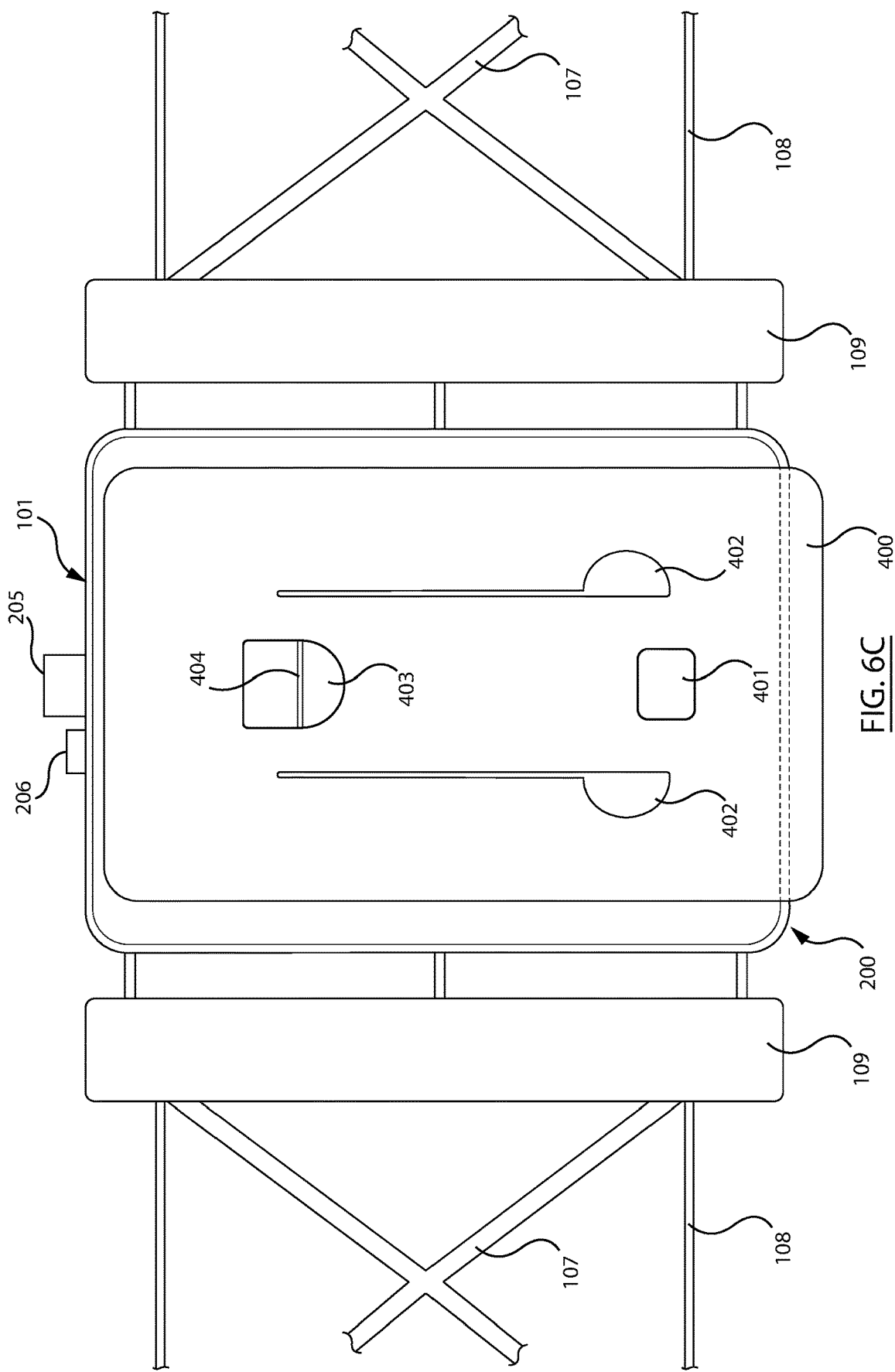

LCD Display

Battery

O², IR, HR Sensors

WEARABLE BAND FOR AUTOMATIC INJECTION OF MEDICINE

TECHNICAL FIELD

Example embodiments relate to a system for injecting medicine, in particular, injecting medicine in emergency situations, for example, acute allergic reactions.

BACKGROUND

Products have been developed that allow medicines to be injected to users in emergency situations, for example, acute allergic reactions.

One exemplary product for such a use is Epipen™. Epipen™ is an auto-injector of Epinephrine for treating anaphylaxis. Generally speaking, at the first sign of a severe allergic reaction, Epipen™ is applied by the user or someone nearby.

However, the effective use of Epipen™ requires the user to correctly detect the first sign of the severe allergic reaction. If there is no one nearby, the user may not be able to apply Epipen™ before the user is disabled by the severe allergic reaction. In addition, if there is someone nearby, it would require such a person to know how to use the Epipen™.

There are some existing automatic detection and insertion devices. Some of the devices involve adjustable needles.

Some existing automatic injection devices require a mounting unit to be manually bent from an insertion angle to a flat (wearable) configuration. In the insertion angle, a needle is inserted that provides a pathway for inserting a sensor. The needle is then pulled back after insertion of the sensor, and the mounting unit is returned to the flat configuration, while leaving the sensor in the user's body.

In other automatic injection devices, the needle is driven through a pre-shaped curve so that the needle is curved to be inserted into the user's body while the rest of the device stays flat.

However, these previous efforts require manual manipulation for pivotal movement and/or insertion of the needle, or involve a curved needle or curved injection paths.

SUMMARY

An example embodiment is a system for automatically detecting whether a user is suffering from a health issue, and when such an issue is detected, automatically injecting the user with a medicine.

In some example embodiments, an auto-injecting device is provided that can inject the user with the medicine with minimal or no effort required from the user. The auto-injecting device may be disposed of and replaced after a single use.

In some example embodiments, sensors are provided to detect physical signs of a user. For example, sensors may be used to detect the heart rate, heart patterns, body temperature, blood oxygen levels, oxygen intake, and/or blood pressure.

In some example embodiments, a controller may be provided that determines when injection is needed. The controller may also control the auto-injecting system to inject the medicine. The controller may determine, based on data from the sensors, the normal physical signs of the user, which is then used as a baseline to determine whether abnormal physical signs occurred and whether such abnormal physical signs would require the injection of the medicine.

An example embodiment is a system for injecting a substance. The system includes an injecting device. The injecting device includes an injecting cartridge, a biasing mechanism, and a latch. The injecting cartridge includes a needle and a plunger, and an injecting mechanism for moving the syringe and pushing the plunger of the syringe. The biasing mechanism is configured to pivot the injecting cartridge from a storage position into an injecting position. The latch is moveable from a holding position for holding the biasing mechanism in the storage position to a release position for releasing the biasing mechanism. The system may also include sensors for measuring the physical signs of a user. The system may further include a controller for controlling the injection of the substance.

BRIEF DESCRIPTION OF THE DRAWINGS

Reference will now be made, by way of example, to the accompanying drawings which show example embodiments, and in which:

FIG. 5B is a front view of the biasing mechanism of the embodiment of FIG. 5A.

FIG. 6C is a front view of the embodiment of FIG. 6A in a closed position.

FIG. 28B is a side view of the device of FIG. 28A.

FIG. 28D is a side exploded view of the device of FIG. 28A.

Similar reference numerals may have been used in different figures to denote similar components.

DETAILED DESCRIPTION OF EXAMPLE EMBODIMENTS

Various example embodiments include an auto-injecting system for injecting medicine or other substances into a user and the method of operation.

Reference is first made to FIGS. 12-15, which show an auto-injecting system 100 in accordance with an example embodiment. The system 100 includes a first wearable band 100A attached to a user's leg and a second wearable band 100B attached to a user s arm. The first wearable band 100A can be worn against the skin of the user or over the clothing of the user. In some example embodiments, the first wearable band 100A include an auto-injecting device 101 that can effect injection into the skin, and through clothing when worn over the clothing over the user. The second wearable band 100B can be worn against the skin of the arm of the user.

Figure 1A:
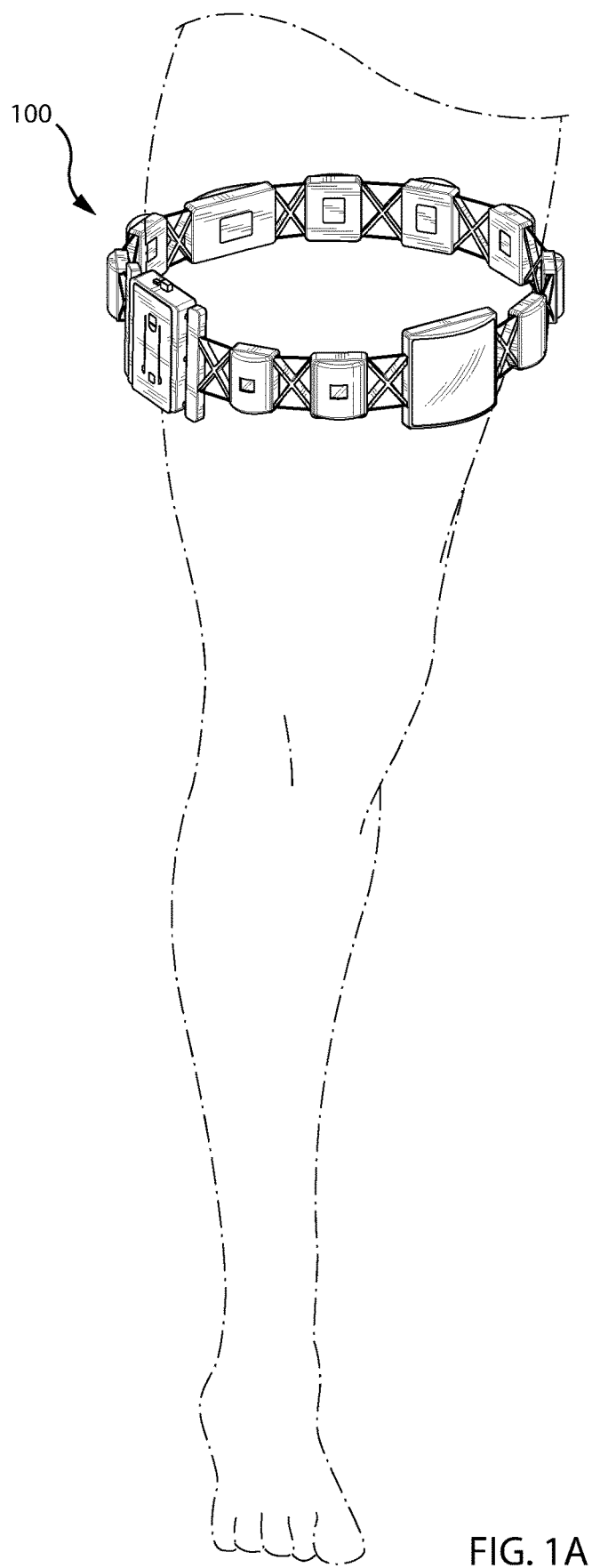
FIG. 1A is a perspective view of the system of one embodiment attached to a user's leg.
Figure 1B:
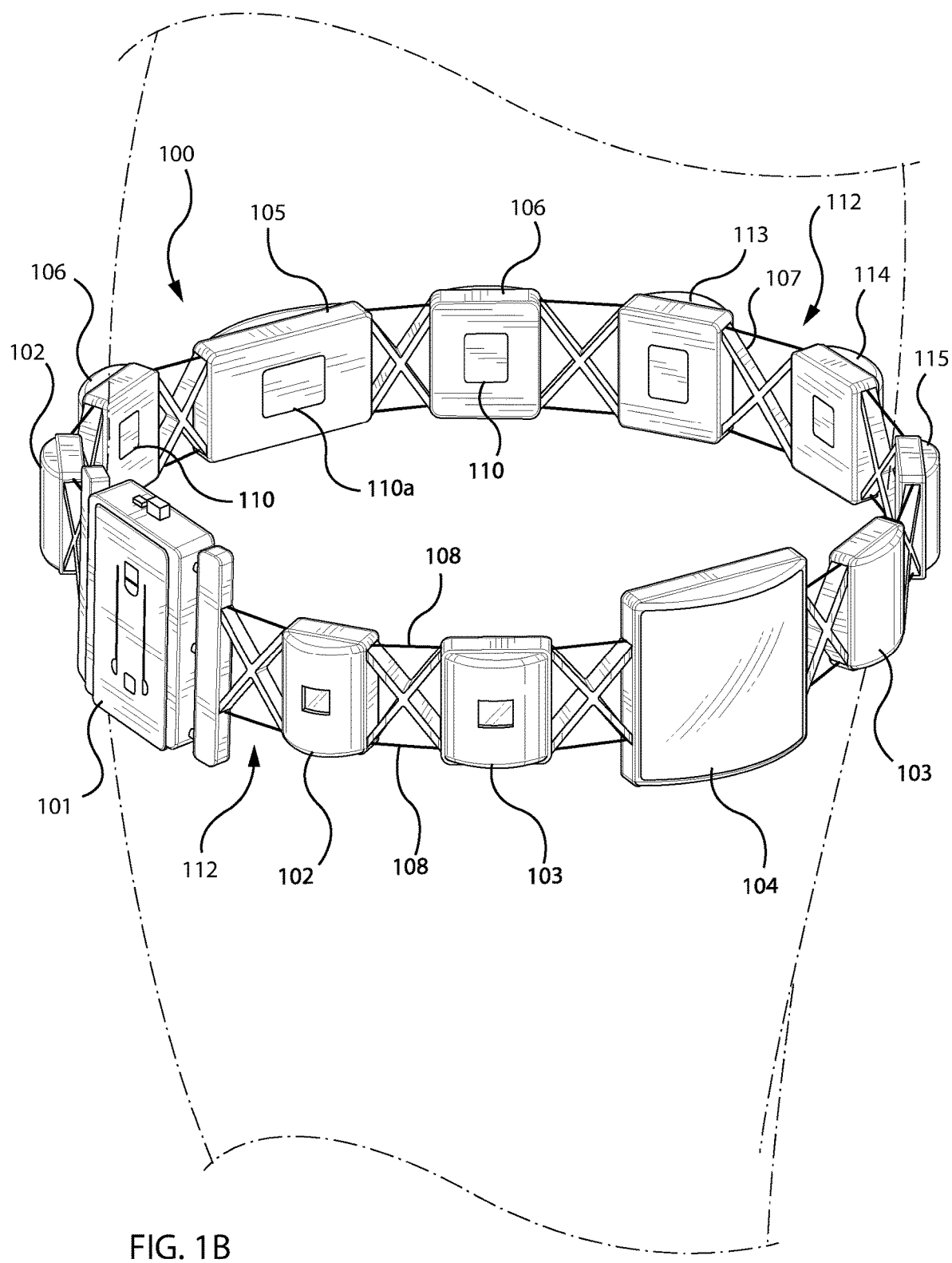
FIG. 1B is an enlarged perspective view of the system of FIG. 1A.
Figure 1C:
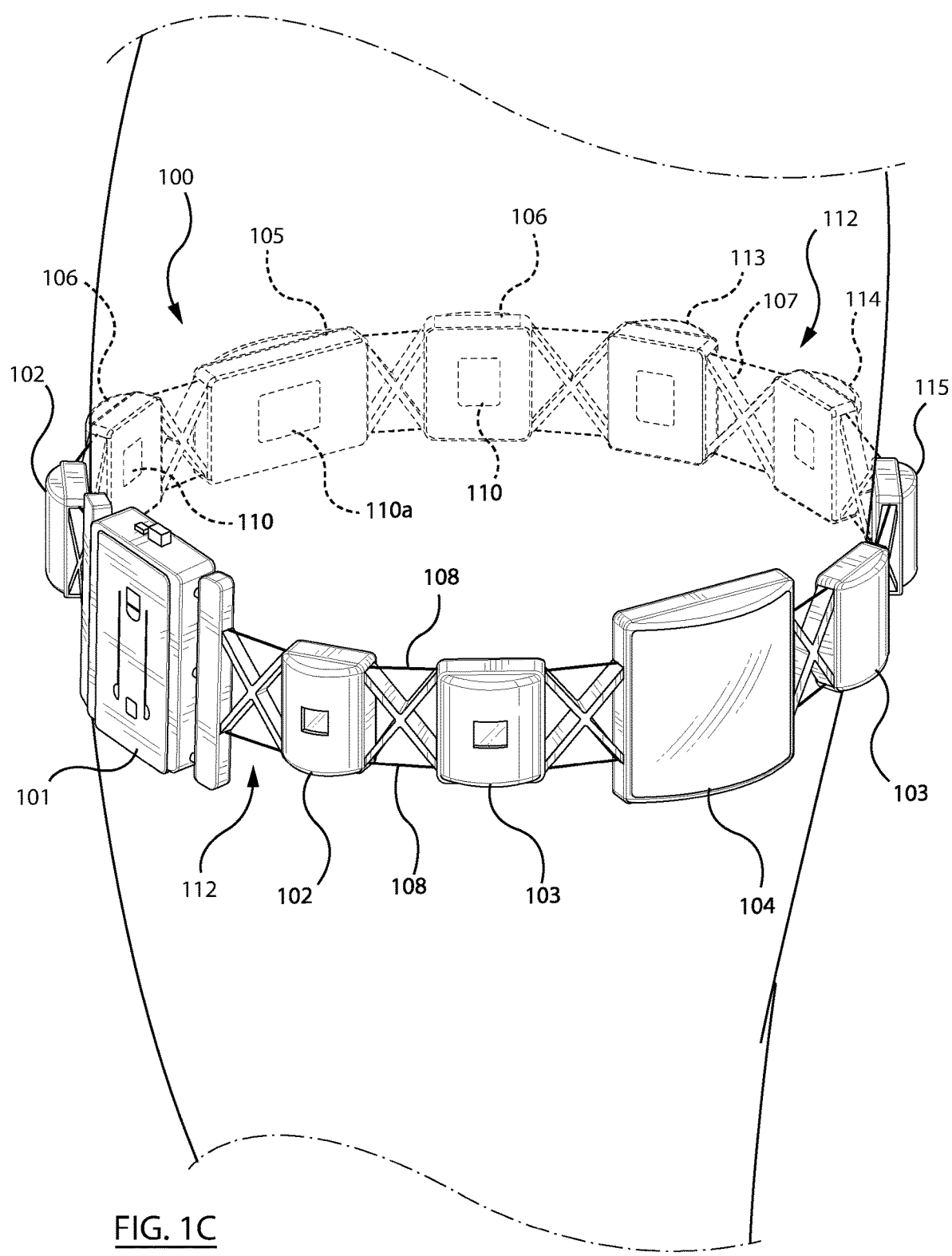
FIG. 1C is an enlarged perspective view of the system of FIG. 1A, in which the user's leg partially blocks the view of the system.
Figure 2A:
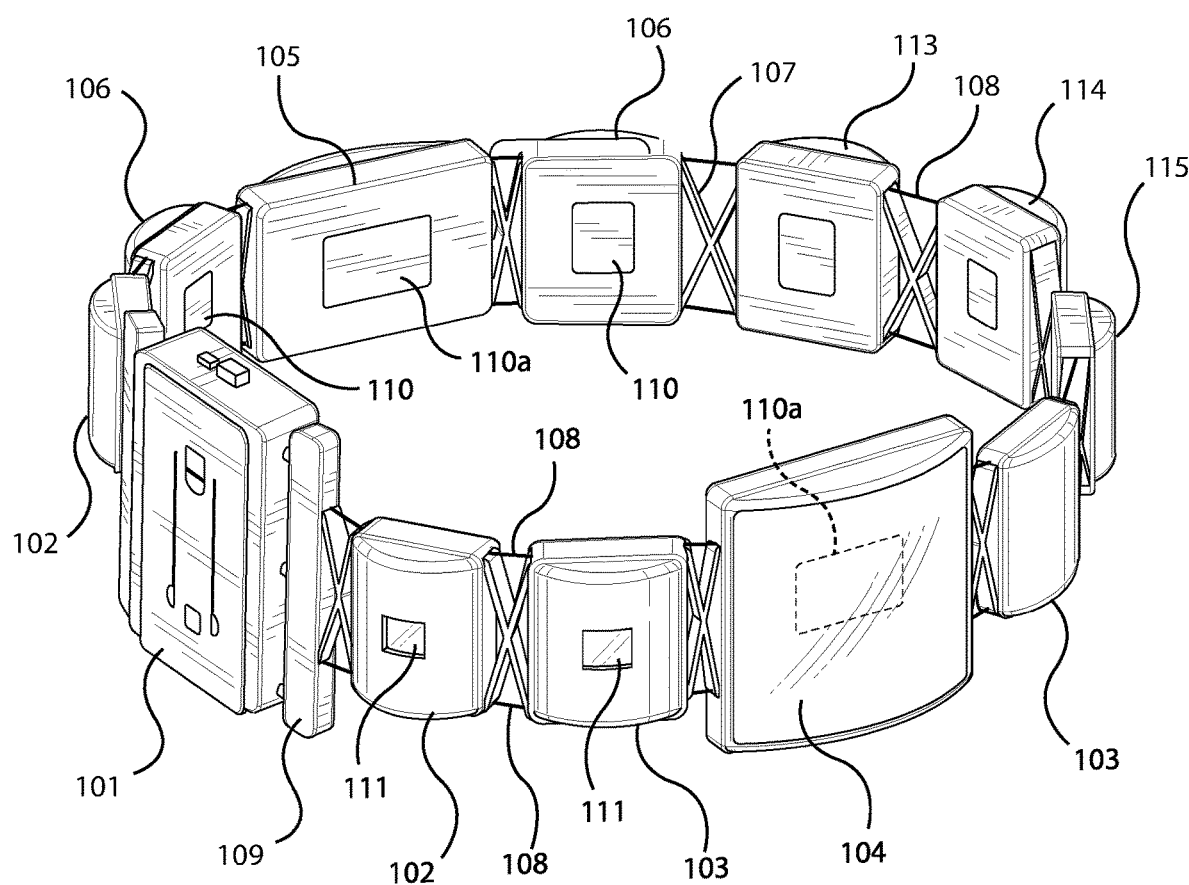
FIG. 2A is a perspective view of the system of FIG. 1A in a contracted state.
Figure 2B:
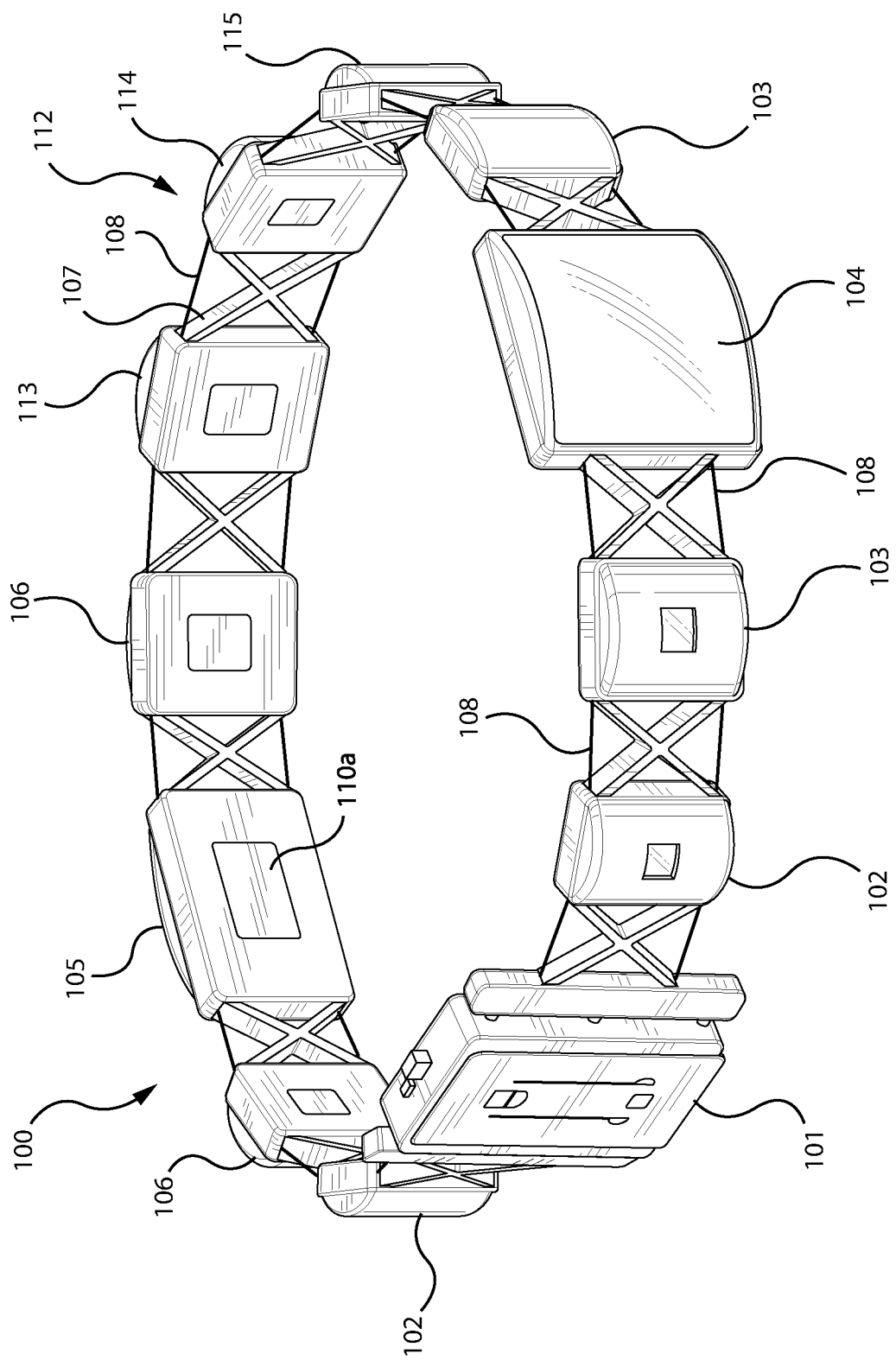
FIG. 2B is a perspective view of the system of FIG. 1A in an expanded state.
Figure 2C:
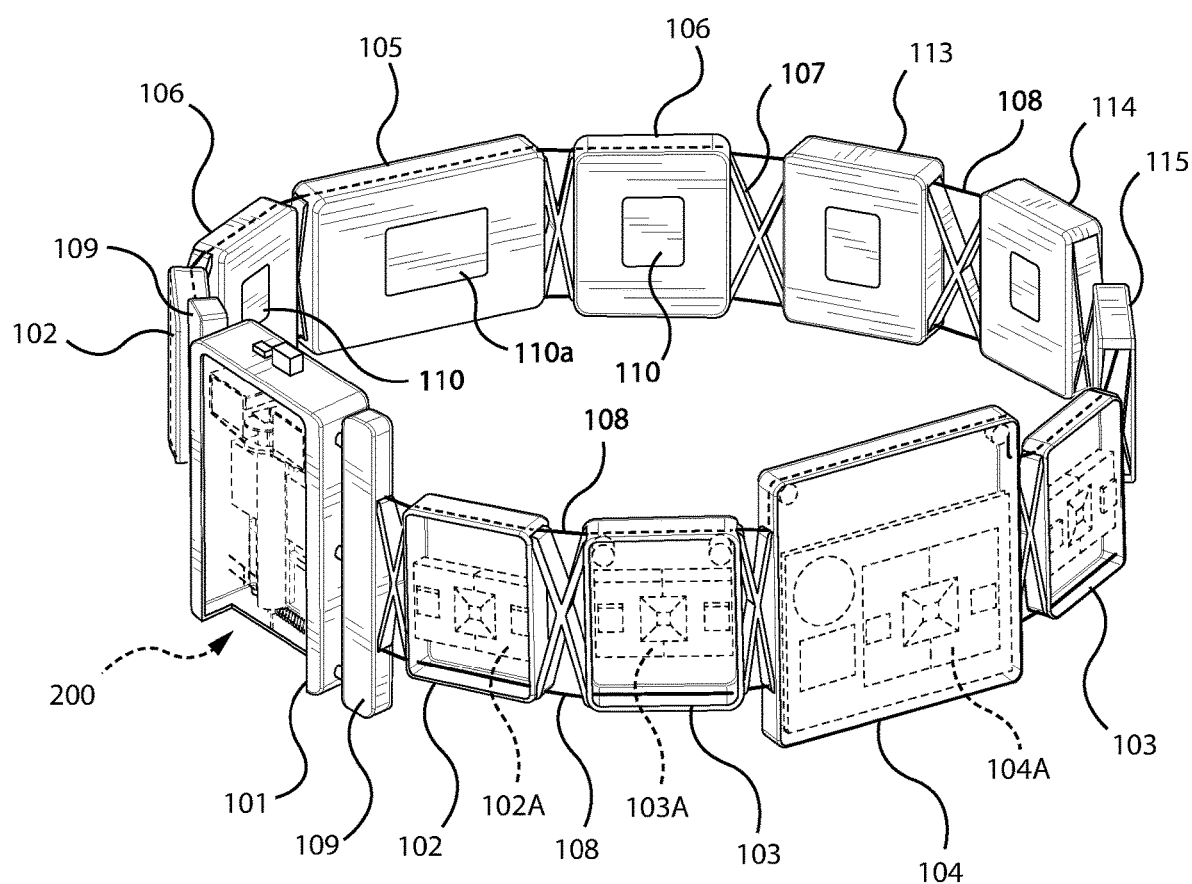
FIG. 2C is a perspective view showing the internals of the components of the system of FIG. 1A.
Figure 3A:
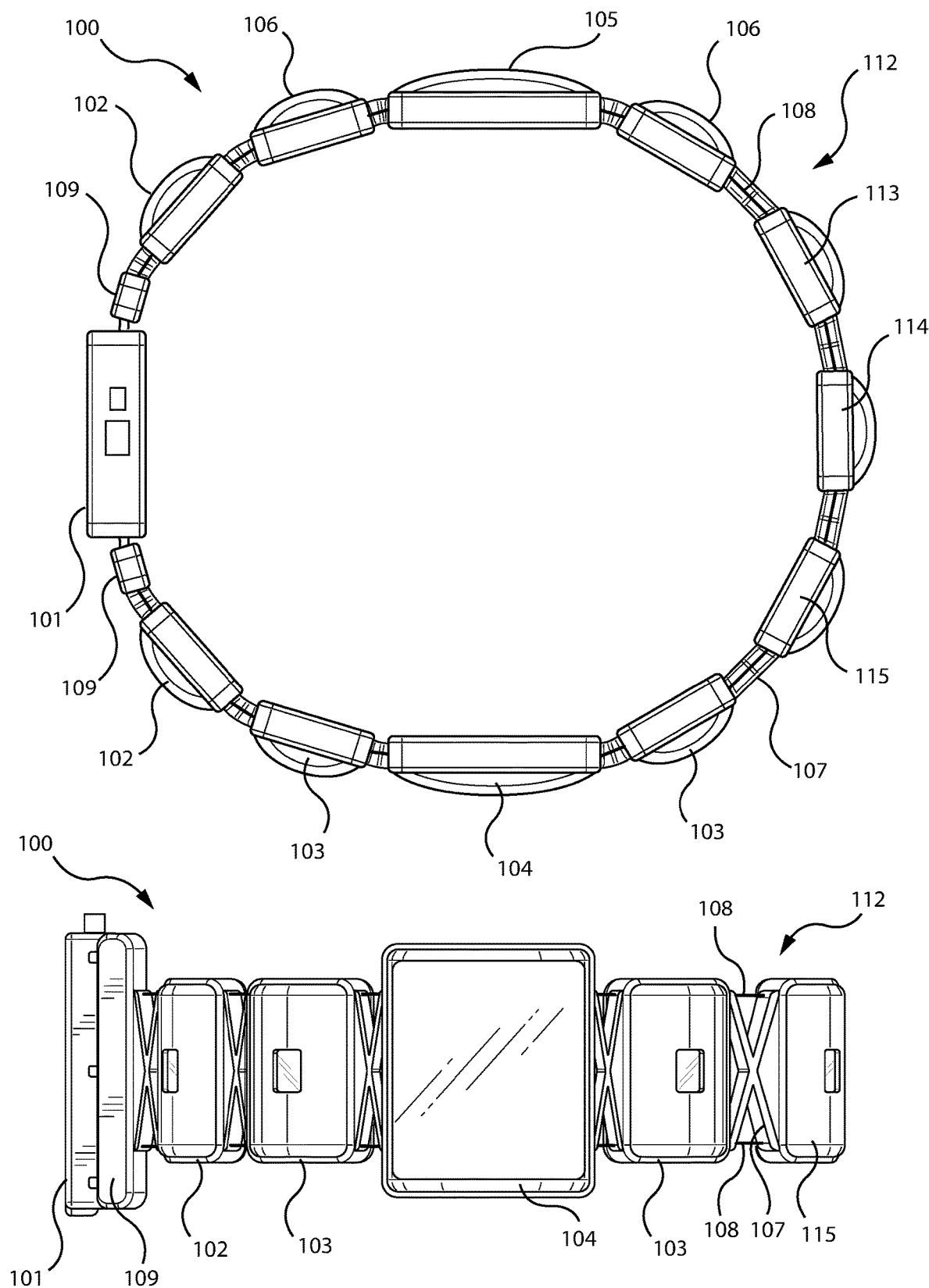
FIG. 3A is the top view and front view of the system of FIG. 1A.
Figure 3B:
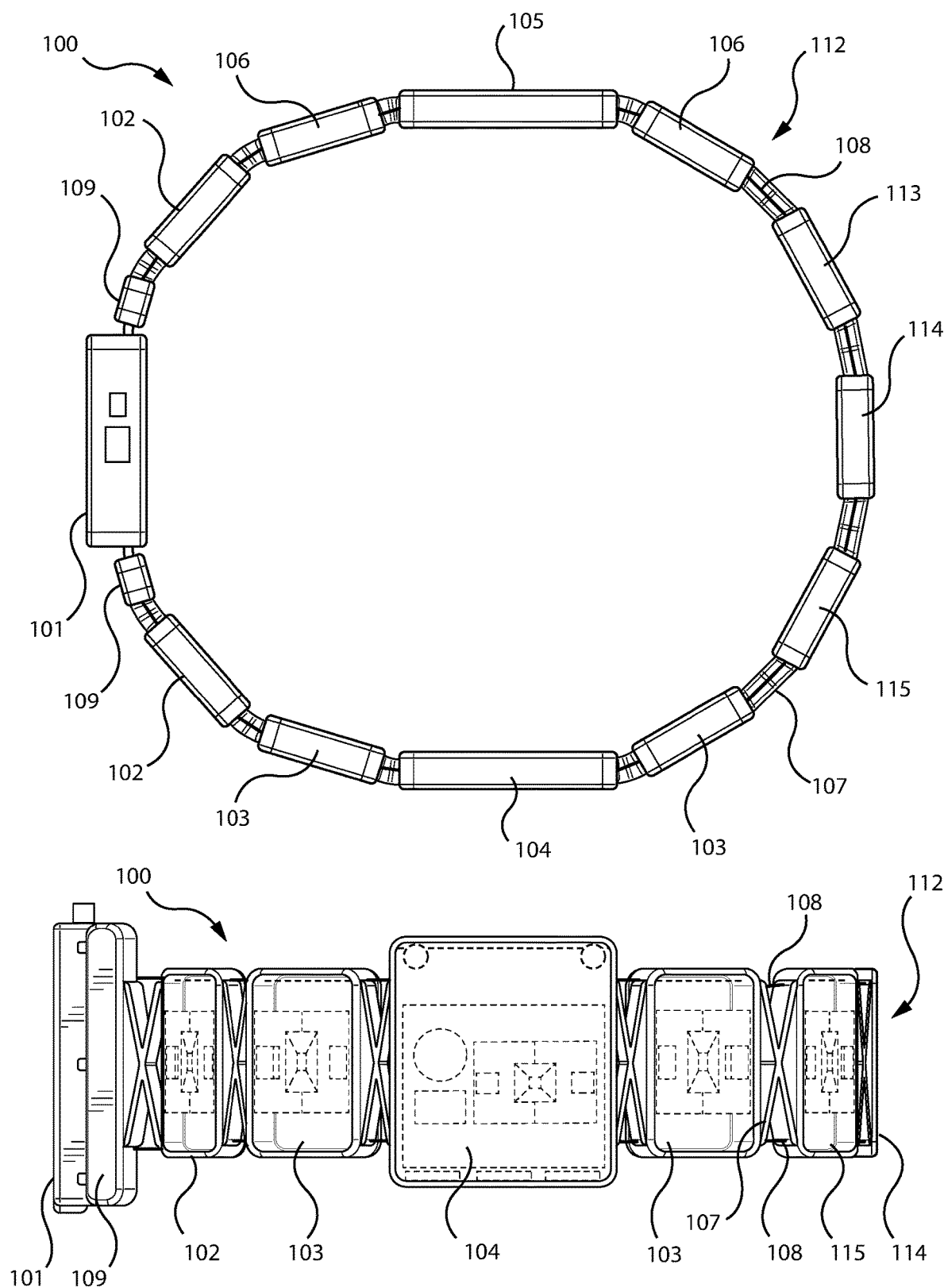
FIG. 3B is the top view and front view of the system of FIG. 1A showing the internals of the components of the system.
Figure 4A:
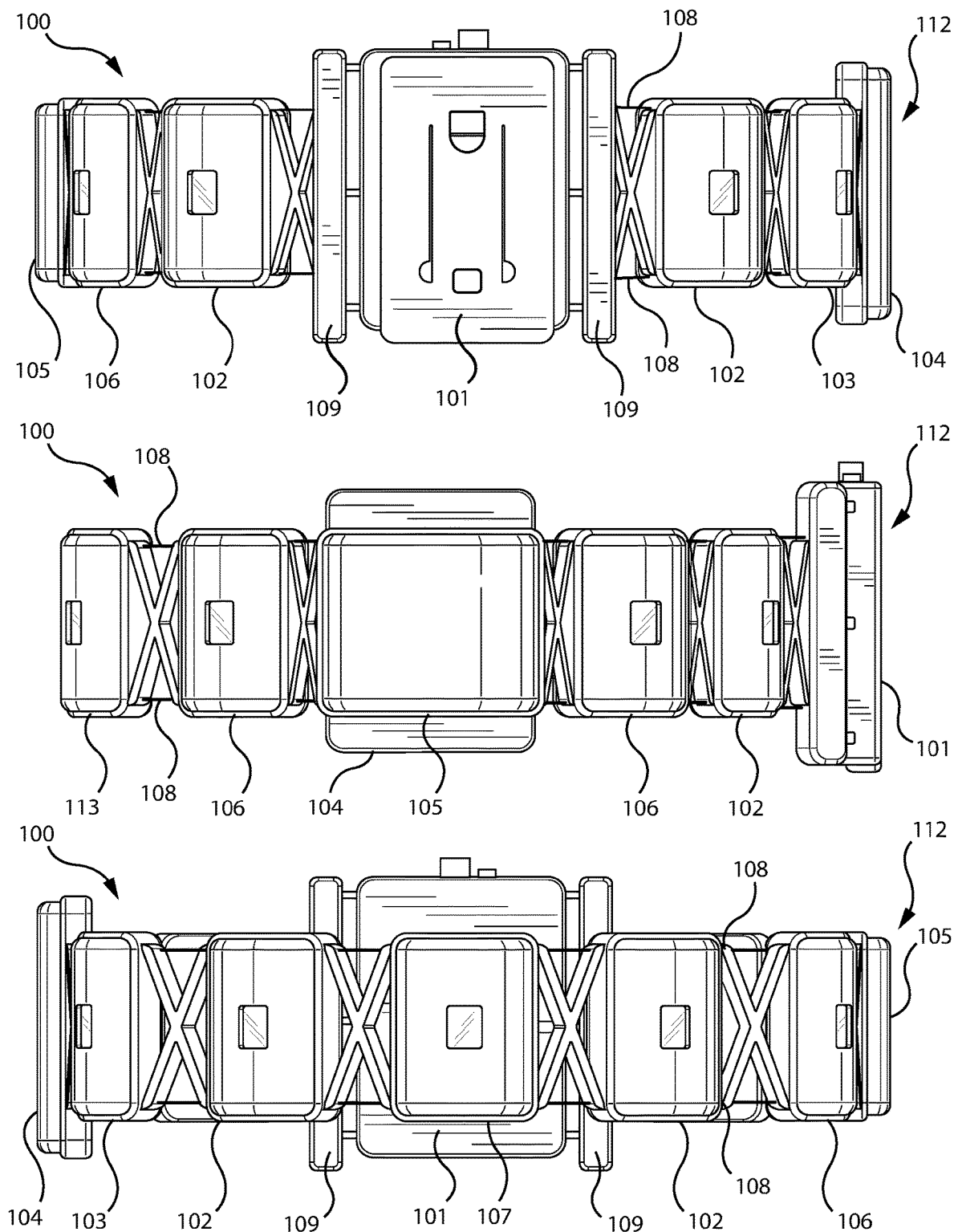
FIG. 4A is the left, back, and right side view of the system of FIG. 1A.
Figure 4B:
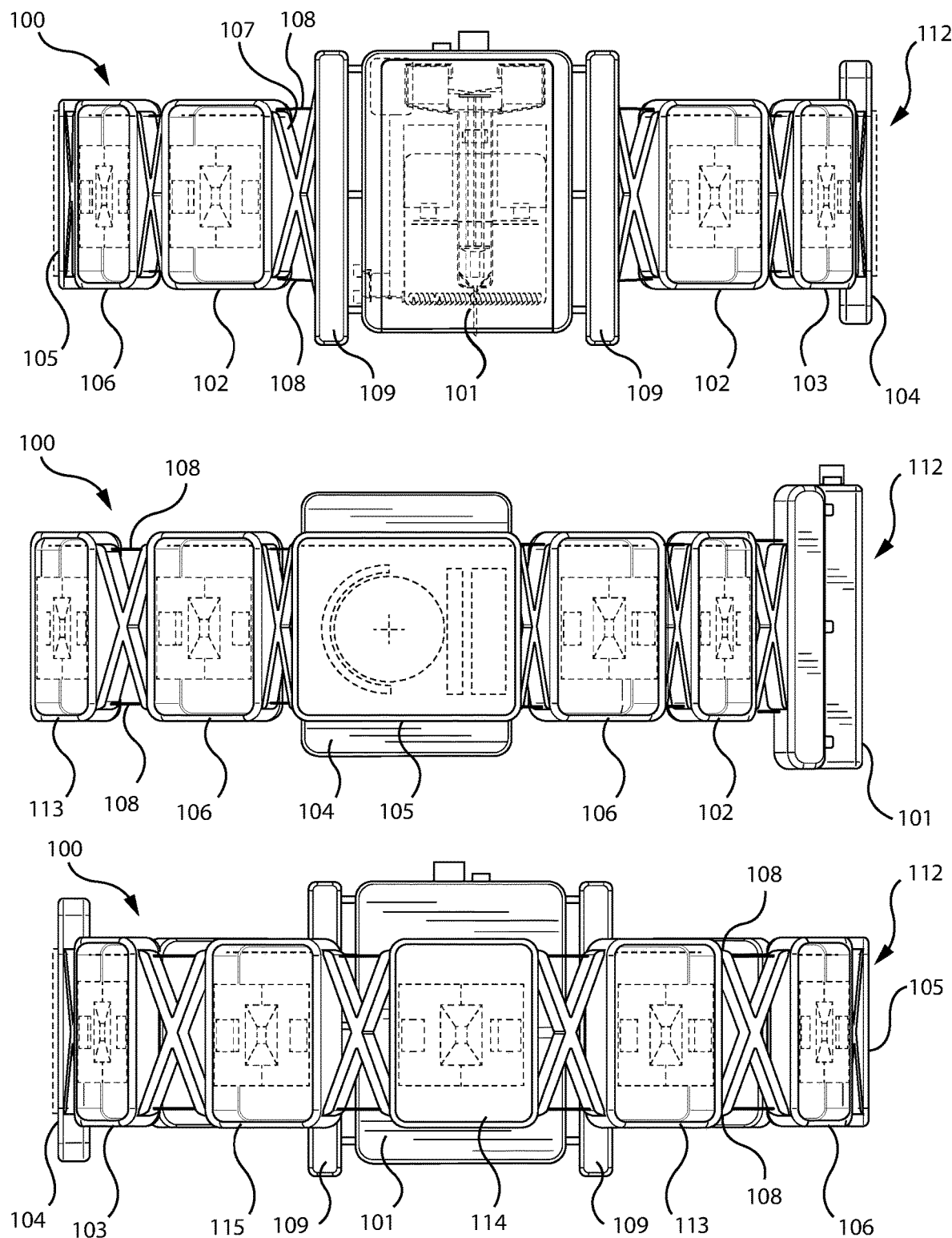
FIG. 4B is the left, back, and right side view of the system of FIG. 1A showing the internals of the components of the system.

Reference is now made to FIGS. 1A, 1B, and 1C, which show another example embodiment of the auto-injecting system 100, in the form of one wearable band 112, such as a leg band, that is attached to the upper thigh of a user. The wearable band 112 can be worn against the skin of the upper thigh of the user. Although upper thigh of a user is the preferred site of injection of medicine, the system 100 may be attached to other suitable parts of the user's body. For example, the system 100 may be a waistband worn around the waist of a user. In another example, the system 100 may be a wearable armband wearable on the arm (e.g. shoulder or forearm) of the user.

Figures 10A, 10B:
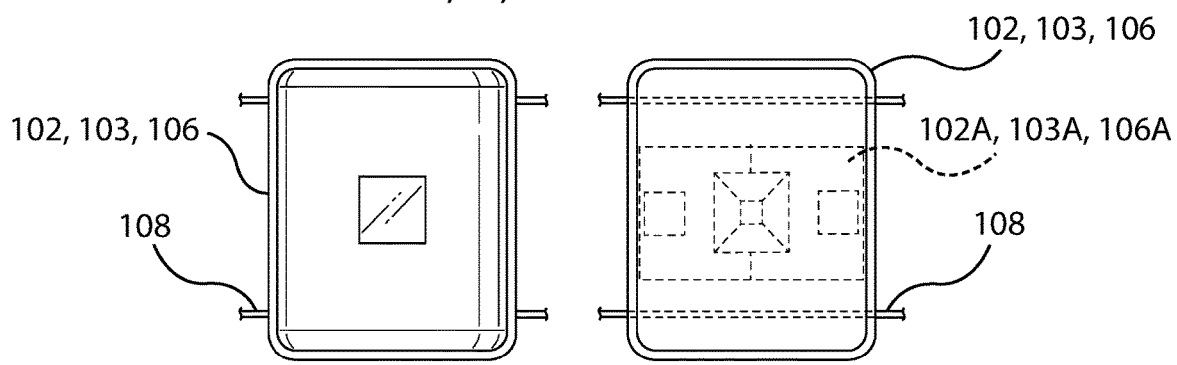
FIGS. 10A and 10B shows the front view and internals of a component comprising the sensor units.

Reference is now made to FIGS. 2A, 2B, 2C, 3A, 3B, 4A, and 4B. In some embodiments, the system 100 includes an auto-injecting device 101. The system 100 may also include display unit 104, battery unit 105, and one or more sensor units, for example, one or more blood oxygen sensor unit 102, heart rate (HR) monitor unit 103, IR sensor unit 106, and blood pressure sensor unit 114. In an example, each of these sensor units include optical sensors that emit and detect signals through a respective window 110 or 110a. The oxygen sensor unit 102 includes sensor component 102A. The HR monitor unit 103 includes HR sensor component 103A. The IR sensor unit 106 includes IR sensor component 106A as shown in FIG. 10B.

The HR monitor unit 103 can monitor the heart rate and heart pattern of the user. The IR sensor unit 106 can detect the body temperature of the user. The oxygen sensor unit 102 can detect the oxygen intake of the user or the oxygen content in the blood of the user. And the blood pressure sensor unit 114 can detect the blood pressure of the user. The described various sensor units include optical sensors in various example embodiments, rather than conductive sensors that require conductive leads.

Figures 9A, 9B:
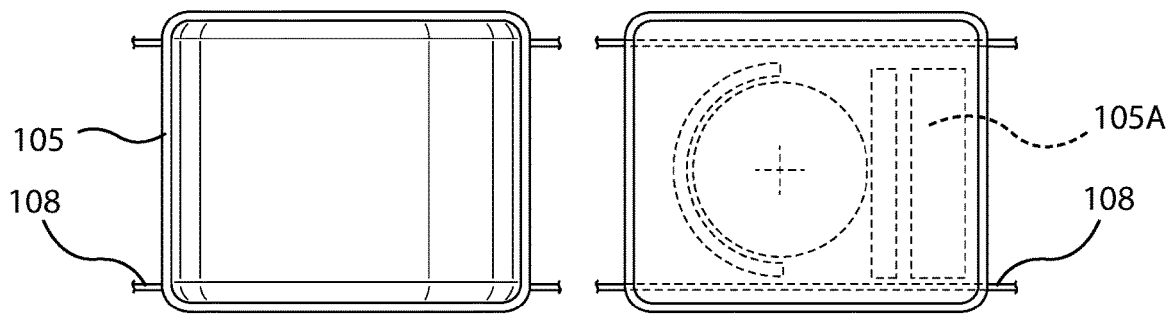
FIGS. 9A and 9B show the front view and the internals of a battery unit of the system.

The battery unit 105 supplies power for the functions of the system 100. There may be a power input interface so that the battery unit 105 may be charged. The power supplied through the power input interface may also be used for the function of the system 100. There may be multiple batteries integrated with the various components of the system. In some examples, the batteries may be rechargeable and/or replaceable. The battery unit 105 includes battery component 105A, as shown in FIG. 9B.

The display unit 104 may be LCD, LED, OLED, or based on any other suitable technology. The data detected by the sensors may be displayed on the display unit 104 to help user or a caregiver to make a decision. The display unit 104 includes display component 104A.

In some embodiments, the wearable band 112 includes resilient crosslinks 107 and the strings 108 are retractable strings that are disposed between the units of the system 100. The resilient crosslinks 107 may be made of rubber or thermoplastic elastomers (TPE). In some embodiments, the crosslinks 107 are strong and flexible. For example, the crosslinks 107 can be made of composite material. The units of the system 100 can be attached to and supported by the wearable band 112 by various mounting or attachment mechanisms.

In some embodiments, the strings 108 are elastic and resilient. For example, the strings 108 may be made of rubber, or TPE. As such, the strings 108 and the crosslinks 107 can be manually expanded for removing the system 100 from the user, and the system 100 can be securely attached to the user when the strings 108 and the crosslinks 107 are in a normal or resting state. In an example, each individual string 108 is positioned substantially around the entire circumference of the wearable band 112. In other examples, there are segments of the string 108 positioned at different arcs (segments of the circumference) of the wearable band 112.

In some embodiments, the wire activating component 109 is a string tightening component that is used to pull or draw on the string 108 so that the strings are tightened onto the body of the user. For example, there may be a spool that is driven by a motor (not shown) in the wire activating component 109 to tighten the strings 108. The string tightening component can include an actuator, solenoid (can also be called a linear solenoid), or a motor, for example.

In some embodiments, the strings 108 include muscle wire, and a wire activating component 109 is a muscle wire activating component that is used to contract and relax the muscle wire. The muscle wire activating component can be a controller that provides a current to the muscle wire, causing the muscle wire to contract (or remain contracted if already contracted). The controller of the muscle wire activating component can also provide no current to the muscle wire, causing the muscle wire to relax (or remain relaxed if already in a relaxed state). The muscle wire may be of a length to attach to the user's body securely but comfortably. The muscle wire may be insulated (not shown).

The muscle wire may also be configured of a length that requires the muscle wire activating component 109 to regulate the electric current supplied to the muscle wire, causing the muscle wire to contract upon receiving the electric current, thus attaching the system 100 to the user's body. When the electric current is turned off, the muscle wire returns to its original state (also known as recovery or recover) and the system 100 may be removed from the user.

In some embodiments, a controller 113 is provided.

In some embodiments, an interface is provided such that a user may calibrate the sensors and interact with the controller 113.

In some embodiments, the controller 113 analyzes the data received from the sensors using predetermined routines to determine whether injection of medicine is needed.

In some embodiments, the controller 113 processes the data received when the user is in a normal state to set a baseline representing the normal state of the user. For example, the heart rate, blood oxygen level, and oxygen intake at the normal state may be stored in a memory as the baseline.

When the physical signs of the user changes, the data representing this changed state may be compared to the baseline. The controller 113 may then analyze the difference and determine whether medicine is required. Different parameters may be stored in a memory to be used by the controller 113 so that the controller 113 may determine the health issue that is occurring, for example, heart failures, stroke, severe allergic reactions, etc. In some examples, the medicine can be adrenaline for heart failures, epinephrine for severe allergic reactions, etc.

In an example, when the user is exercising, the difference in data may show that although the heart rate and body temperature are higher than normal, the oxygen intake is also higher than normal. The controller 113 may then determine, based on the stored parameters, that the user is exercising and no medicine is needed. The controller 113 may also analyze the difference and determine that medicine is required. For example, the difference may show that the heart rate increases significantly while oxygen intake is significantly reduced, and the body temperature of the user changes. The controller 113 may then determine, based on the stored parameters, that severe allergic reaction is occurring, and medicine is required.

In some embodiments, the controller 113 is provided with a checking routine to recheck the data, for example, through the verification routine, from one or more of the sensors to determine if there is a false alarm. If it is determined that there is a false alarm, the controller 113 may alert the user that there has been a false alarm. In response to the determination of a false alarm, the controller 113 may return to the standby state.

If the controller 113 determines that an injection is needed, the controller 113 may alert the user of the physical condition. An interface may be provided so that the alert and the injection and alert may be interrupted by the user or caregiver, locally or remotely. If there is no response, the controller 113 may proceed with the injection process.

Figure 11:
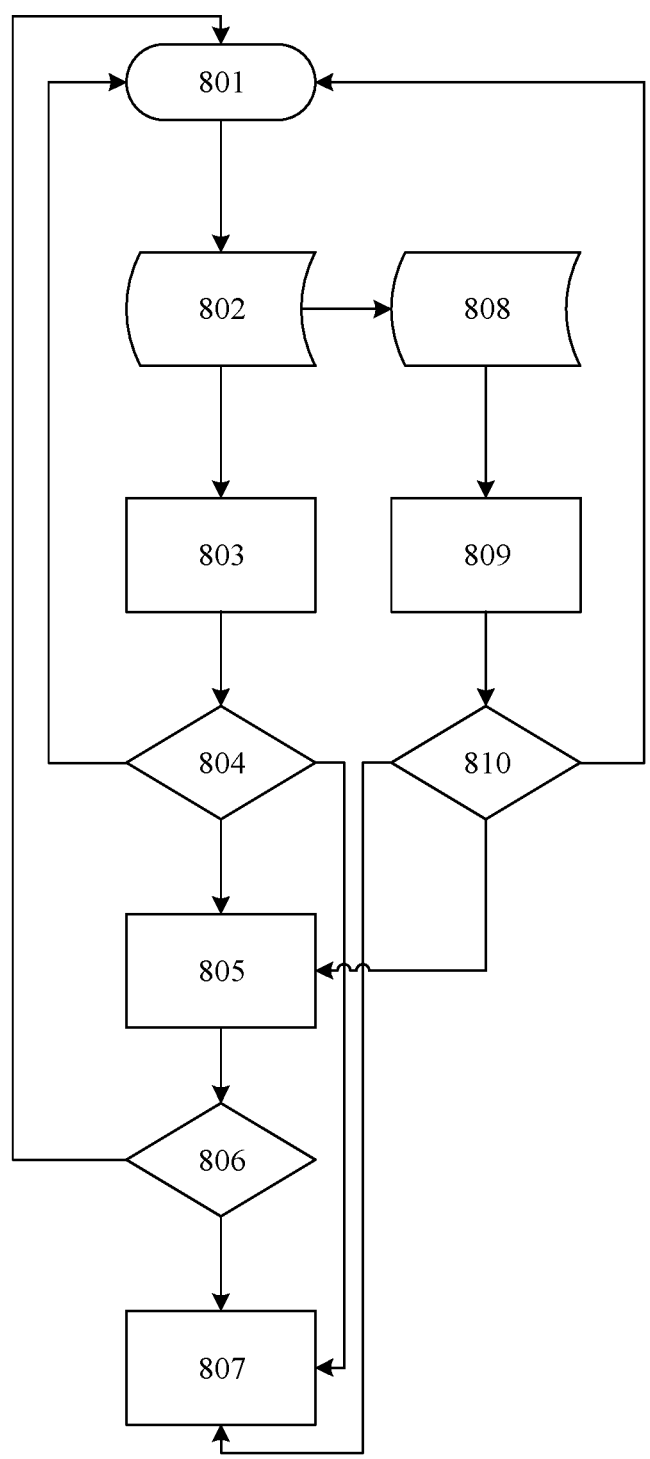
FIG. 11 is a flowchart of an auto-injecting process performed by the system, in accordance with an example embodiment.

Examples of the automatic injecting process are shown in the flowchart of FIG. 11. At step 801, the controller 113 is at a standby state. At step 802, the controller 113 receives data from the sensors. At step 803, the controller 113 processes and analyzes the data from the sensors. At step 804, the controller 113 determines whether injection of medicine is needed. If it is determined that there is no such need, the controller 113 returns to the standby state of step 801. If it is determined that injection is needed, the controller proceeds to step 807 to signal the auto-injecting device 101 to proceed with injection of the medicine.

In some embodiments, the process includes steps 808, 809, 810. After receiving data from the sensors at step 802, the controller 113 double checks the system 100, and receives another set of data from the sensors at step 808. At step 809, the controller 113 processes the different sets of data to ensure that the data received from the sensors is accurate. At step 810, the controller 113 determines whether injection is needed. If it is determined that no injection is needed, the controller 113 returns to the standby state of step 801. If it is determined that injection is needed, the controller 113 proceeds to step 807 to signal the auto-injecting device 101 to proceed with injection of the medicine.

In some embodiments, steps 805 and 806 are included. If it is determined that injection is needed, an alert is provided to the user at step 805. The user can input to the controller 113 at step 806 whether to proceed with injection. If the user decides not to proceed and input an interruption command, the controller 113 returns to the standby state of step 801. If the user does not interrupt, then the controller 113 proceeds to step 807 to signal the auto-injecting device 101 to proceed with injection of the medicine.

In some embodiments, when an injection is needed, the controller 113 signals the wire activating component 109 (muscle wire activating component in this example) to cause the strings 108 (muscle wire string in this example) to contract such that the muscle wires are securely attached to the body of the user, thereby securing the system 100 to the body of the user to facilitate injection.

In some embodiments, when injection is needed, the controller 113 signals the wire activating component 109 (string tightening component in this example) to further tighten (pull) the strings so that the strings 108 are securely attached to the body of the user, thereby securing the system 100 to the body of the user to facilitate injection.

The status of the user and the stage of the injecting process, etc. may be displayed on the display unit 104. For example, the display unit 104 may show that medicine is needed, the controller 113 will initiate auto-injection, etc.

The controller 113 may continue to receive data from the sensors to determine whether the condition of the user is relieved after injection of the medicine.

The system 100 may also be provided with one or more communication components such that the controller 113 can wirelessly communicate, for example, through Wi-Fi, Bluetooth, mobile internet, or cellular services, with other person or organization in the vicinity, for example, hospitals or Emergency medical services (EMS), to alert them of the situation so that emergency services may be provided. The physical signals may be communicated so that the preparations may be made in advance. The physical signals may be continuously communicated. In some embodiments, step 807 also includes notifying local authorities, hospitals, etc.

The system 100 may also include an application ("app") on a smartphone or a dedicated device that connect to the rest of the system 100, for example, through the Bluetooth connection, so that the user or caregiver may monitor the physical signals, intermittently or continuously. The app, through the smartphone, or the dedicated device may communicate with other service providers through the internet, for example, when an emergency situation arises. The app or the dedicated device may also incorporate a machine learning function to adaptively adjust the parameters of the system 100 to improve performance. The app or the dedicated device may also communicate with a cloud computing environment that provides machine learning function so that the data from multiple systems 100 in use can be used for adjusting the parameters to improve performance of the systems 100.

The system 100 can be provided with a GPS sensor 115 so that the location of the user can be communicated to other person or organization.

The controller 113 can be configured to provide a signal indicating a system failure. The signal may be an audible alarm from a speaker (not shown) and/or display on the display unit 104. The signal may be communicated to nearby persons or organizations through the communication components.

The controller 113 may also be configured to provide alarms so that persons nearby can be notified of the emergency situation.

In some embodiments, the components are integrated in a single unit that is attached to the wearable band 112. In some embodiments, the auto-injecting device 101 is formed in a unit and the other components are integrated in different units. In some embodiments, the auto-injecting device 101 is in a unit separate and detachable from the wearable band 112, such that the auto-injecting device 101 can be disposed of and replaced after use without incurring the cost of replacing the other components. The device 101 may comprise a platform 200 that is attached to the wearable band 112. In some embodiments, each of the units is separate. The wearable band 112 is generally circular or oval.

Reference is now made to FIGS. 5A, 5B, 5C, 5D and 5E, which illustrate an embodiment of the auto-injecting device 101. The auto-injecting mechanism 231 includes a compressed gas tank 213, which may be movably attached to rail 214. A syringe 201 may be movably attached to rail 209. The syringe 201 is attached to a conveyor 208 by straps 230. The conveyor 208 is connected to an actuator 207 by shafts 217. The gas tank 213 is pre-punctured, and the puncture is plugged by a plug 212. In some embodiments, the plug 212 which is hollow. The plug 212 is blocked by a release valve 211 disposed in a manifold 203 that connects the gas tank 213 and the top 218 of the plunger 219 of the syringe 201. Thus, the release valve 211 blocks the pressurized gas in the gas tank 213 from being released. In some embodiments, the release valve 211 is connected to an actuator that can move the release valve 211 such that the plug 212 is not blocked by the release valve 211. All these components are disposed in an injecting cartridge 300 which may be removable and replaceable. The rails 209 and 214 are fixed to the injecting cartridge 300. In some embodiments, the actuator 207 is a servo.

In some embodiments, vibration motors 228 are provided on the lower corners of the device 101 for massaging the skin and muscle of the user to facilitate the injection.

Grip 305 is provided on the outside of the injecting cartridge 300. The grip 305 is connected to the head of a pin 304, which is connected to the release valve 211, such that the pulling on the grip 305 dislodges the release valve 211. As a result, the pressurized gas in the gas tank 213 is released through the hollow plug 212. An exhaust 303 is provided on an exterior wall of the injecting cartridge 300, and the exhaust 303 is positioned above the top 218 of the plunger 219. In some embodiments, the exhaust 303 is a valve. In some embodiments the exhaust 303 is a one-way valve such that gas can only flow from the interior of the device 101 to its exterior through the exhaust 303. A handle 302 is also provided on the exterior of the injecting cartridge 300, the handle 302 engages the conveyor 208 when the handle 302 is pulled up to a predetermined position. A window 301 may be provided for the user or caregiver to see the status of the medicine, for example, the amount of medicine available.

The device 101 may be connected to two muscle wire activating component disposed on either side of the device 101 for contracting or relaxing two wires 216. In other examples, one muscle wire activating component is used to control (provide a current to) the two wires 216. In example embodiments, the wires 216 may be elastic or inelastic.

Figure 5A:
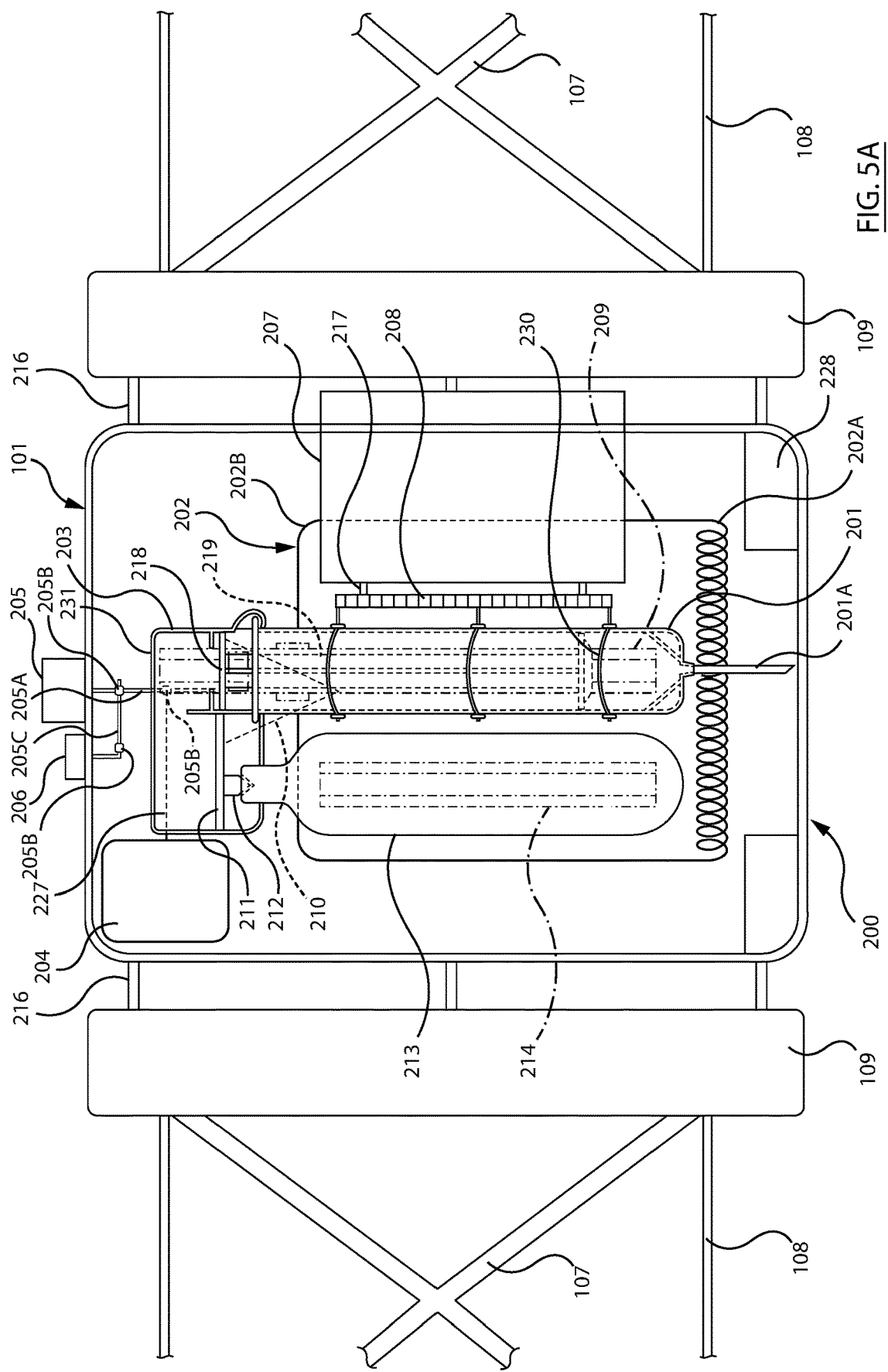
FIG. 5A is a front view of the internals of one embodiment of the auto-injecting device.
Figure 5C:
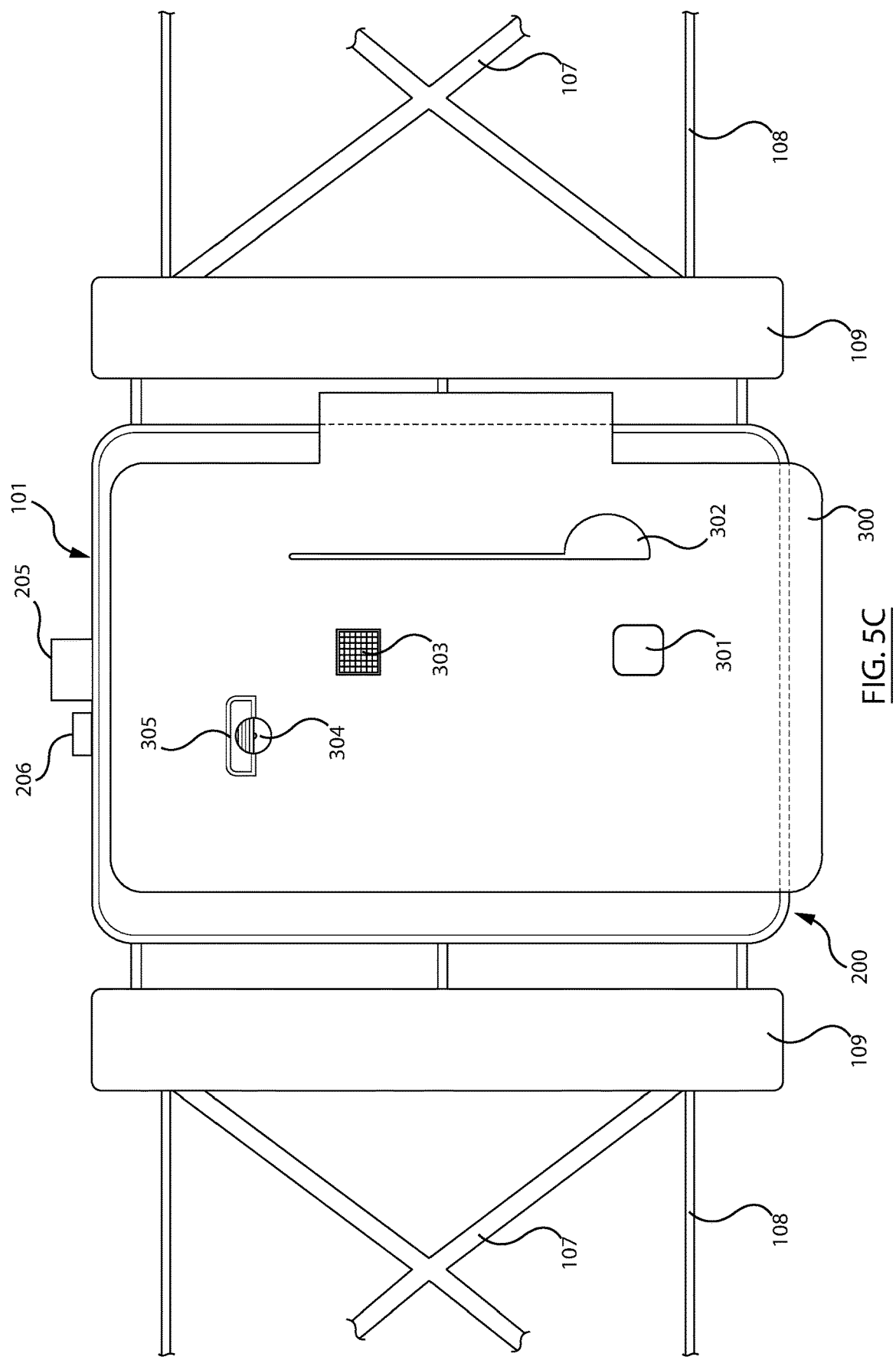
FIG. 5C is a front view of the embodiment of FIG. 5A in a closed position.
Figure 5D:
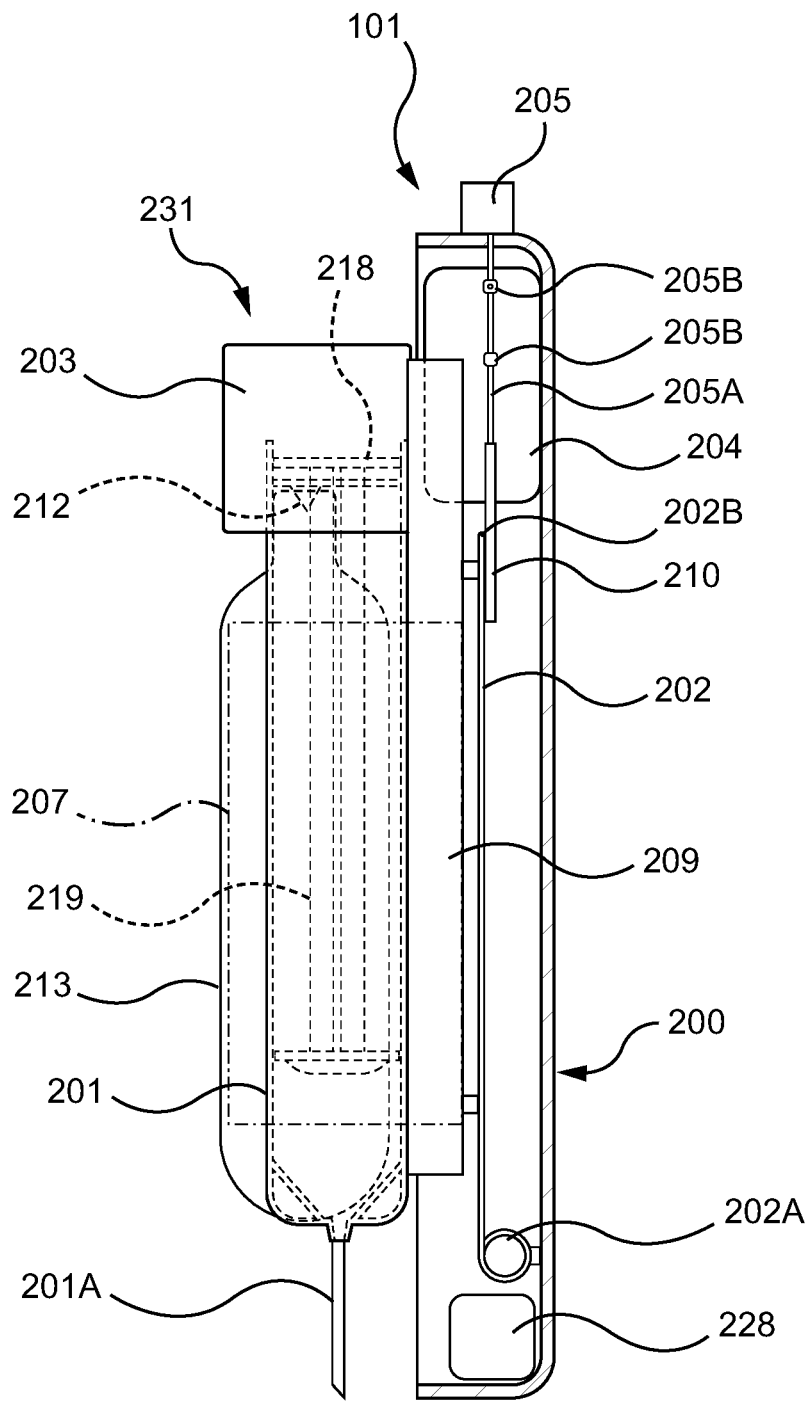
FIG. 5D is a cross-sectional side view of the embodiment of FIG. 5A showing the internals of the embodiment.

There is also provided a biasing mechanism 202. In an example embodiment, the biasing mechanism comprises spring 202A and bar 202B. The biasing mechanism is disposed between the syringe 201 and the auto-injecting mechanism 231 and the bottom of the device 101, as shown in FIG. 5D. In some embodiments, the biasing mechanism 202 is disposed between the injecting cartridge 300 and the bottom of the device 101. In some embodiments, the biasing mechanism 202 is disposed between the injecting cartridge 300 and the platform 200.

A latch 210 is provided that holds the bar 202B of the biasing mechanism in place in a storage position such that the syringe 201 is lying parallel to the resilient crosslinks 207 when injection of medicine is not needed. The storage position of the syringe 201 is substantially tangential to the circumference of the wearable band 112, and therefore substantially tangential to the skin of the user. The latch 210 is connected to a shaft 205A that is connected to a shaft 205C and a shaft 227 at joints 205B. The shaft 205C is connected to the knob 206. The knob 206 is movable between a locked positon and a release position. When the knob 206 is in the locked position, the shaft 205C is connected to the shaft 205A such that the shaft 205A cannot be moved away from the biasing mechanism 202, locking the latch 210. When the knob 206 is in the release position, the shaft 205C no longer blocks the movement of the shaft 205A, such that the shaft 205A can be moved to release the latch 210. In some embodiments, an actuator (not shown) is provided to move the knob 206 between the locked position and the release position. In some embodiments, the knob 206 may be moved manually. The shaft 227 is connected to an actuator 204. In some embodiments, the actuator 204 is a servo. When the actuator 204 moves the shaft 227 away from the biasing mechanism 202, the latch 210 is moved away from the biasing mechanism 202, thus releasing the biasing mechanism 202. The knob 205 may be moved manually to pull the shaft 205A away from the biasing mechanism 202, thus moving the latch 210 to release the biasing mechanism 202.

As shown in FIG. 5D, the components within the injecting cartridge 300, in particular, the syringe 201 and the gas tank 213, rest in a closed position when the device 101 is not in use.

Figure 5E:
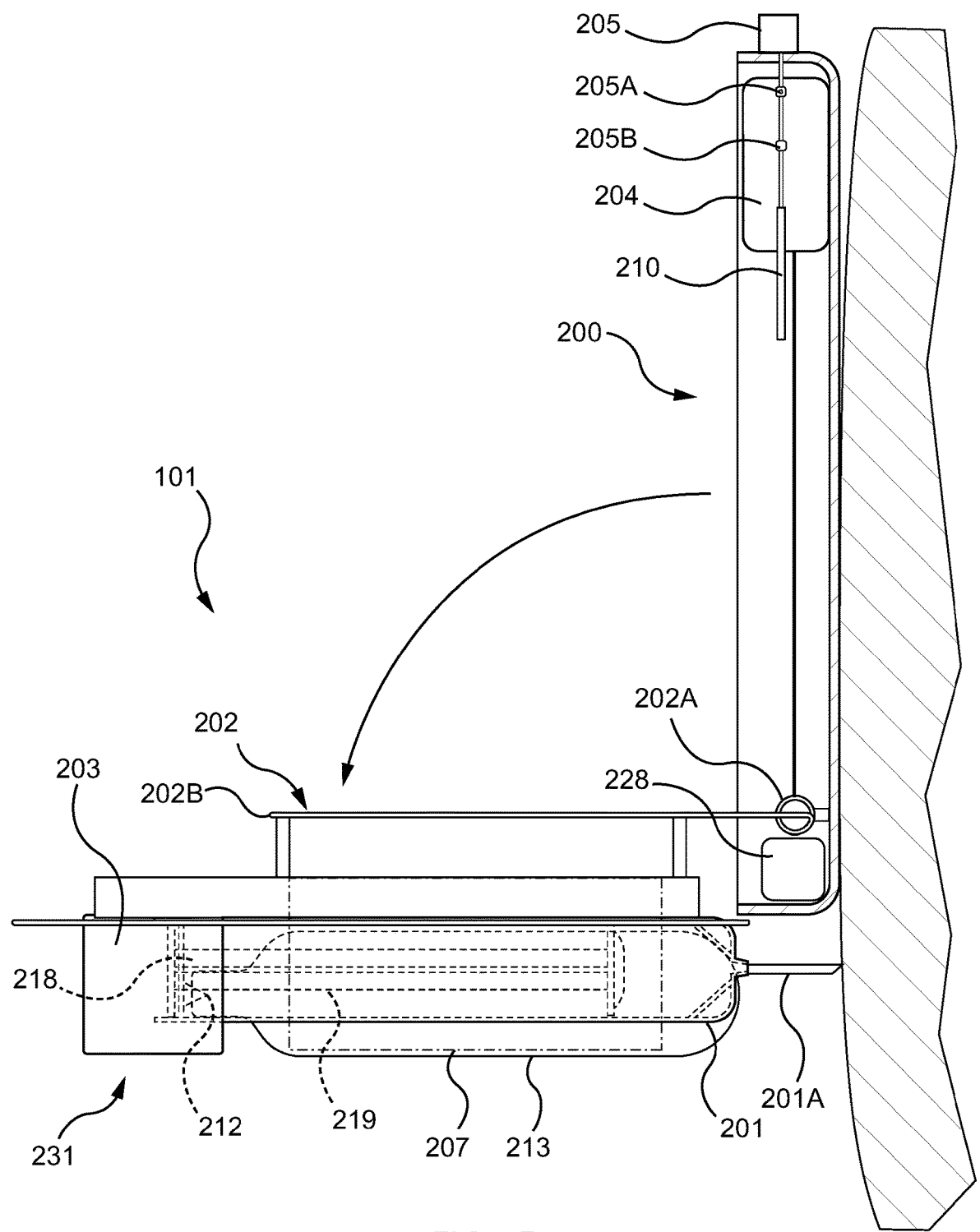
FIG. 5E is a side view of the embodiment of FIG. 5A in an activated state.

When the controller 113 determines that injection of medicine is needed, the controller 113 sends a signal to the actuator to move the knob 206 to the release position, and signals the actuator 204 to move the shaft 227, which in turn moves the latch 210 to release the bar 202B of the biasing mechanism. The biasing mechanism 202 then causes the injecting cartridge 300 to pivot away from the rest of the device 101 until the syringe needle 201A is at a predetermined angle relative to the skin of the user, i.e., until the syringe is in an injecting position, as shown in FIG. 5E. A holding mechanism may be provided to hold (lock) the injecting cartridge 300 in the desired position. For example, the holding mechanism may be a limiter to the spring 202A or the injecting cartridge 300 such that the spring 202A or the injecting cartridge 300 stops at a certain angle.

Figure 5F:
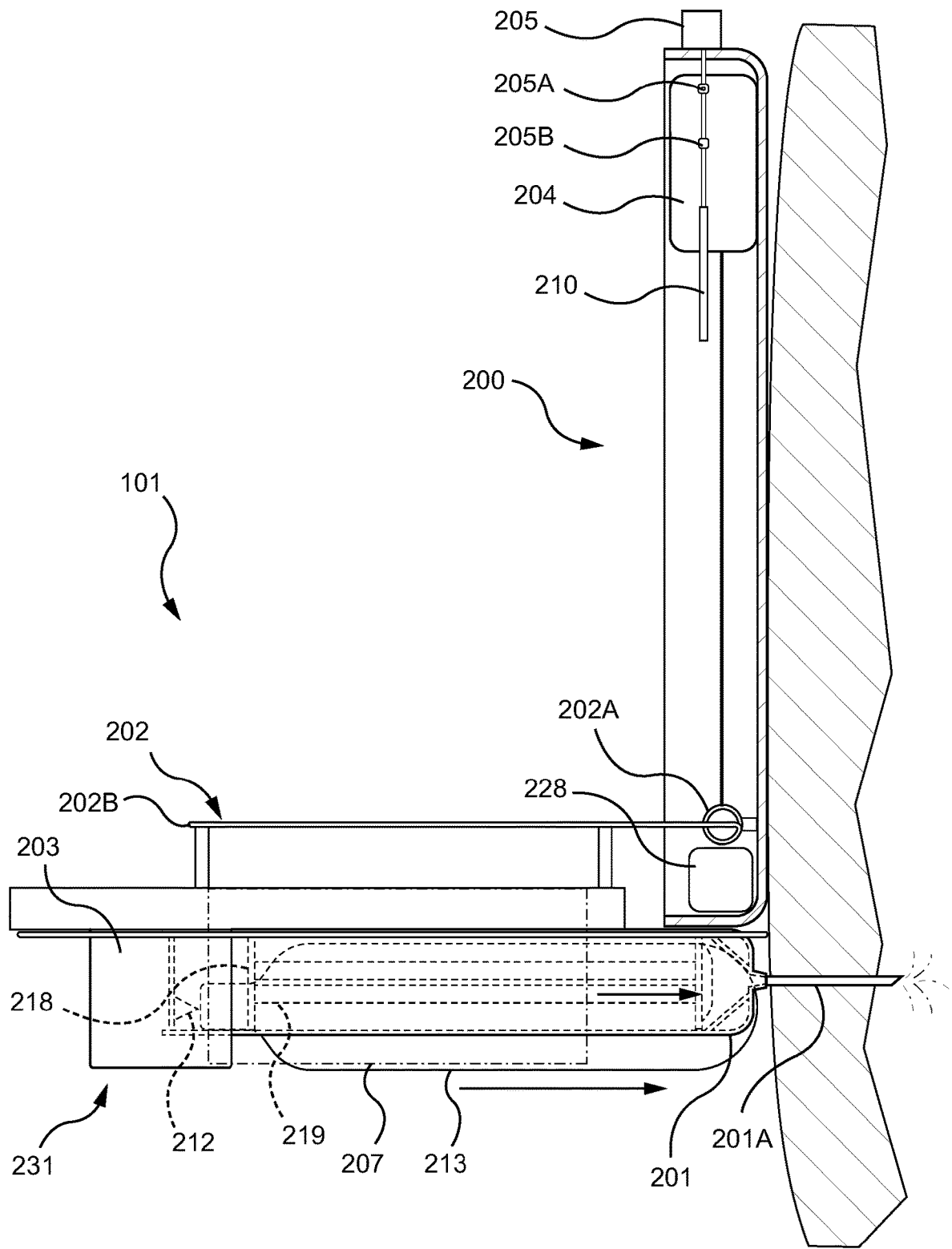
FIG. 5F is a side view of the embodiment of FIG. 5A in an injection state.

The controller 113 then signals the actuator 207 to cause the shafts 217 to move towards the user (radially inward to the wearable band 112). The shaft 217 in turn moves the conveyor 208, which in turn moves the syringe 201 toward the user. By the connection through the manifold 203, the gas tank 213 and the manifold 203 move simultaneously with the syringe 201. The rails 214 and 209 facilitate smooth and accurate movement of the syringe 201 and the gas tank 213. By the movement of the syringe 201, the needle 201A is inserted into the skin of the user, as shown in FIG. 5F. During the movement of the syringe 201, the vibration motors 228 may be activated to facilitate insertion of the needle 201A.

When the needle 201A is inserted to a predetermined depth into the user, the controller 113 signals the servo 207 to stop. The controller 113 then signals an actuator (not shown) to move the release valve 211 such that the plug 212 is no longer blocked, causing the gas in the compressed gas tank 213 to flow into the manifold 203 through the hollow plug 212. The gas pushes on the top 218 of the plunger 219, causing the medicine in the syringe to be injected into the user. The excess gas is released through the exhaust 303.

If there is a malfunction in the system such that the injection cannot be automatically performed, the controller 113 may provide an alert to the user, for example, by audible alarm and/or display on the display unit 104, indicating the failure of the system if the controller 113 is not malfunctioning. Upon the alert or if the user so desires, the user may move the knob 206 to the release position and manipulate the knobs 205 to release the latch 210, thus releasing the biasing mechanism so that the injecting cartridge 300 is positioned at a predetermined angel relative to the skin of the user. The handle 302 may then be pulled up, which engages the conveyor 208 and then the handle 302 may then be pushed toward the user's skin, causing the syringe 201 to move toward the user's skin such that the needle 201A is inserted. After the needle 201A is inserted into the user at a predetermined depth, the user may then pull the grip 305 to remove the release valve 211 such that the medicine may be injected. Depending on the malfunction, one or more of these steps may be performed manually. If the controller 113 is malfunctioning, the user may perform these steps manually when desired.

In some embodiments, the biasing mechanism 202 comprises an actuator that holds the injecting cartridge 300 in place when injection is not needed. Upon receiving a signal from the controller 113, the actuator moves the injecting cartridge such that the syringe needle 201A is positioned at the injecting position. The actuator then holds the injecting cartridge 300 in the injecting position. If there is a malfunction in the actuator, the injecting cartridge 300 may be manually moved into the injecting position. And the other manual steps may be performed as described for injecting the medicine.

After the injection, the device 101 or the injecting cartridge 300 and the components therein may be removed and replaced.

Reference is now made to FIGS. 6A, 6B, 6C, 6D, 6E, 6F and 6G. A different embodiment of an auto-injecting device 101 is provided. The auto-injecting mechanism 231 includes actuators 220, which has shafts 221 that are connected to a connector 222 that connects the shafts 221 to the syringe 201, the syringe 201 being attached to the connector 222. The syringe 201 may be movably attached to a rail 209 so that the movement of the syringe is smooth and precise. Each combination of the actuator 220 and the shaft 221 may collectively be a linear solenoid.

There are also provided actuators 223 that are fixedly disposed within holders 224. The holders 224 are fixed to an enlarged portion of the syringe 201. The actuators 223 are provided with arms 225 that are disposed adjacent the top 226 of the plunger 219 of the syringe 201. These components are provided in an injecting cartridge 400, as shown in FIG. 6C. In some embodiments, the rail 209 is formed as a part of the injecting cartridge 400. Although two actuators 223 are shown in the figures, it is understood that there may be one or more actuators 223.

Figure 6A:
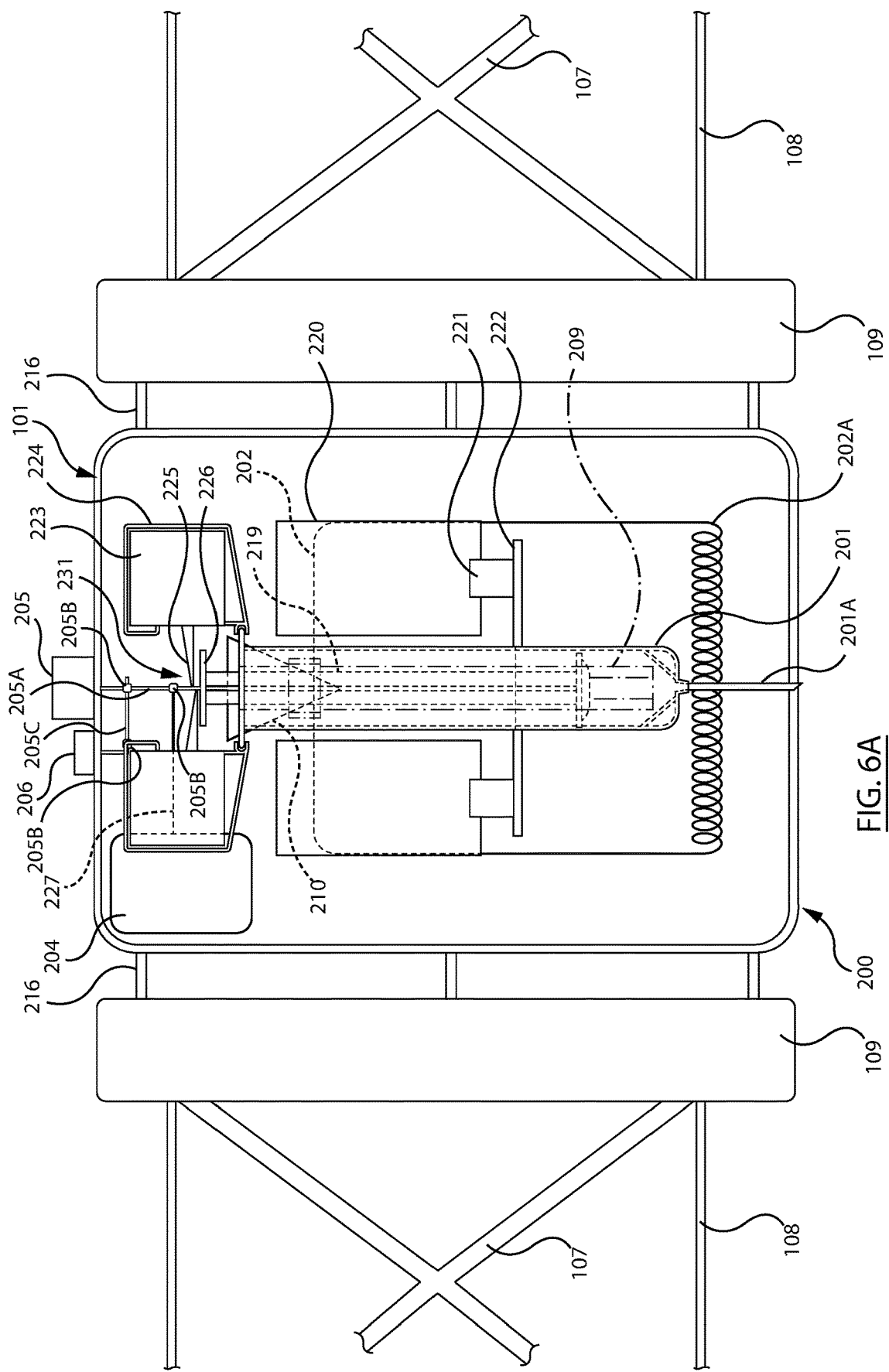
FIG. 6A is a front view of the internals of another embodiment of the auto-injecting device.
Figure 6B:
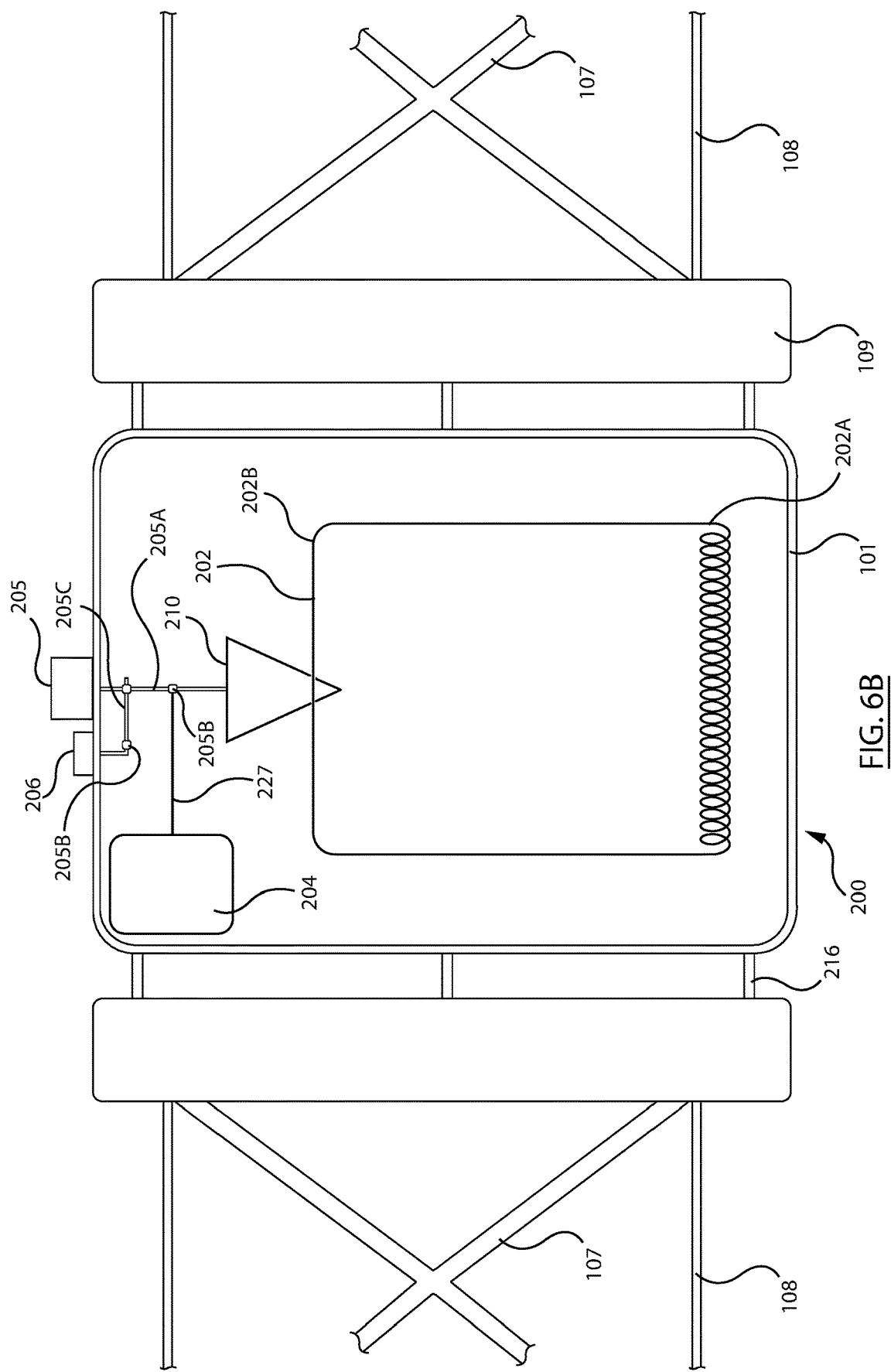
FIG. 6B is a front view of the biasing mechanism of the embodiment of FIG. 6A.
Figure 6D:
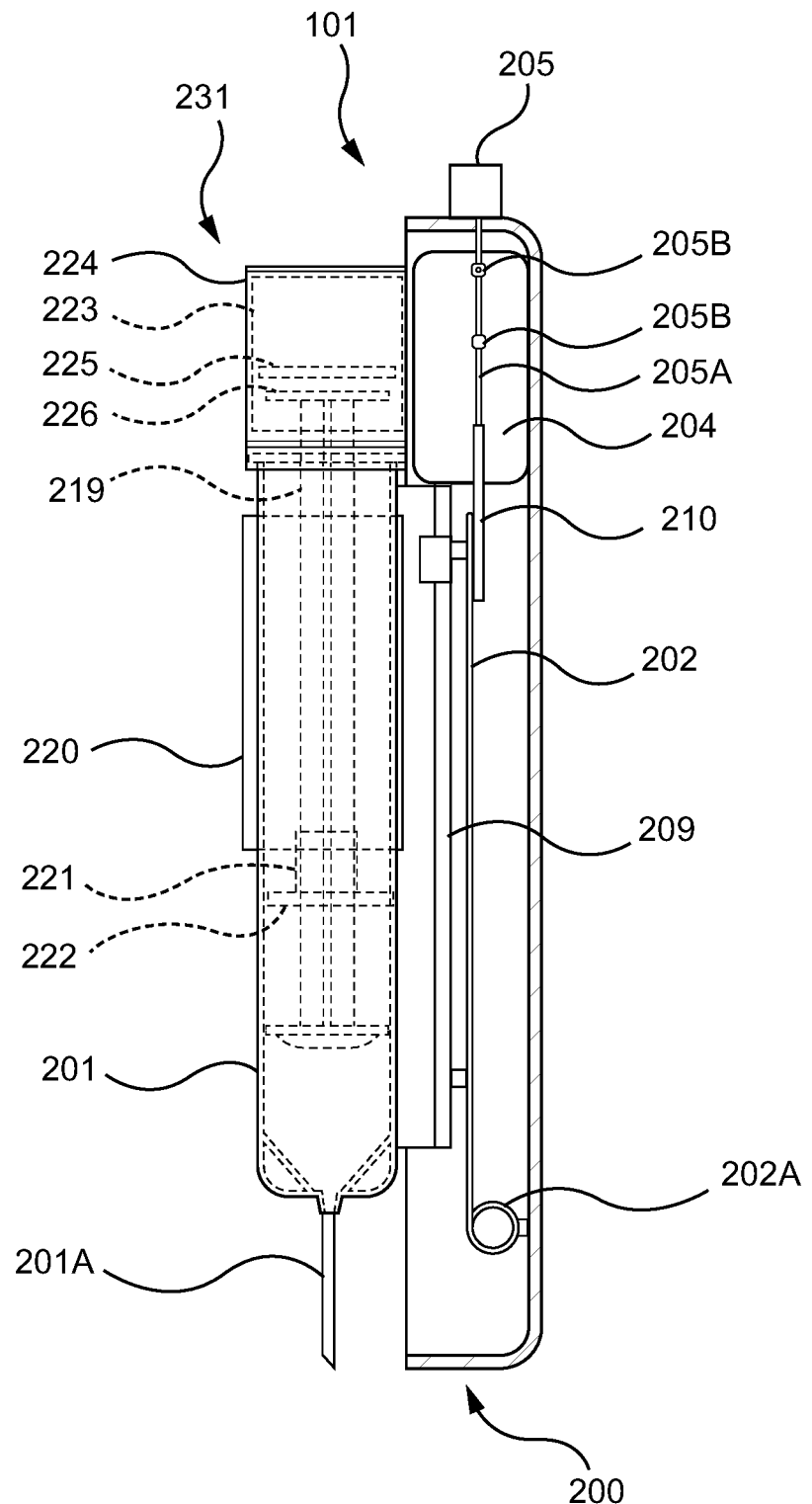
FIG. 6D is a side view of the embodiment of FIG. 6A showing the internals of the embodiment.

In this embodiment, the biasing mechanism is the same as the biasing mechanism as discussed above with respect to the embodiment represented by FIGS. 5A, 5B, 5C, 5D, 5E and 5F. As shown in FIG. 6D, the biasing mechanism is disposed between the syringe 201 and the auto-injecting mechanism 231 and the bottom of the device 101. In some embodiments, the biasing mechanism 202 is disposed between the injecting cartridge 400 and the bottom of the device 101. In some embodiments, the biasing mechanism 202 is disposed between the injecting cartridge 400 and the platform 200.

A window 401 may be configured on the exterior of the injecting cartridge 400 such that a user or caregiver can see the amount of medicine. Two handles 402 are provided, which, when lifted to a predetermined position, engage the connector 222. Another window 403 is provided on the injecting cartridge 400. A bar 404 is disposed in the window 403. The bar 404 engages the plunger 219 of the syringe 201, for example, by engaging the top 226 of the plunger 219.

Figure 6E:
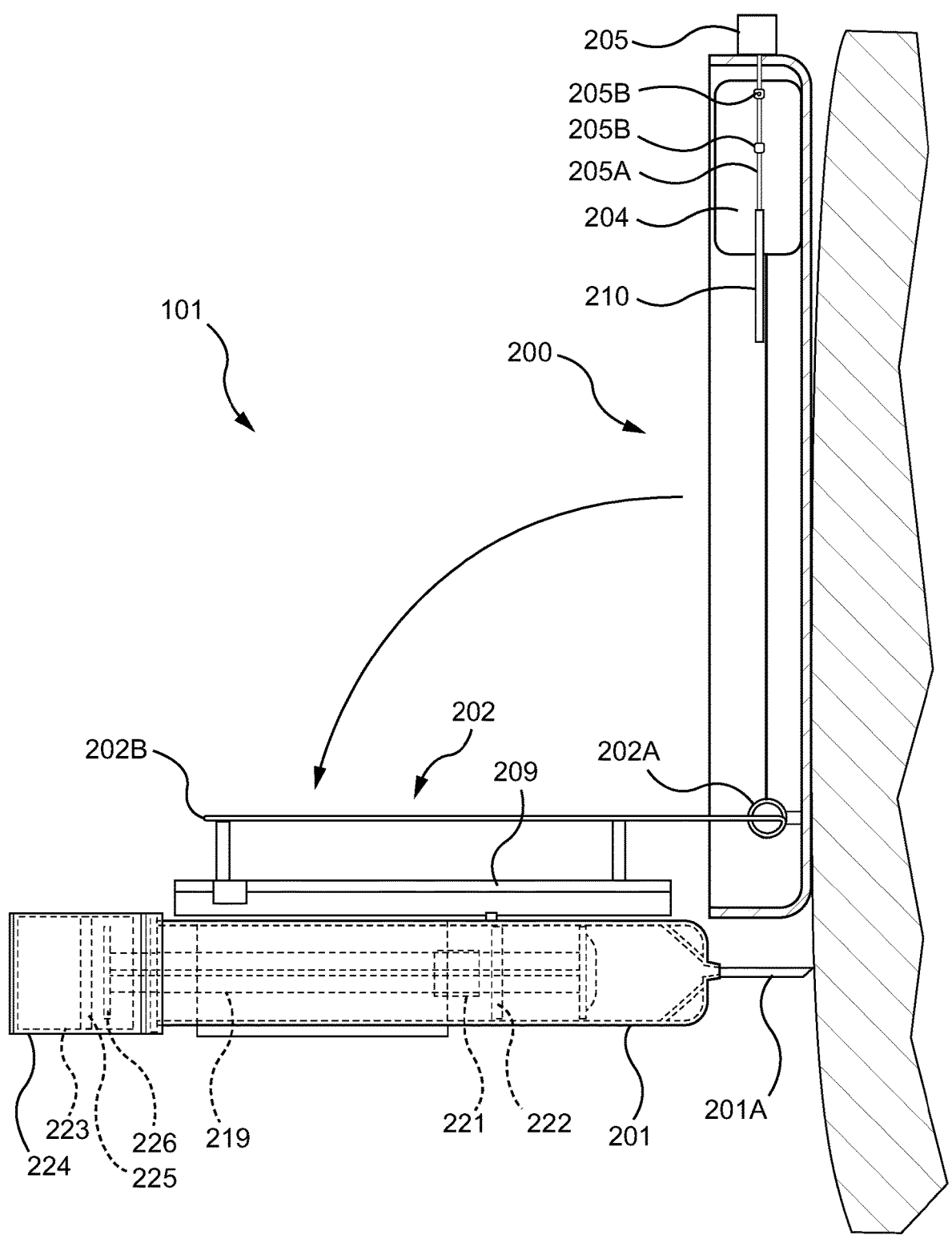
FIG. 6E is a side view of the embodiment of FIG. 6A in an activated state.

When the controller 113 determines that injection of medicine is needed, the controller 113 sends a signal to servo 204 to release the latch 210 so that the biasing mechanism puts the injecting cartridge 400 in a predetermined position as shown in FIG. 6E. The process is as discussed earlier with respect to the embodiment disclosed in FIGS. 5A, 5B, 5C, 5D, 5E, 5F.

Figure 6F:
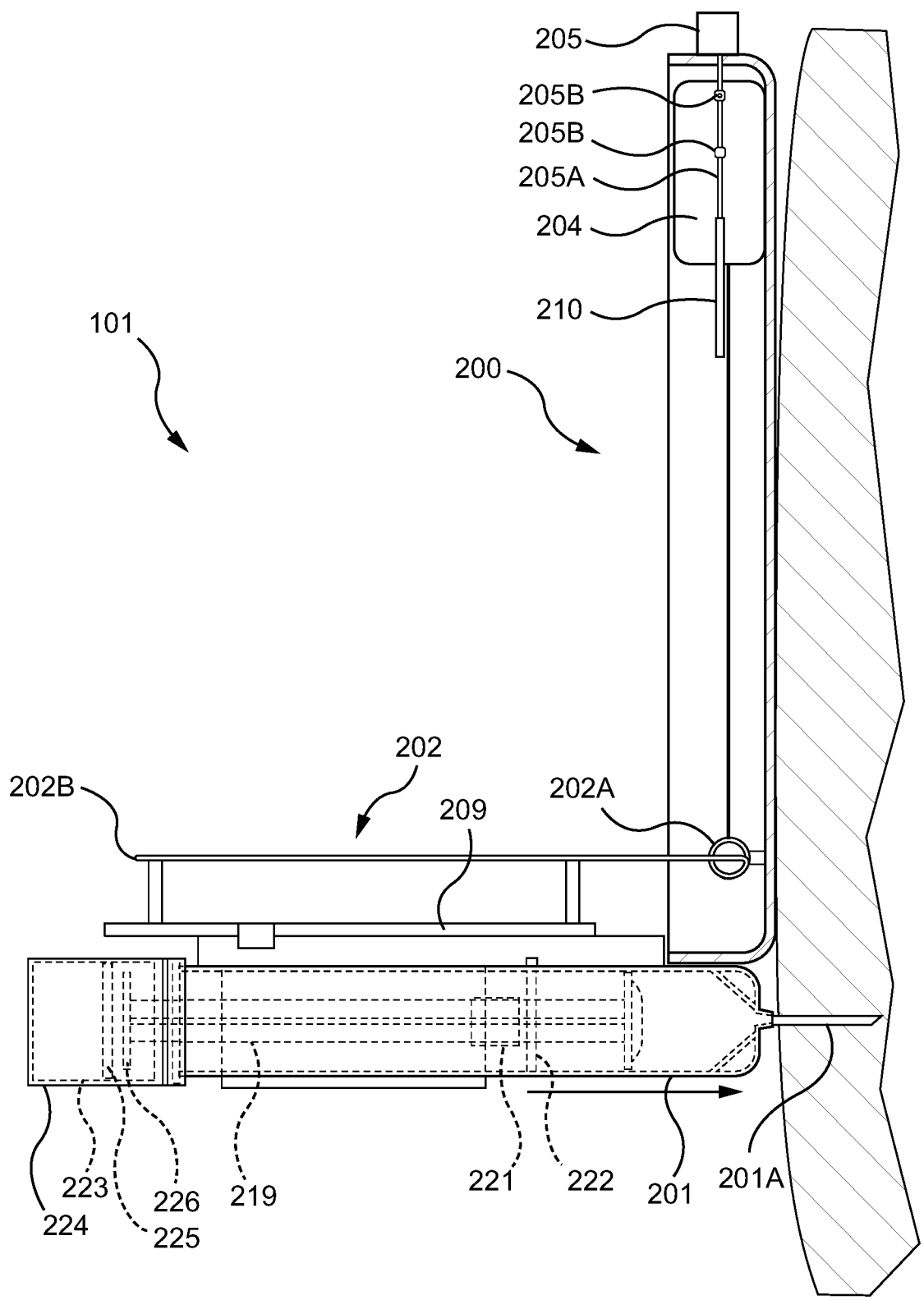
FIG. 6F is a side view of the embodiment of FIG. 6A in a pre-injection state.

After the injecting cartridge 400 is positioned at the predetermined position, the controller 113 sends a signal to the actuators 220 so that the actuator 220 is activated to push the shafts 221 toward the skin of the user so that the syringe 201 moves, such that the needle 201A is inserted into the user's skin as shown in FIG. 6F. The holders 224 and the actuators 223 move simultaneously with the syringe 201 by the connection between the holder 224 and the syringe 201.

Figure 6G:
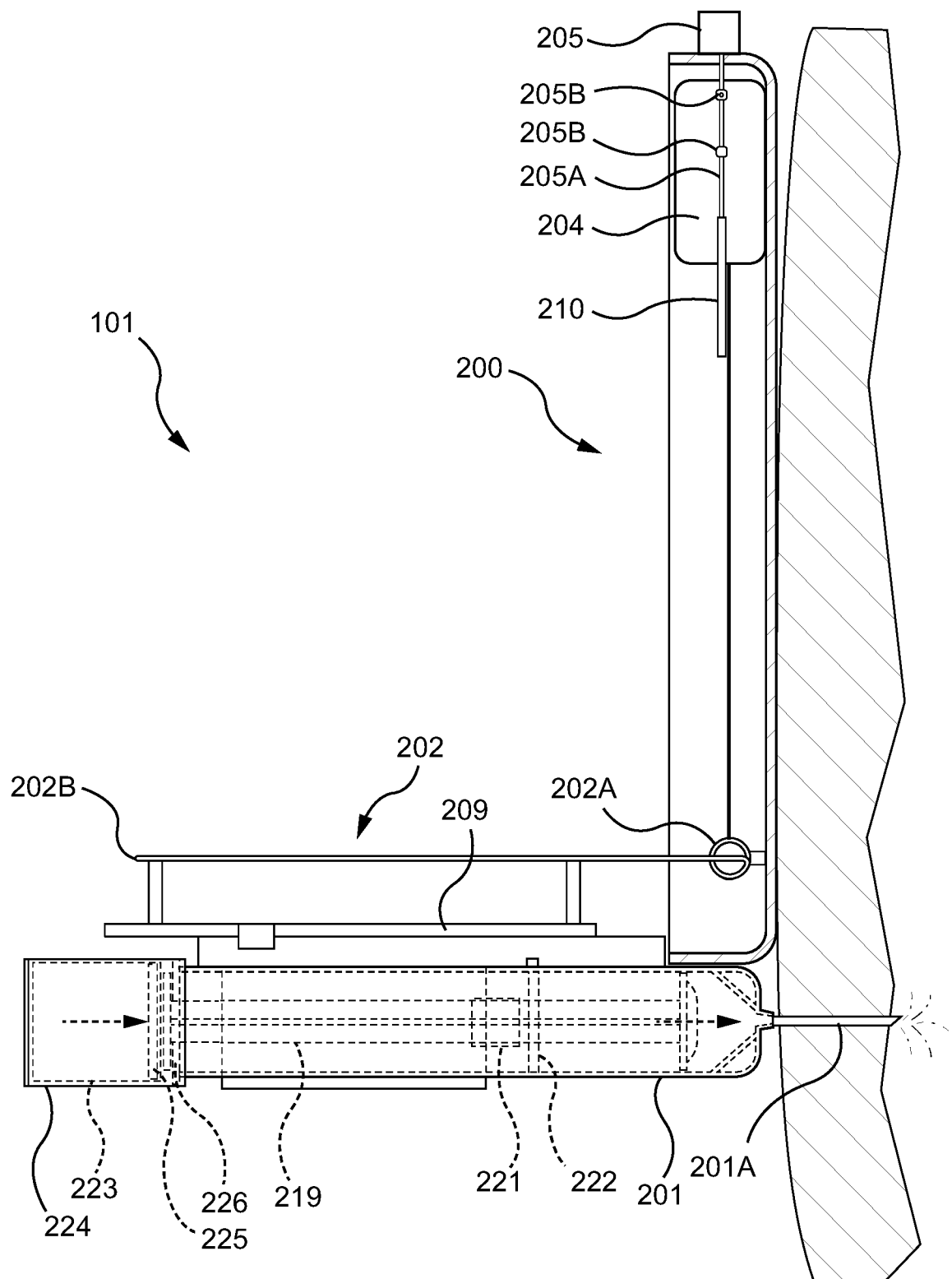
FIG. 6G is a side view of the embodiment of FIG. 6A in an injection state.

When the needle 201A is inserted to the user's skin at a predetermined depth, the controller 113 signals the servos 220 to stop. The controller 113 then signals the servos 223 to push the top 226 of the plunger 219 through the arms 225. Thus, the medicine in the syringe 201 is injected into the user, as shown in FIG. 6G.

In a situation that there is a malfunction in the system 100 such that the medicine cannot be automatically injected, the controller 113 may provide signals indicating the malfunction by audible alarm and/or display on the display unit 104 if the controller 113 is not malfunctioning. The user or caregiver may move the knob 206 to the release position and pull on the knobs 205 to release the biasing mechanism so that the syringe is disposed in a predetermined angle to the skin of the user, as shown in FIG. 6E. In some embodiments, the predetermined angle is substantially perpendicular to the skin of the user (radially inwards into the wearable band 112). The handles 402 may be pulled to engage the connector 222 and pushed toward the skin of the user, causing the connector 222, and in turn the syringe 201 to move toward the user's skin such that the needle 201A is inserted into the user. The bar 404 may be pushed to move the plunger 219 so that the medicine in the syringe 201 is injected into the user when the needle 201A is inserted into the user's body at a predetermined depth. If the controller 113 fails to send signals or if desired, the user or caregiver may use the manual mechanism here to inject the medicine. Depending on the component that is malfunctioning, one or more of these steps can be performed manually. If the controller 113 is malfunctioning, the user may perform these steps manually when desired.

After the injection, the device 101 or the injecting cartridge 400 and the components therein may be disposed of and replaced.

Reference is now made to FIGS. 7A, 7B, 7C, 7D, 7E, 7F and 7G. In this embodiment, the auto-injecting mechanism 231 includes actuators 207 disposed on both sides of the syringe 201. The actuators 207 are connected to conveyors 208 through shafts 217. The syringe 201 is connected to the conveyors 208 by attaching device 229. The syringe 201 may be movably disposed on a rail 209 for smooth and precise movement. In some embodiments, the actuators 207 are servos. The attaching device 229 may include straps.

There are also provided actuators 223 that are fixedly disposed within holders 224. The holders 224 are fixed to an enlarged portion of the syringe 201. The actuators 223 are provided with arms 225 that are disposed above the top 226 of the plunger 219 of the syringe 201. These components are provided in an injecting cartridge 500, as shown in FIG. 7C. The holders 224 and the rail 209 are fixed to the injecting cartridge 500.

Figure 7A:
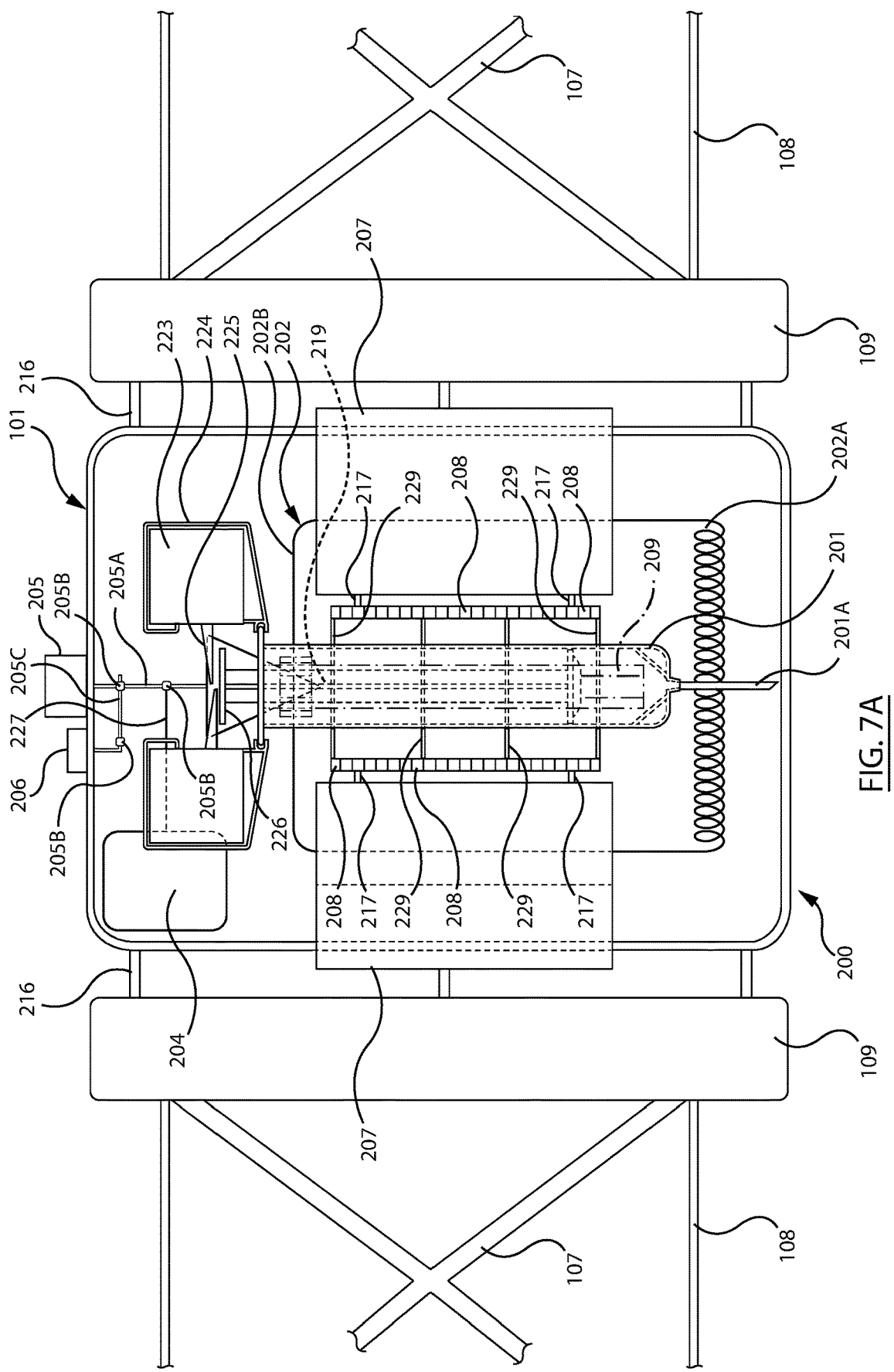
FIG. 7A is the front view of yet another embodiment of the auto-injecting device, showing the internals.
Figure 7B:
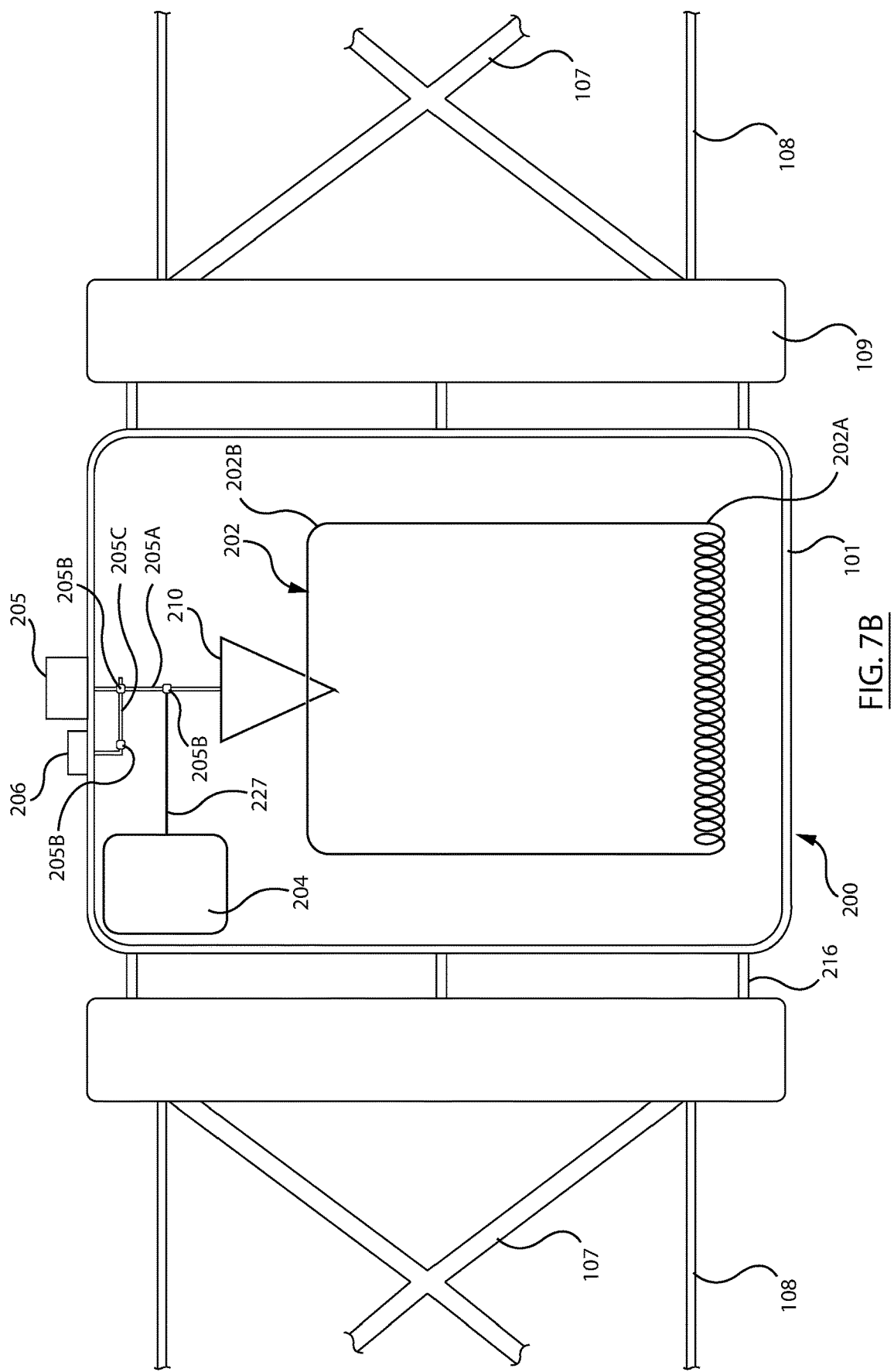
FIG. 7B is the front view of the biasing mechanism of the embodiment of FIG. 7A.
Figure 7C:
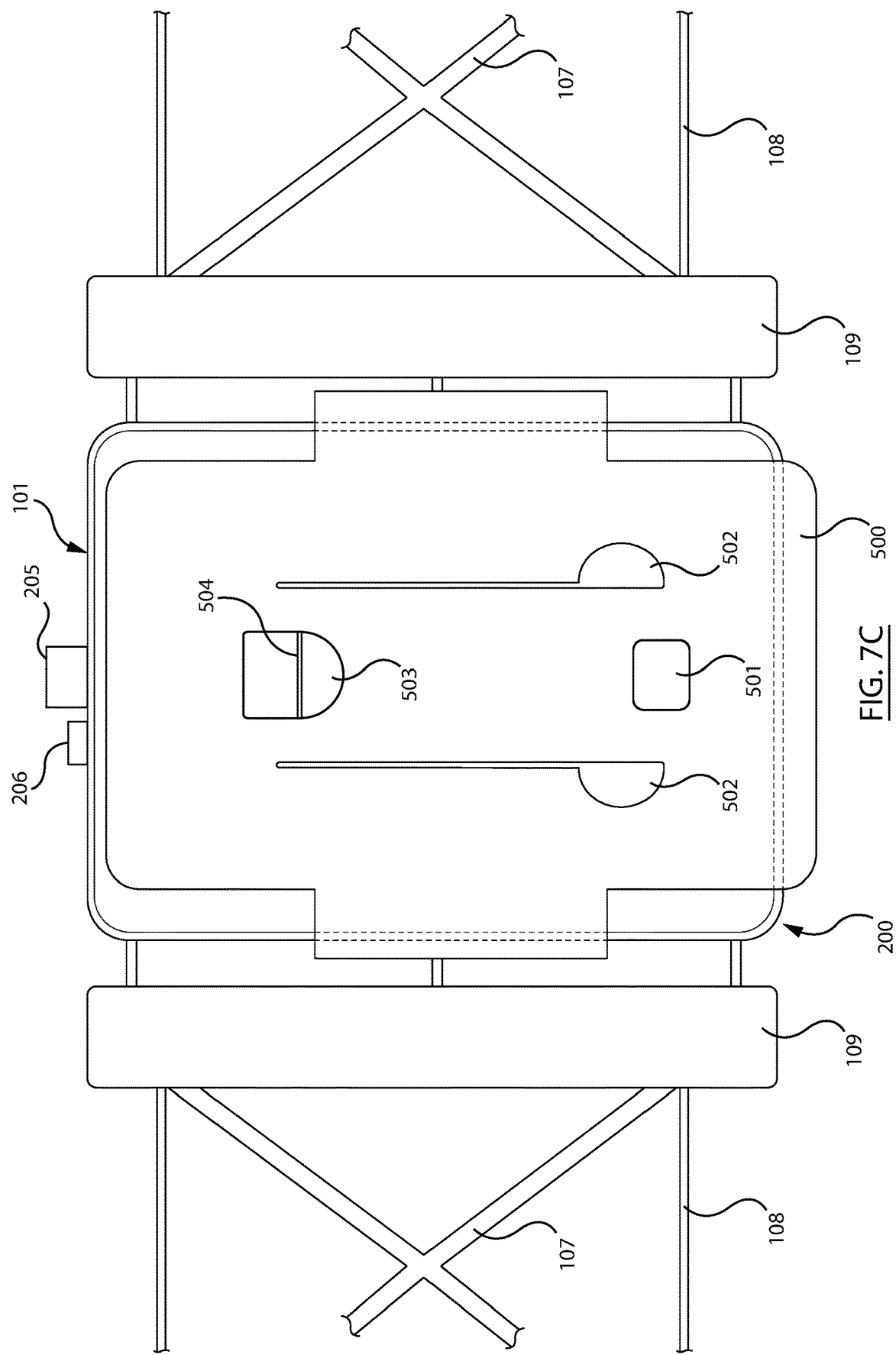
FIG. 7C is a front view of the embodiment of FIG. 7A in a closed position.
Figure 7D:
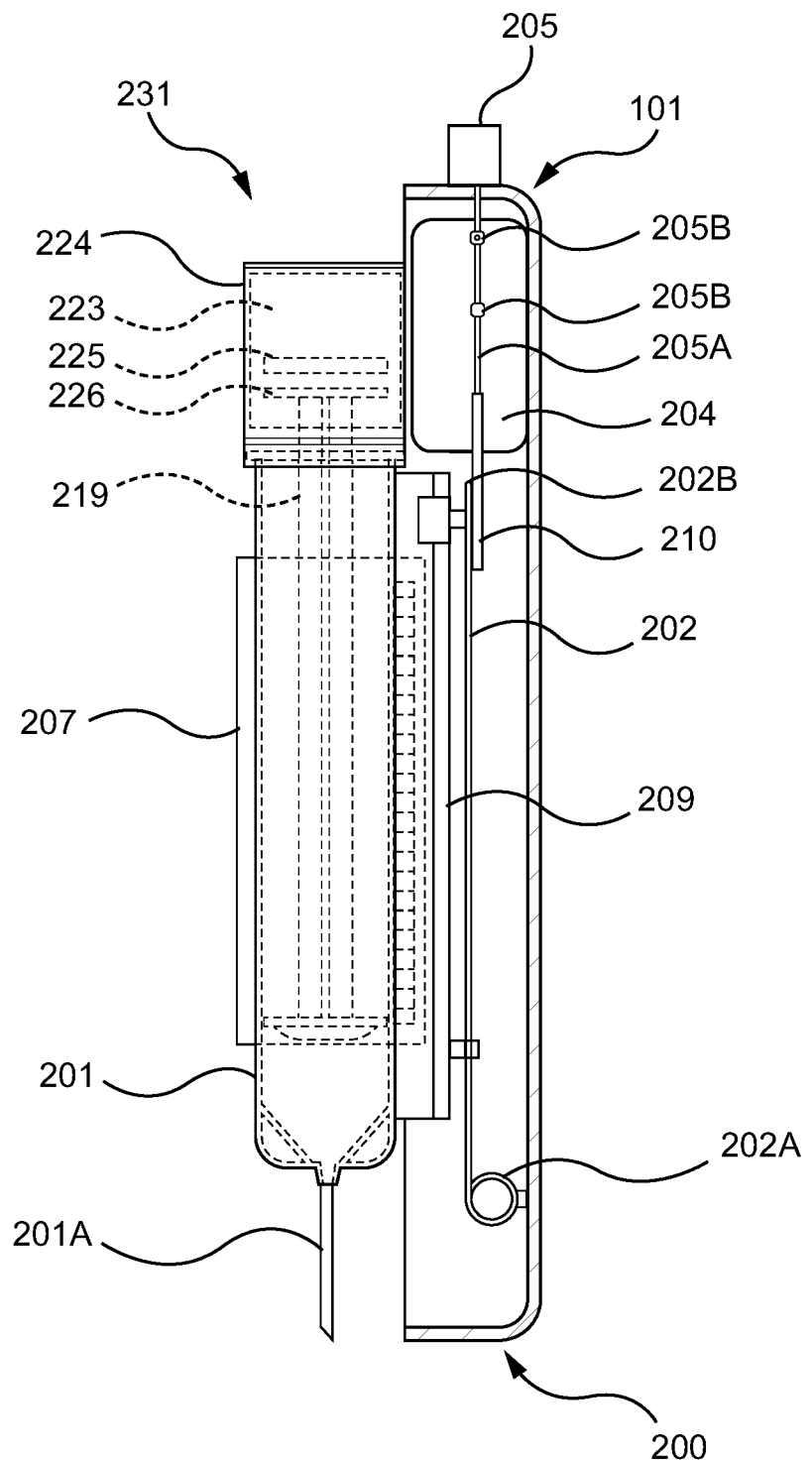
FIG. 7D is a side view of the embodiment of FIG. 7A showing the internals of the embodiment.

A biasing mechanism 202 is also provided, as shown in FIG. 7B. This biasing mechanism 202 is the same as the biasing mechanism 202 in the embodiments of FIGS. 5A, 5B, 5C, 5D, 5E, 5F, 6A, 6B, 6C, 6D, 6E, 6F and 6G. As shown in FIG. 7D, the biasing mechanism 202 is disposed between the syringe 201 and the auto-injecting mechanism 231 and the bottom of the device 101. In some embodiments, the biasing mechanism 202 is disposed between the injecting cartridge 500 and the bottom of the device 101. In some embodiments, the biasing mechanism 202 is disposed between the injecting cartridge 500 and the platform 200.

A window 501 may be configured on the injecting cartridge 500 for viewing the amount of medicine in the syringe 201. Two handles 502 are provided that, when lifted, engage the conveyors 208. Another window 503 is provided on the injecting cartridge 500. A bar 504 is disposed in the window 503. The bar 504 engages the top 226 of the plunger 219 of the syringe 201 when the syringe 201 is moved in position.

Figure 7E:
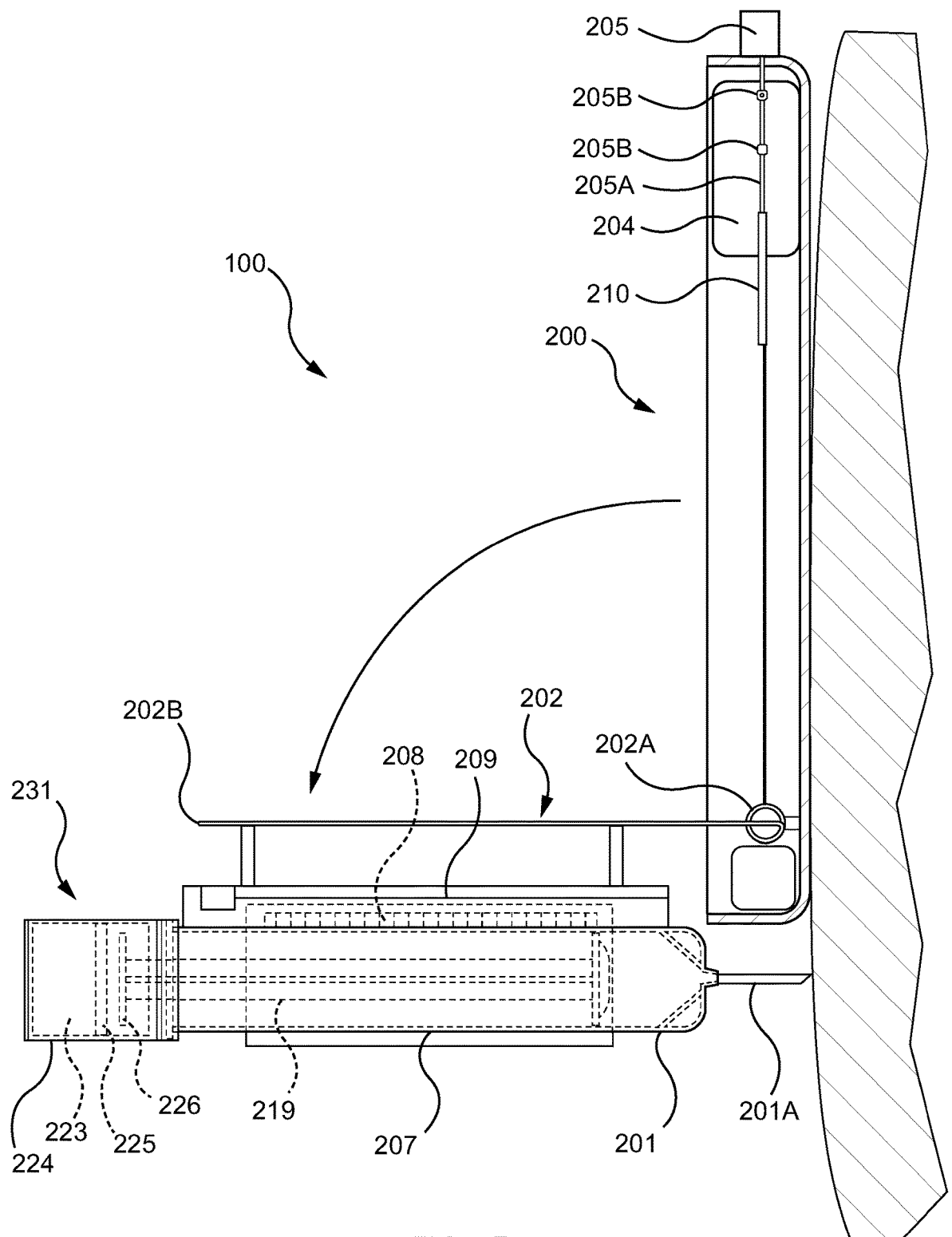
FIG. 7E is a side view of the embodiment of FIG. 7A in an activated state.

When the controller 113 determines that injection of medicine is needed, the controller 113 sends a signal to servo 204 to release the latch 210 so that the biasing mechanism puts the injecting cartridge 500 in a predetermined position as shown in FIG. 7E, wherein the needle 201A is substantially perpendicular to the skin of the user. The process is the same as discussed earlier with respect to the embodiment disclosed in FIGS. 5A, 5B, 5C, 5D, 5E and 5F.

Figure 7F:
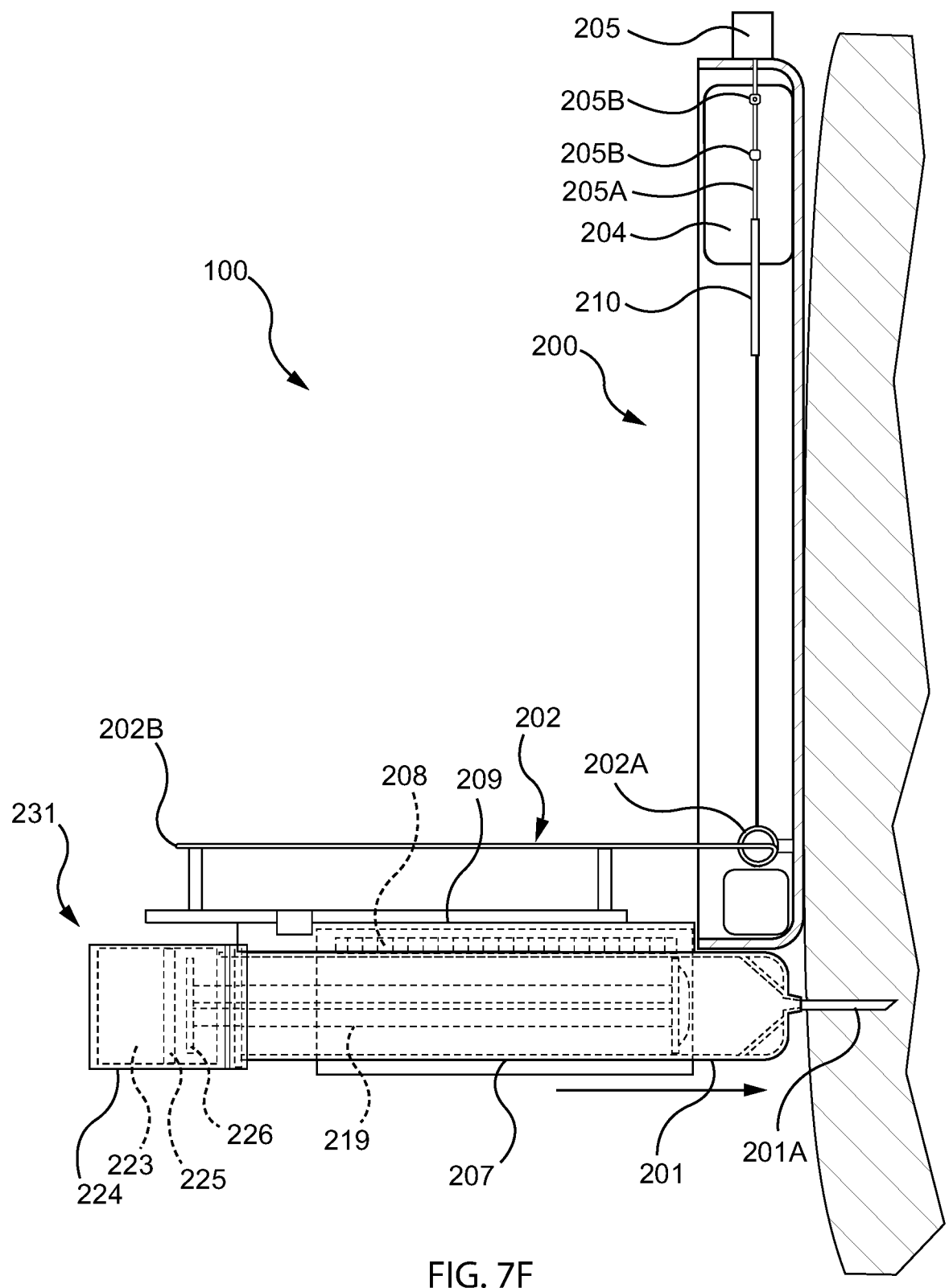
FIG. 7F is a side view of the embodiment of FIG. 7A in a pre-injection state.

After the injecting cartridge 500 is positioned at the predetermined position, the controller 113 sends a signal to the actuators 207 to move the shafts 217 toward the skin of the user, pulling the conveyors 208 along, which in turn causes the syringe 201 to move along the rail 209 toward the skin of the user. As a result, the needle 201A is inserted through the skin of the user, as shown in FIG. 7F.

Figure 7G:
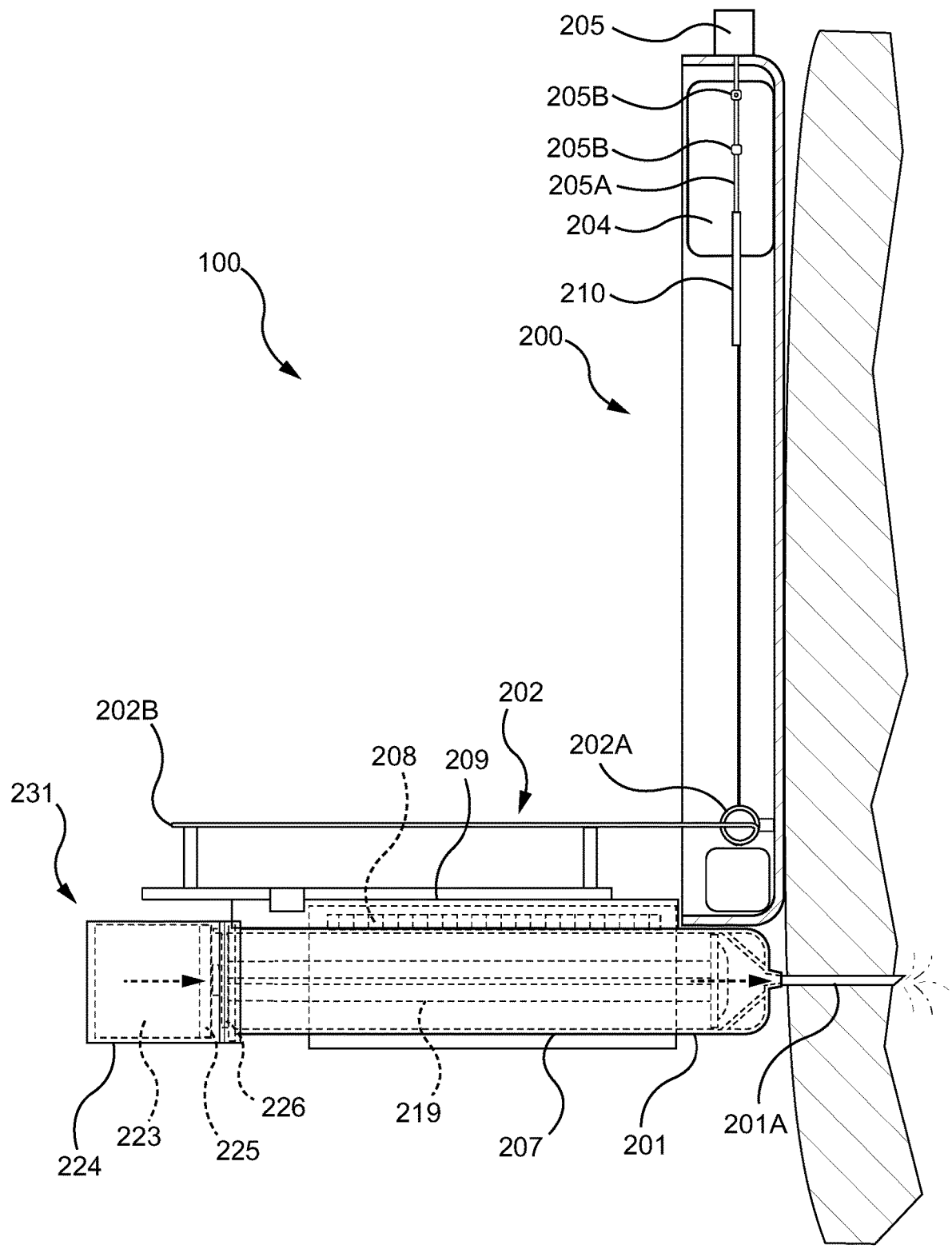
FIG. 7G is a side view of the embodiment of FIG. 7A in an injection state.

When the needle 201A is inserted to a predetermined depth into the user, the controller 113 signals the actuators 207 to stop and then signals the actuators 223 to push the arms 225 towards the user. The arms 225 then push the top 226 of the plunger 219, injecting the medicine in the syringe into the user, as shown in FIG. 7G.

In a situation that there is a malfunction in the system such that the medicine cannot be automatically injected, the controller 113 may provide signals indicating the malfunction by audible alarm and/or display on the display unit 104 if the controller 113 is not malfunctioning. Upon the alarm or if the user so desires, the user can manually release the biasing mechanism 202 as described earlier, such that the injecting cartridge 500 is in the injecting position. The user or the caregiver may pull up the handles 502 to engage the conveyors 208, then the handles 502 may be pushed toward the skin of the user such that the syringe 201 moves toward the skin of the user. After the needle 201A is inserted into the user at a predetermined depth, the bar 504 may be pushed toward the skin of the user so that the plunger 219 of the syringe 201 is pushed, resulting in injection of the medicine into the user. Depending on the component that is malfunctioning, one or more of these steps can be performed manually. Regardless whether the controller 113 is malfunctioning, the user may perform these steps manually if desired.

After the injection, the device 101 or the injecting cartridge 500 may be disposed of and replaced.

Figures 8A, 8B:
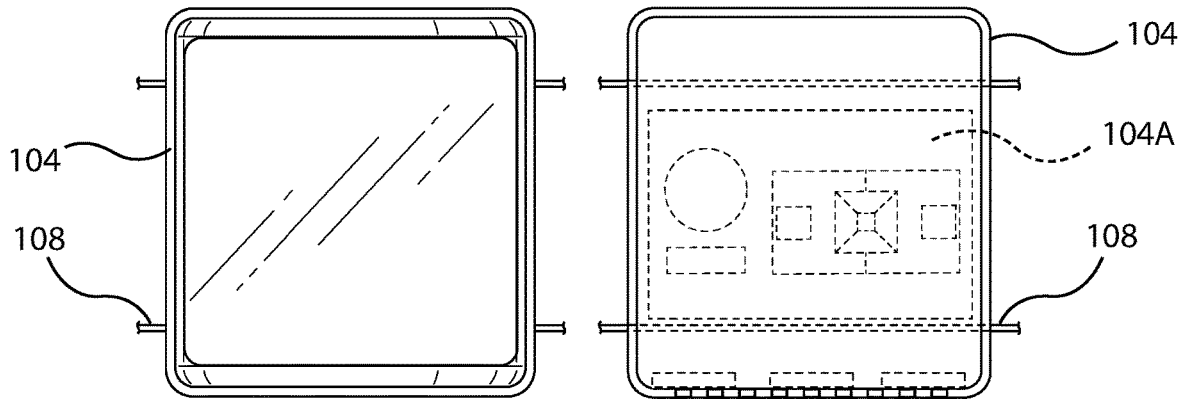
FIGS. 8A and 8B show the front view and the internals of a display unit of the system.

FIGS. 8A and 8B show the display unit 104, which may be an LCD display or LED display, and contain the display component 104A.

FIGS. 9A and 9B show the battery unit 105 that provides power to the system. There may be one single battery or multiple batteries. The batteries 105 may be integrated with the various components of the system 100. The batteries 105 may be rechargeable, and the system 100 may include power input interfaces for charging the batteries 105 or providing power to the system. There may also be provided solar cells for powering the system 100. A kinetic charger may be included in the system 100 for generating electricity by movement of the user to recharge the battery unit 105.

FIGS. 10A and 10B show the oxygen ($O^2$) sensor 102, infrared (IR) sensor unit 106, and heart rate (HR) monitor unit 103. These sensors may be provided in separated components or be integrated in a sensor unit.

In some examples, the system 100 can be used to inject substances other than medicine. Example substances include vaccines, vitamins, insulin, with modification as appropriate.

Reference is now made to FIGS. 12-15, which shows a system 100 comprising two wearable bands 100A and 100B, in accordance with an example embodiment.

Figure 12:
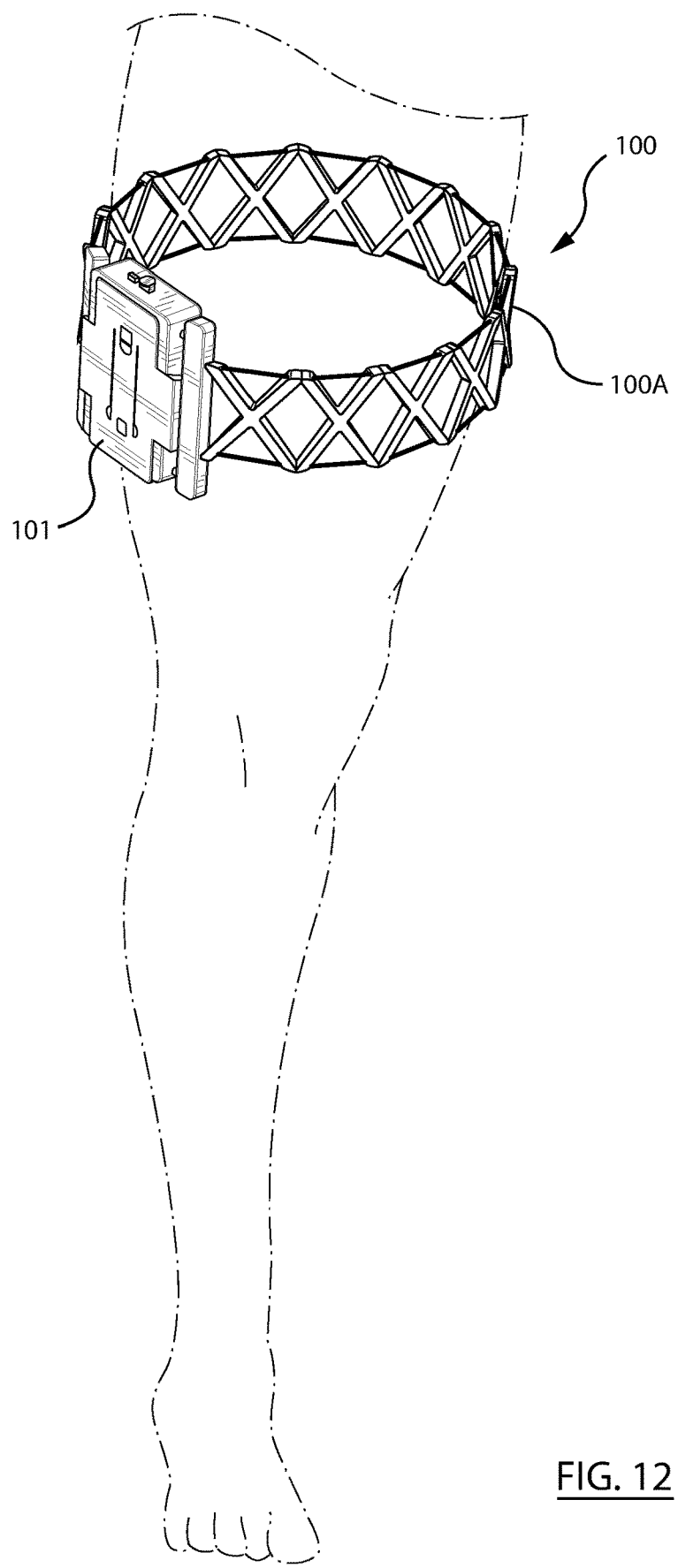
FIG. 12 is a perspective view of a first wearable band, attached to a user's leg, of a system in accordance with another embodiment.
Figure 13:
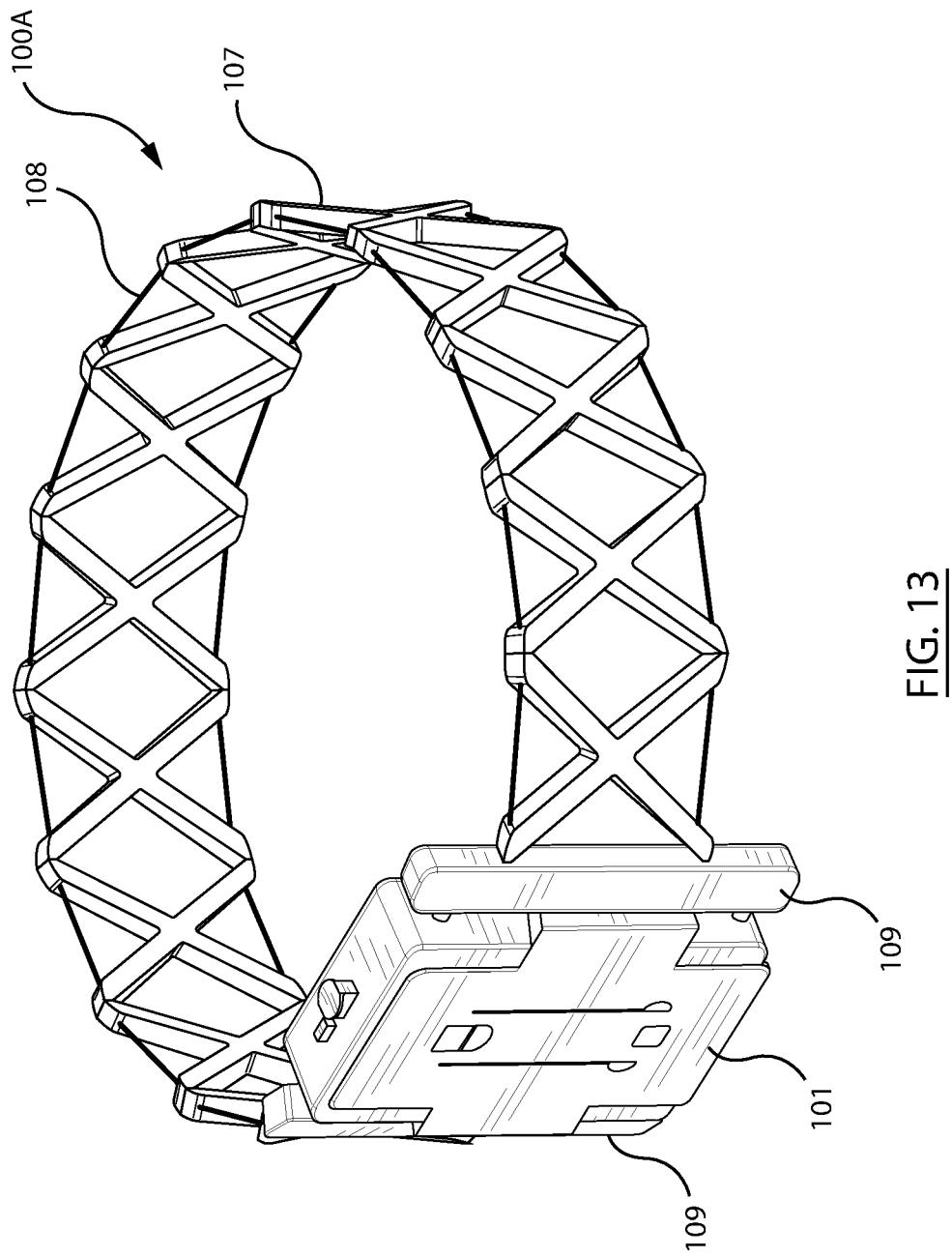
FIG. 13 is a perspective view of the first wearable band of FIG. 12.
Figure 14:
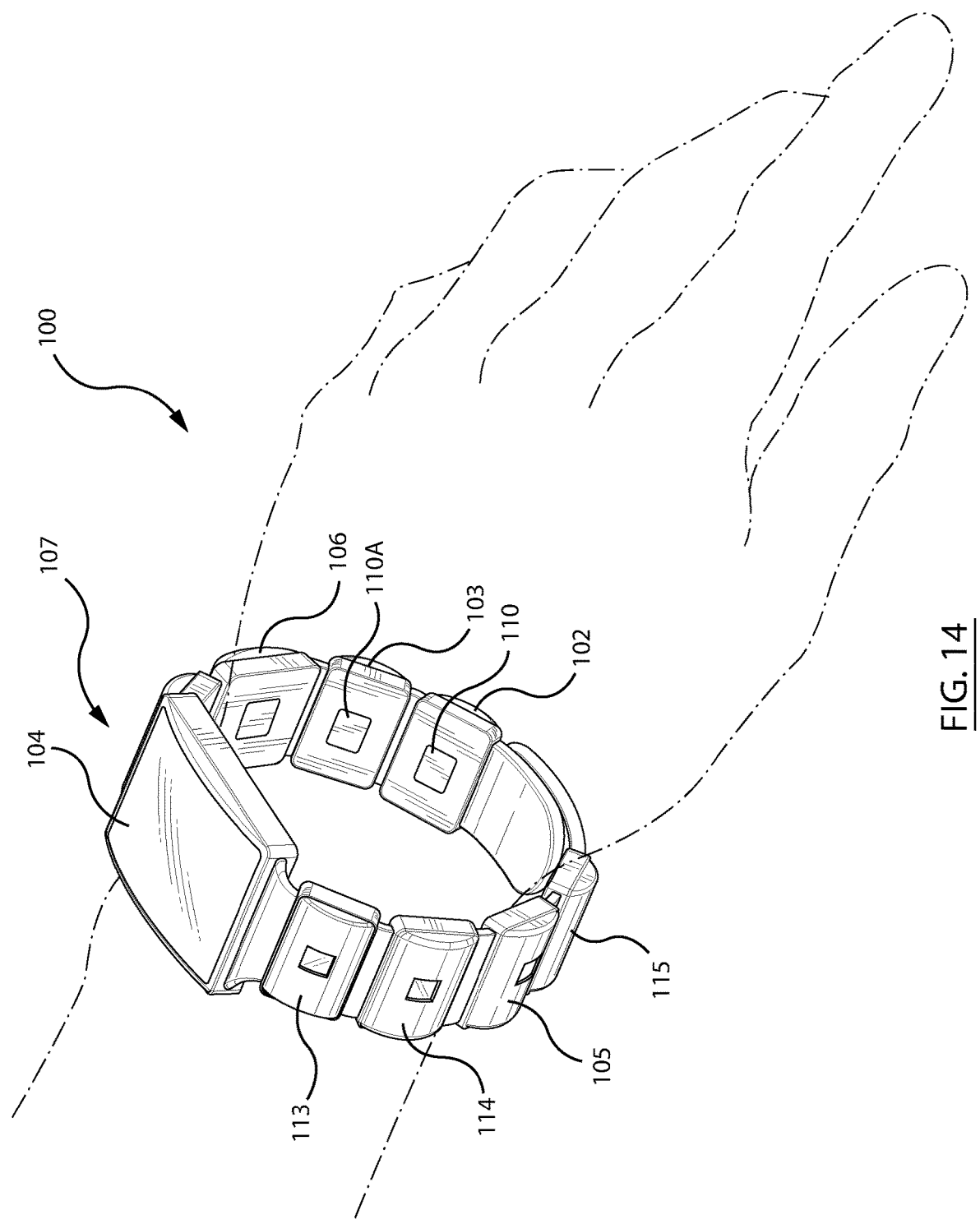
FIG. 14 is a perspective view of a second wearable band of the system of the embodiment referred to with respect to FIG. 12, attached to a user s arm.
Figure 15:
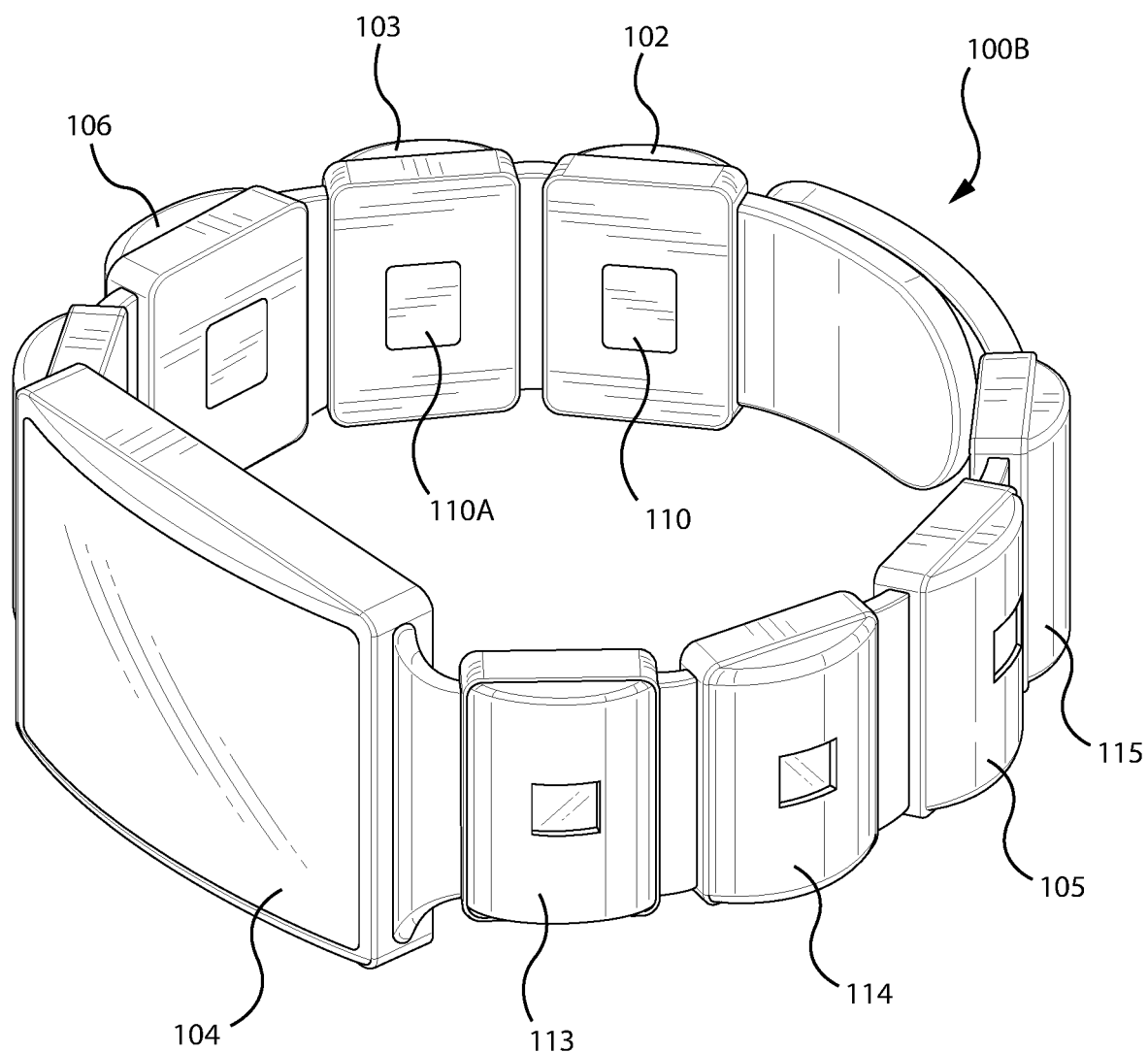
FIG. 15 is a perspective view of the second wearable band of FIG. 14.
Figure 16:
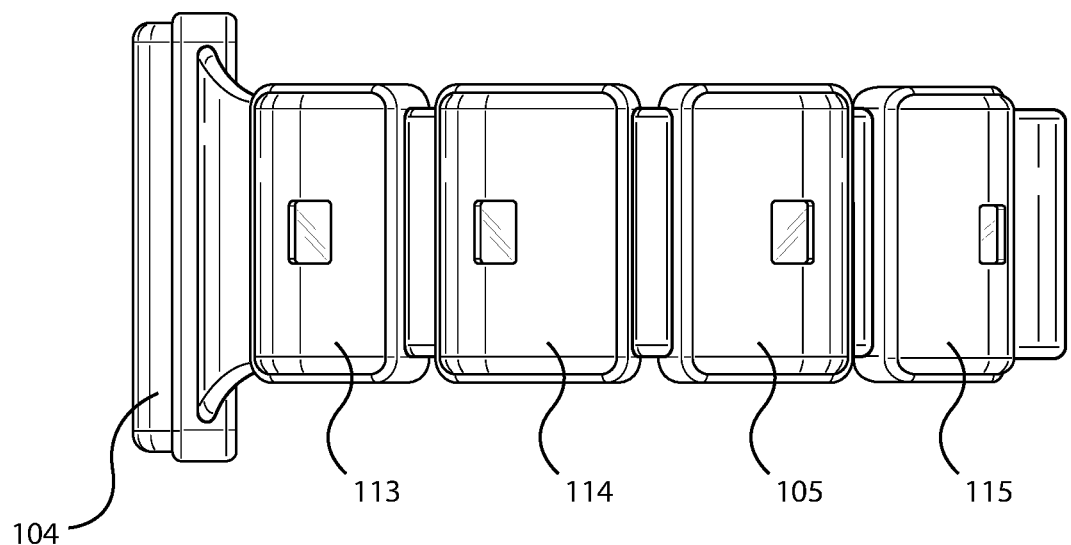
FIG. 16 is a right side view of the second wearable band of FIG. 14.
Figure 17:
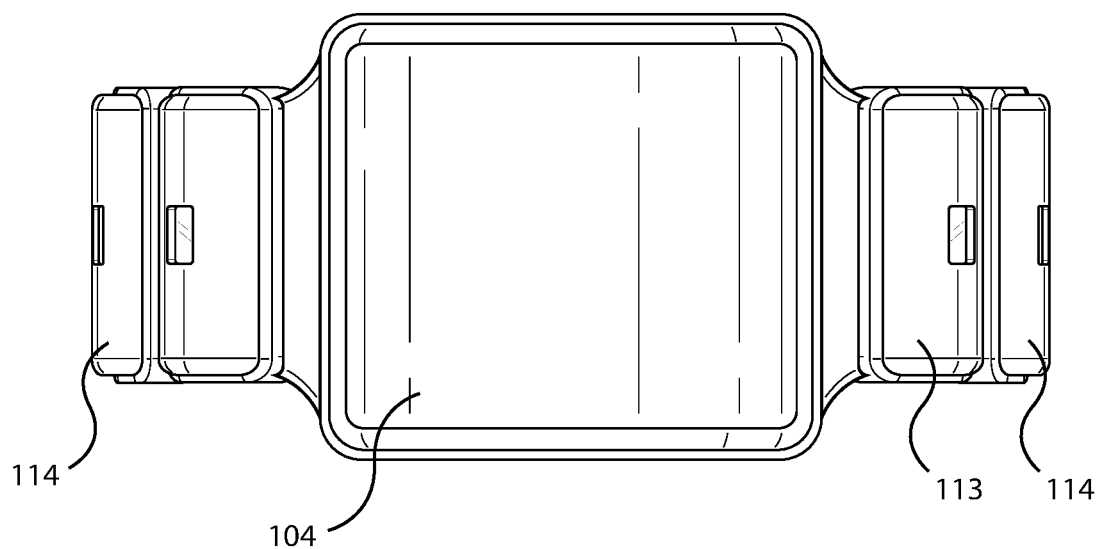
FIG. 17 is a front view of the second wearable band of FIG. 14.
Figure 18:
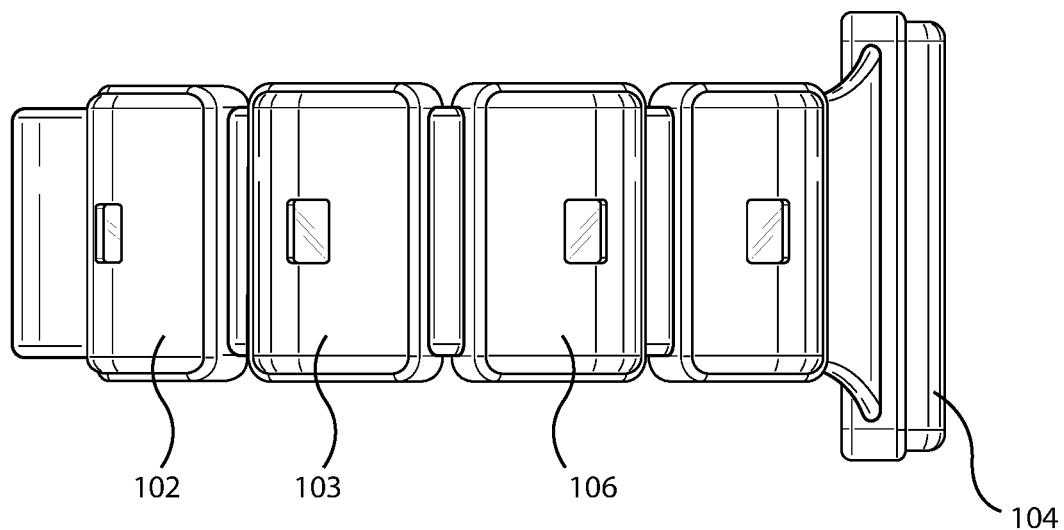
FIG. 18 is a left side view of the second wearable band of FIG. 14.
Figure 19:
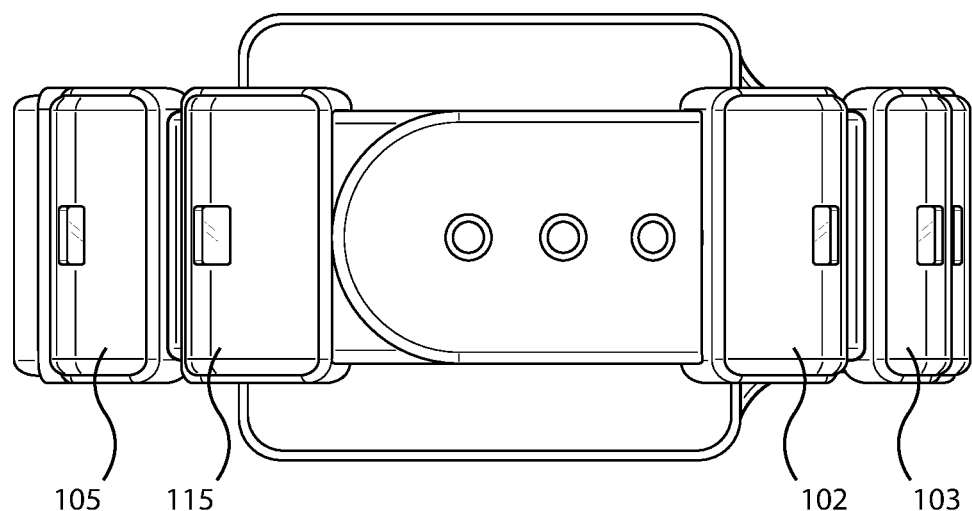
FIG. 19 is a back side view of the second wearable band of FIG. 14.
Figure 20:
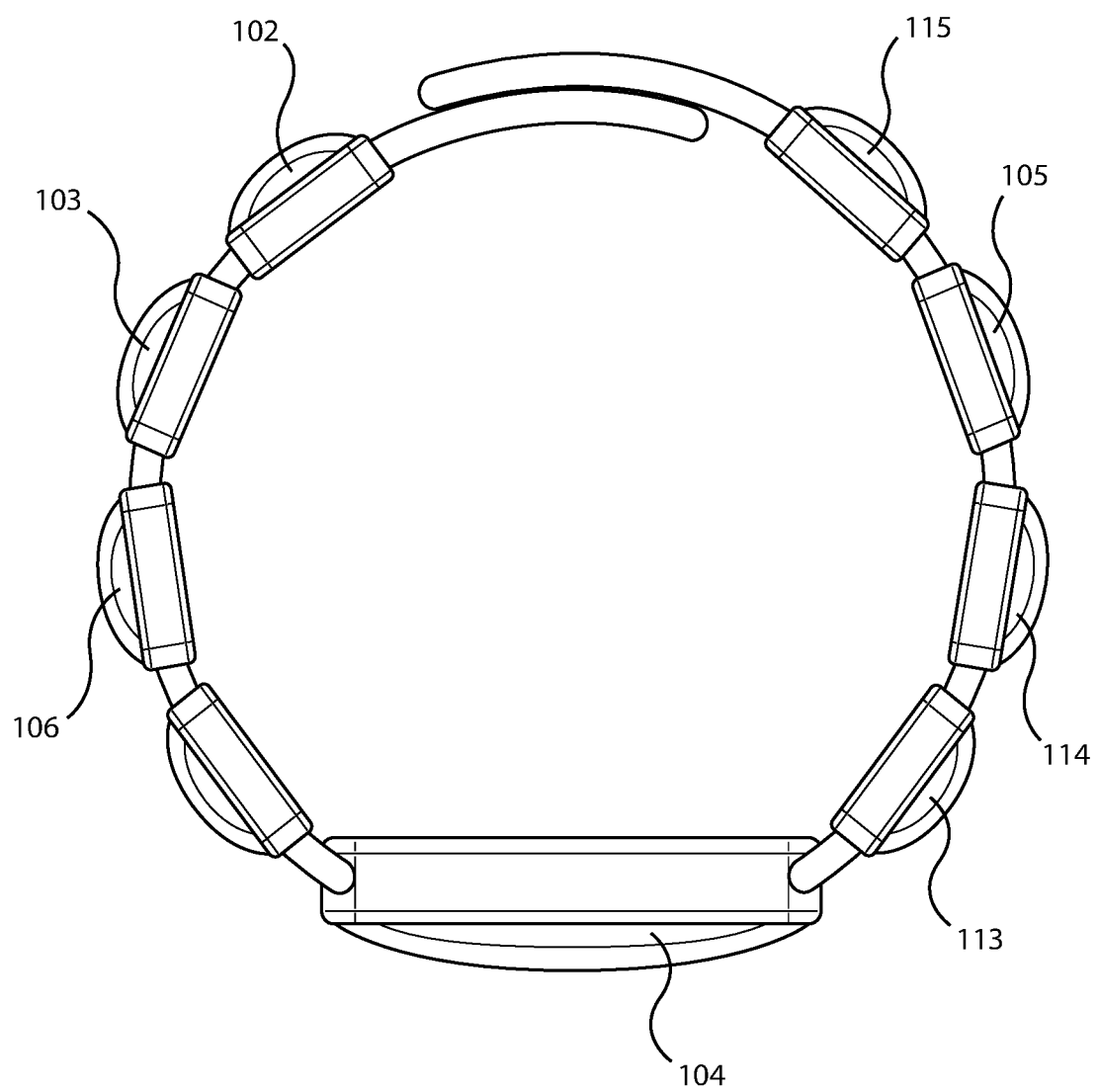
FIG. 20 is a top view of the second wearable band of FIG. 14.
Figure 21:
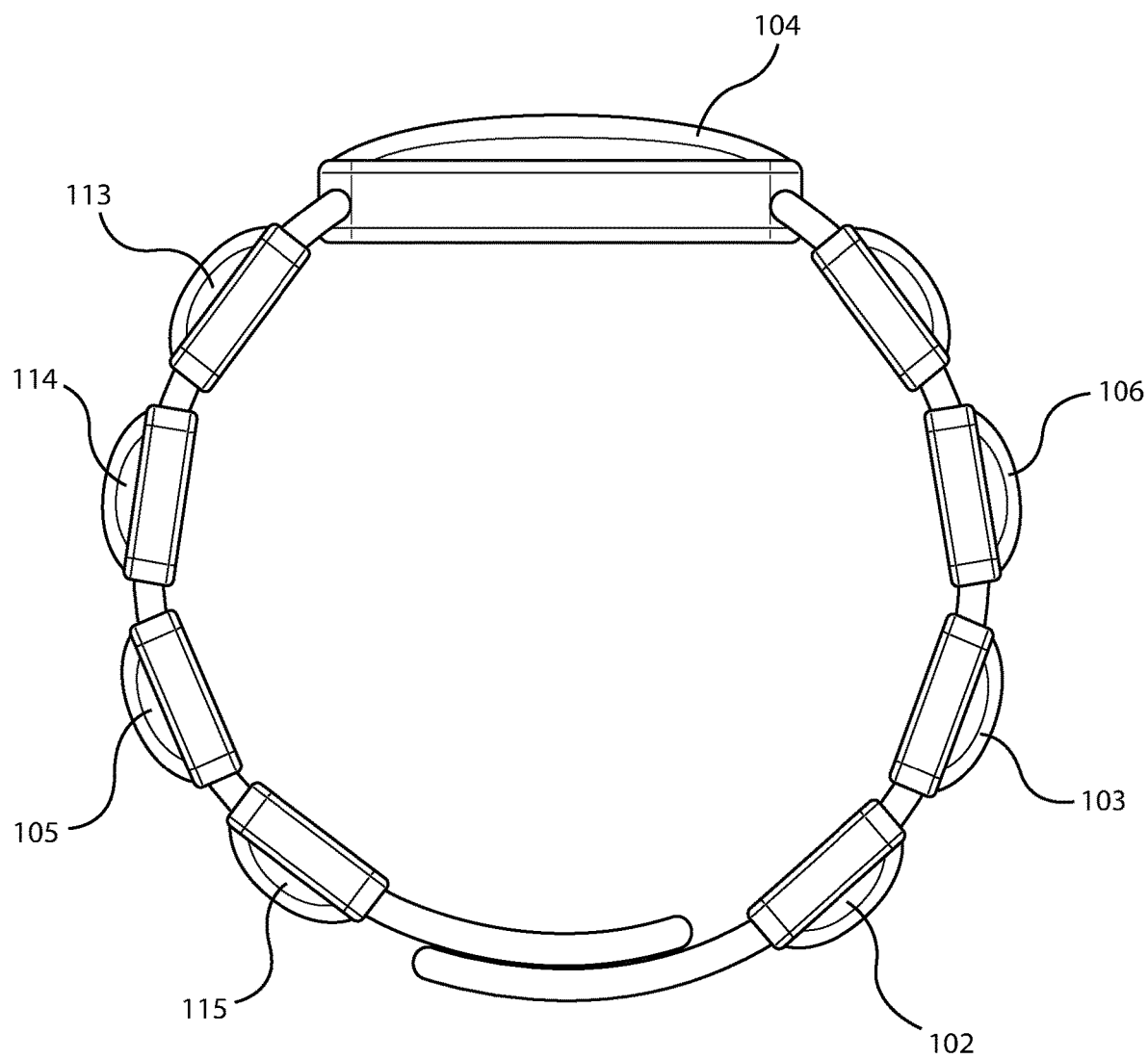
FIG. 21 is a bottom view of the second wearable band of FIG. 14.
Figure 22:
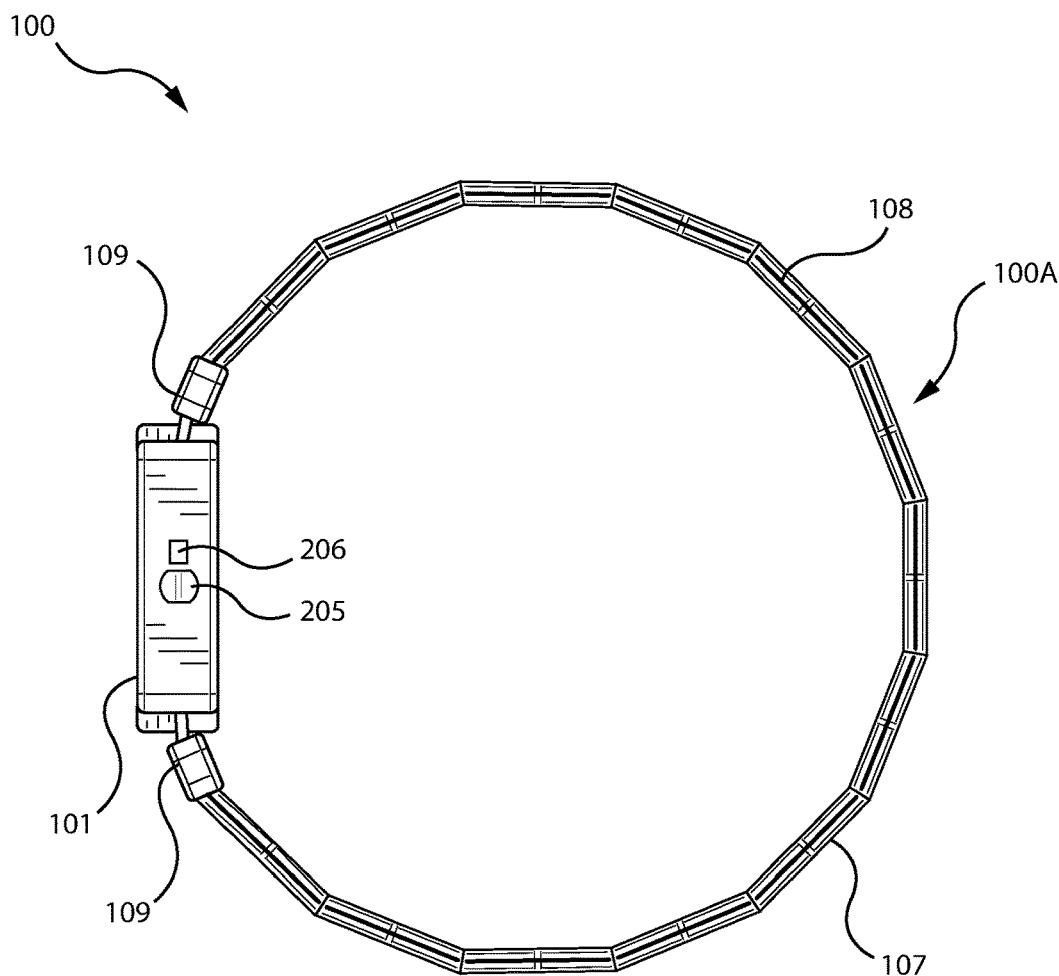
FIG. 22 is a top view of the first wearable band of FIG. 12.
Figure 23:
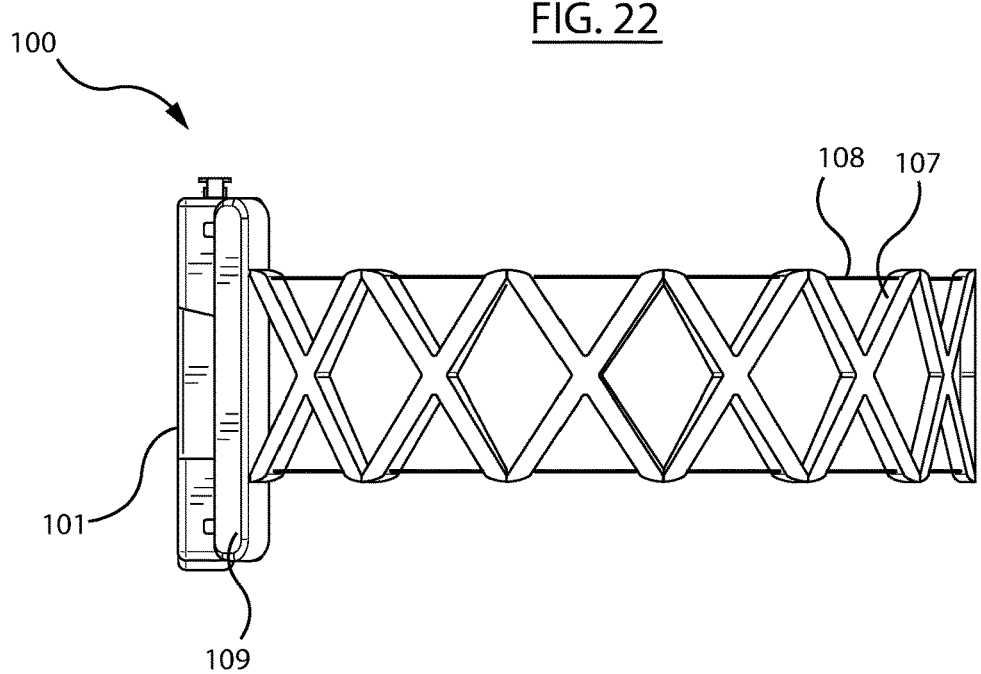
FIG. 23 is a right side view of the first wearable band of FIG. 12.
Figure 24:
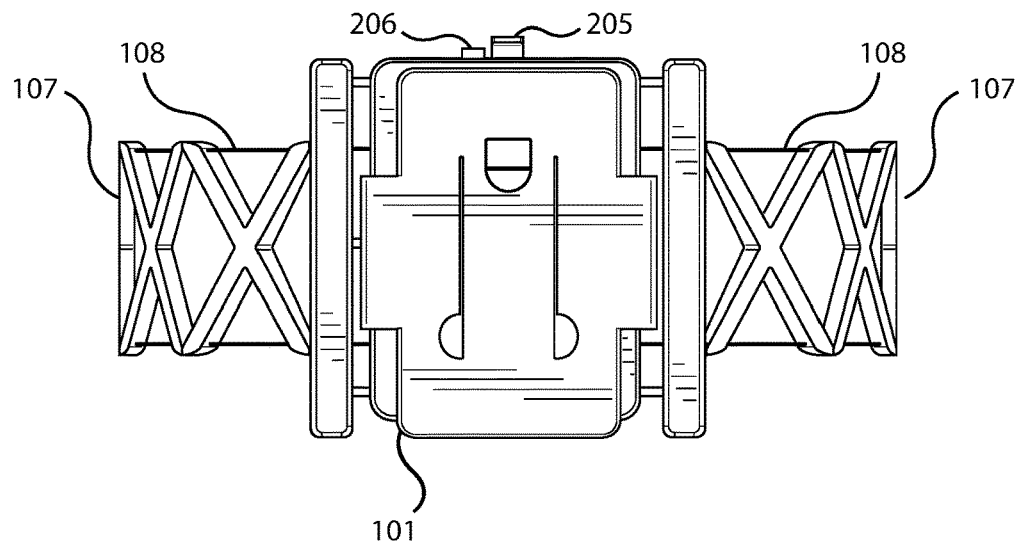
FIG. 24 is a front view of the first wearable band of FIG. 12.
Figure 25:
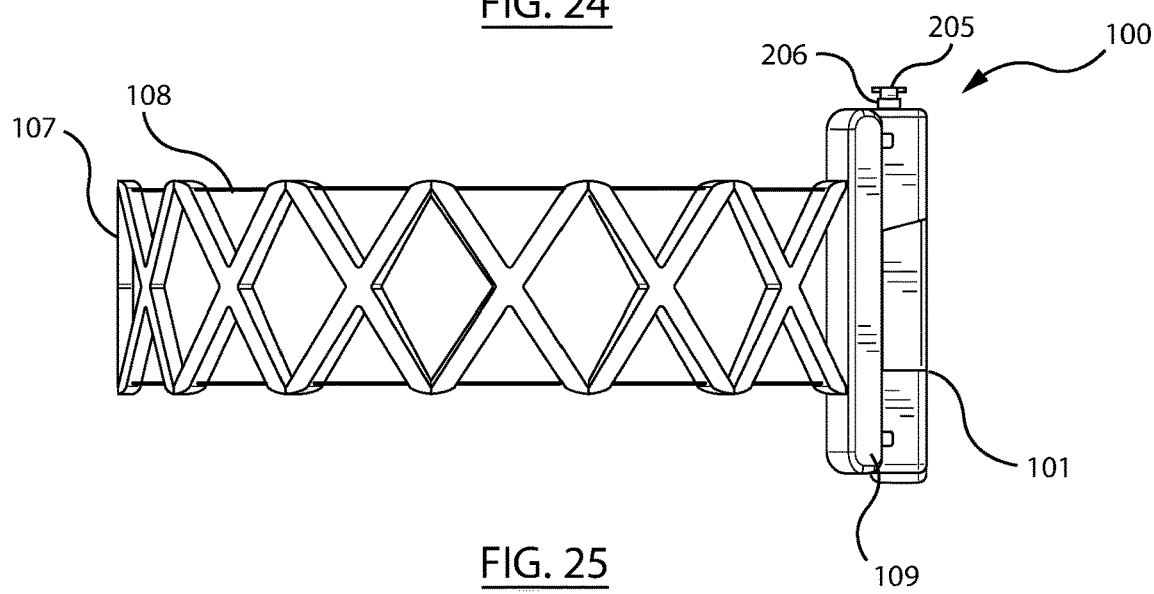
FIG. 25 is a left side view of the first wearable band of FIG. 12.
Figure 26:
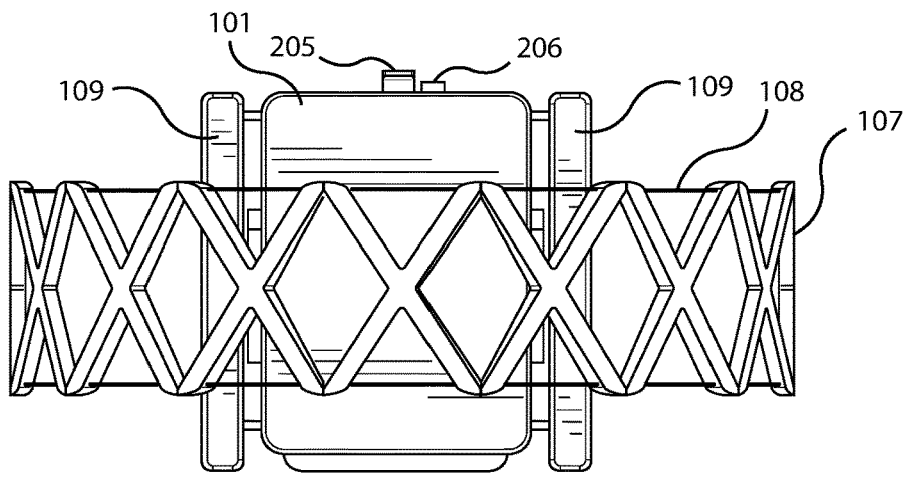
FIG. 26 is a back side view of the first wearable band of FIG. 12.

FIGS. 12 and 13 show the first wearable band 100A, which includes resilient crosslinks 107 and the strings 108 are retractable strings that are disposed between the wires activating component 109. The resilient crosslinks 107 may be made of rubber or thermoplastic elastomers (TPE). In some embodiments, the crosslinks 107 are strong and flexible. For example, the crosslinks 107 can be made of composite material.

The crosslinks 107, strings 108, and the wire activating component 109 can be configured as described earlier.

FIGS. 14-21 show the second wearable band 100B, which includes one or more sensors, for example, one or more blood oxygen sensor unit 102, heart rate (HR) monitor unit 103, IR sensor unit 106, and blood pressure sensor unit 114 as described earlier. The second wearable band 100B may also include display unit 104, battery unit 105, and controller 113. In some embodiments, the display unit 104 is the display of a smartwatch, for example, apple watch or google smartwatches. In some embodiments, the controller is integrated in the smartwatch, for example, in the form of an app running on the watch.

In some embodiments, a wireless communication is established between the two wearable bands 100A and 100B such that the controller 113 can control the function of the first wearable band 100A, for example, tightening of the first wearable band 100A or injecting using the auto-injecting device 101. The detailed operation of the controller 113 controlling the strings 108, the wire activating component 109, and the operation of the auto-injecting device 101 are as described above.

FIGS. 22-26 show different views of the first wearable band 100A.

Figure 27:
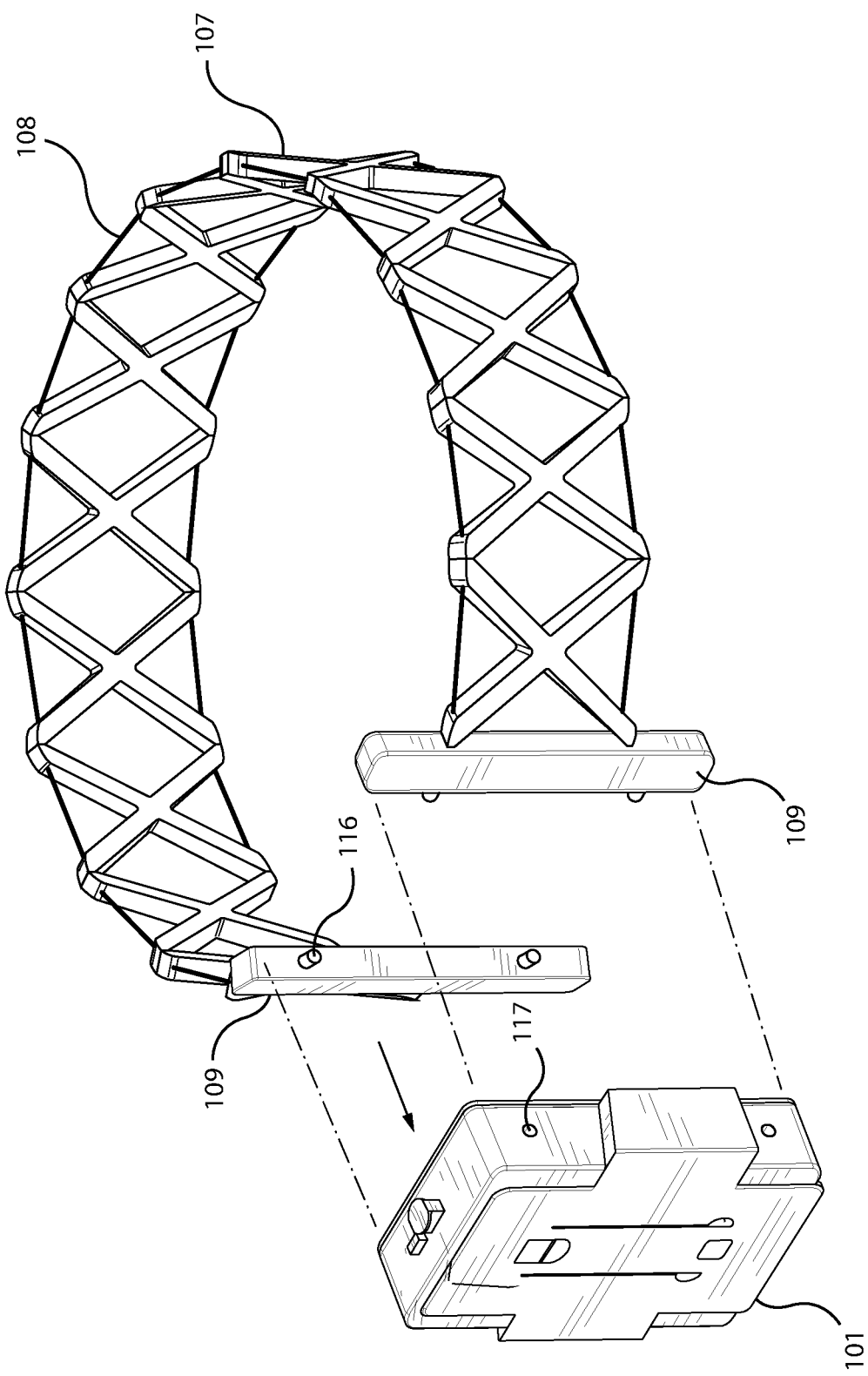
FIG. 27 is an extended view of the first wearable band of FIG. 12, in which the auto-injecting device is detached from the band.
Figure 28C:
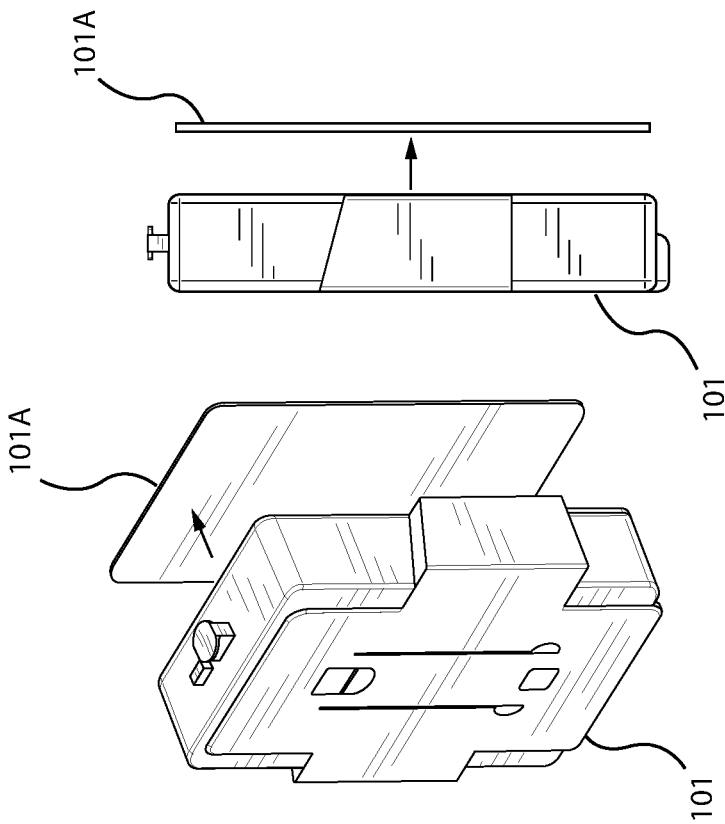
FIG. 28C is a perspective exploded view of the device of FIG. 28A.
Figure 28A:
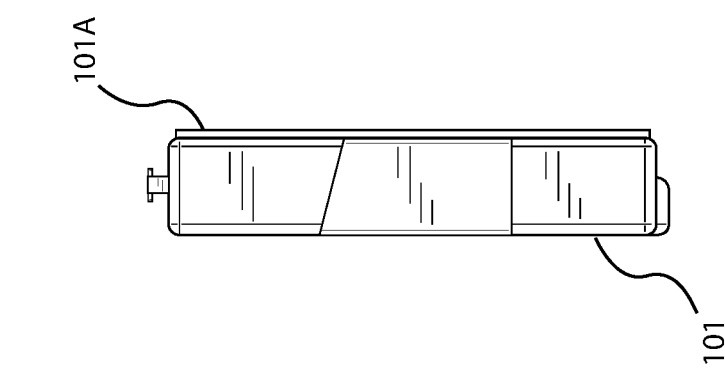
FIG. 28A is a perspective view of the auto-injecting device, in accordance with another embodiment.
Figure 28A:
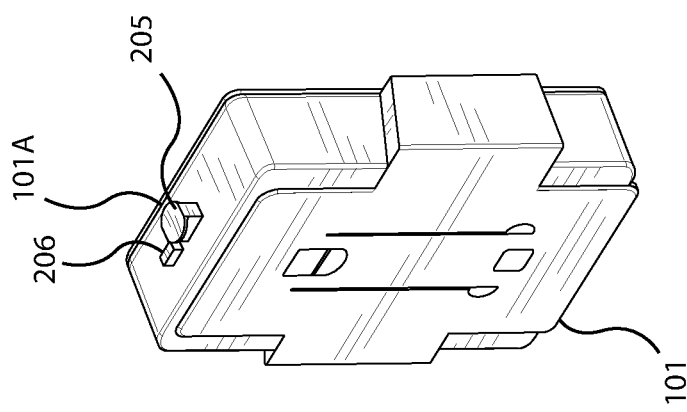

As shown in FIG. 27, in some embodiments, the auto-injecting device 101 is removably attached to the wire activating component 109. In some embodiments, the auto-injecting device 101 is attached to the wire activating component 109 by pins 116 and recesses 117 that receive the pins 116. The pins 116 may have enlarged portion for more secure attachment. In some embodiments, the auto-injecting device 101 is attached to the wire activating component 109 by a protrusion/groove system. The auto-injecting device 101 can be attached to the wire activating component 109, the strings 108, or the crosslinks 107 by other suitable attaching mechanisms.

FIGS. 28A, 28B, 28C, and 28D show a different embodiment of the auto-injecting device 101. An additional component 101A is provided which is configured to operatively attach to the auto-injecting device 101 through the clothing of a user, such that the auto-injecting device 101 can be attached to the clothing of the user without requiring a wearable band as described above.

In some embodiments, the back side of the auto-injecting device 101 and the component 101A are configured such that the back side of the auto-injecting device 101 is magnetically attracted to the component 101 such that the auto-injecting device 101 can be attached to the user's clothing without requiring the wearable band as described above. In some embodiments, the backside of the auto-injecting device 101 and the component 101A are configured with corresponding pins and recesses, wherein the pins can poke through the clothing, such that the auto-injecting device 101 can be attached to the clothing of the user. In some embodiments, the component 101A is a sheet of magnetic or ferromagnetic material. The auto-injecting device 101 includes a sheet of magnetic or ferromagnetic material. In some embodiments, the component 101A conforms to the body part that it is disposed adjacent to. In some embodiments, the component 101A may be flexible such that it can conform to the body part that is disposed adjacent to.

Figure 29A:
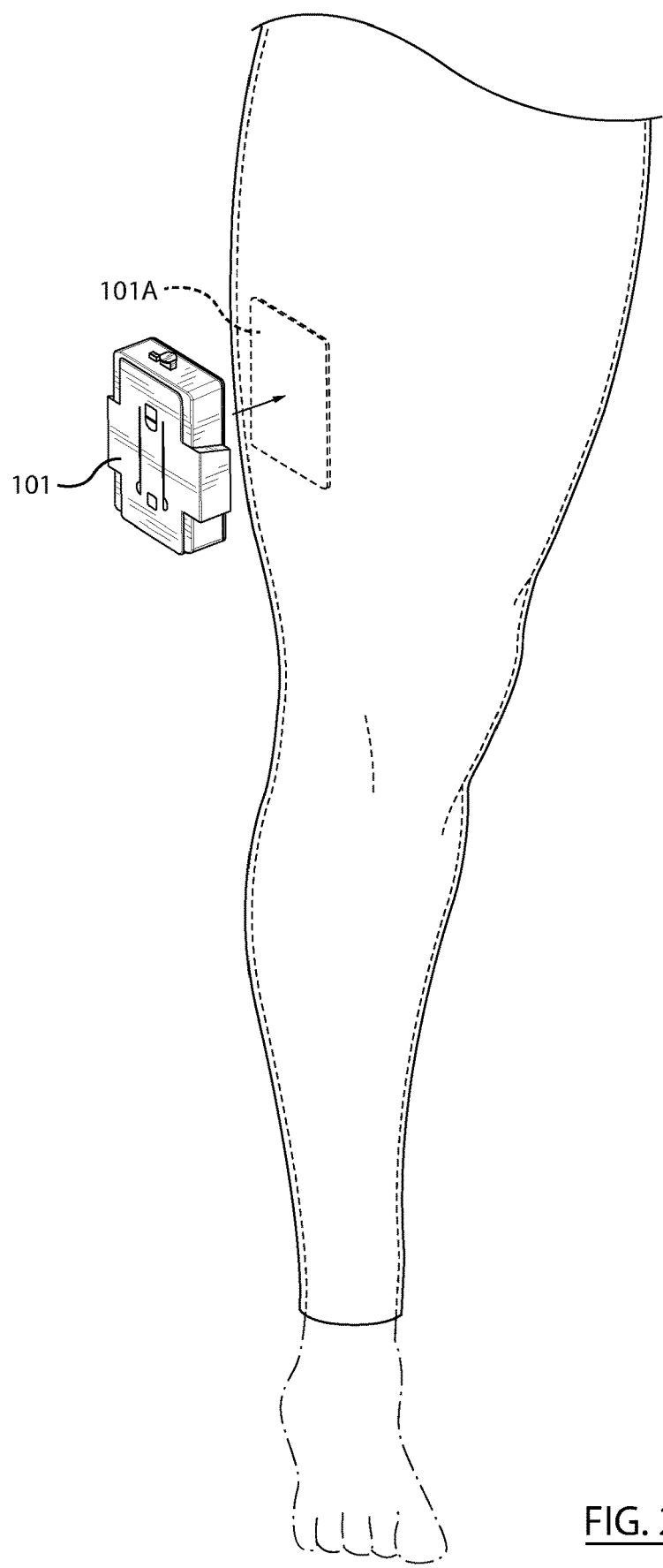
FIG. 29A shows the device of FIG. 28A being attached to a user.
Figure 29B:
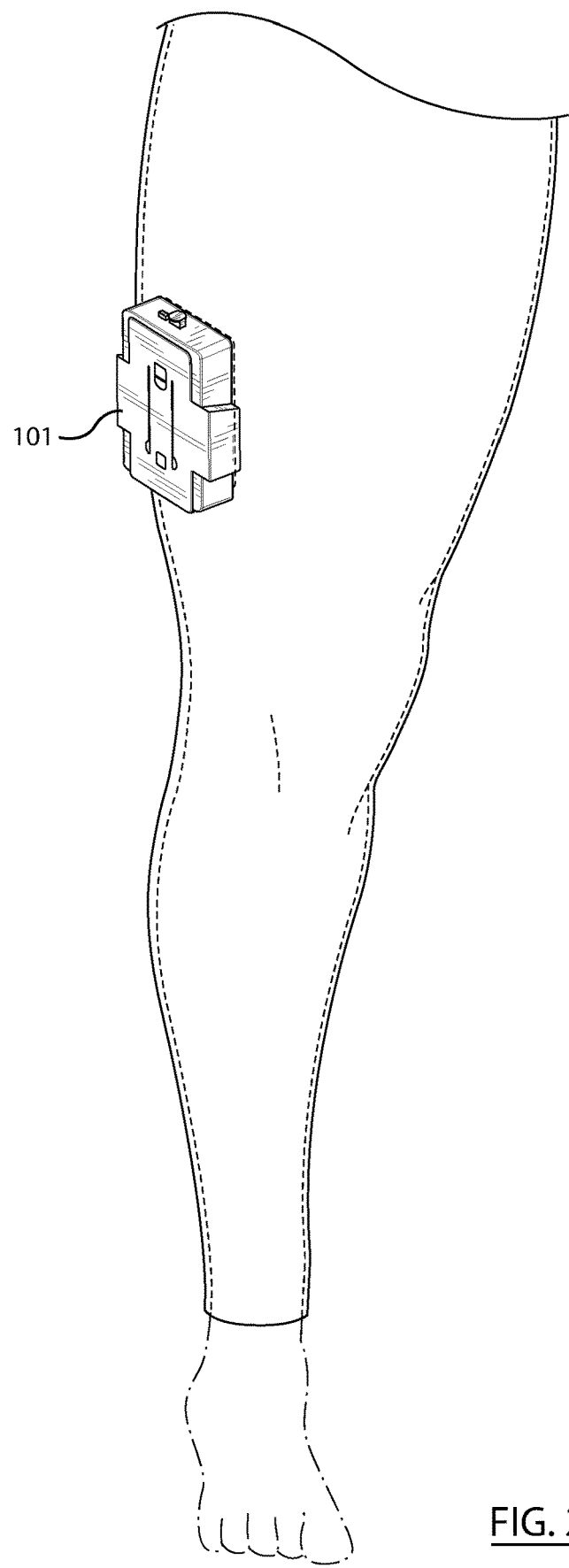
FIG. 29B shows the device of FIG. 28A attached to a user.

FIG. 29A shows the embodiments in which the auto-injecting device 101 and the component 101A are magnetically attracted to each other. In use, the component 101A is disposed under the clothing of the user. In some embodiments, the clothing is suitably tight such that the component 101A does not fall off after the disposition. For example, the clothing may be legging or yoga pants. The auto-injecting device 101 is then moved toward the component 101A. When the auto-injecting device 101 is sufficiently close to the component 101A, the auto-injecting device 101 magnetically attaches to the component 101A such that the auto-injecting device 101 is attached to the clothing of the user. In some embodiments, the clothing is suitably tight and resilient such that the automatic injection can be effected.

Figure 30A:
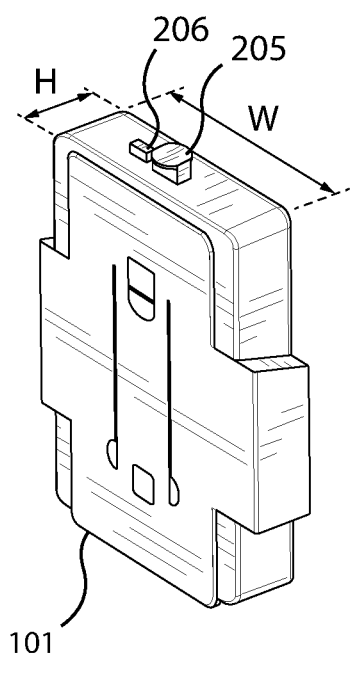
FIGS. 30A and 30B show the auto-injecting device of different sizes.
Figure 30B:
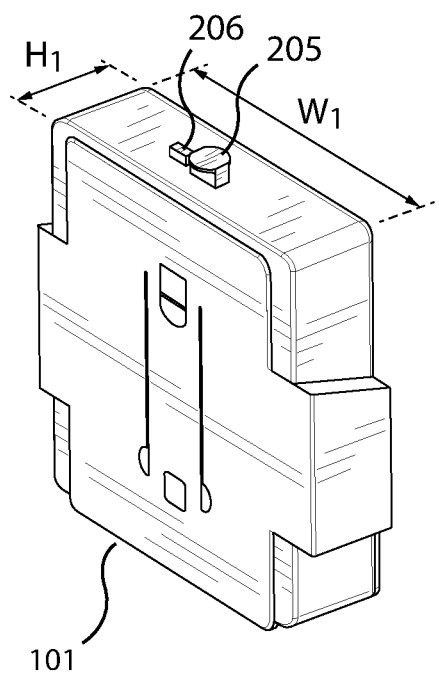

As shown in FIGS. 30A and 30B, the auto-injecting device can be of different sizes.

Although the auto-injecting device 101 shown in FIGS. 28A, 28B, 28C, 28D, 29A, 29B, 30A, and 30B is similar to that shown in FIG. 7C, it is understood that the auto-injecting device 101 can be configured as described above in any of the embodiments.

The embodiments of the present disclosure described above are intended to be examples only. The present disclosure may be embodied in other specific forms. Alterations, modifications and variations to the disclosure may be made without departing from the intended scope of the present disclosure. While the system, devices and processes disclosed and shown herein may comprise a specific number of elements/components, the systems, devices and assemblies could be modified to include addition or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and sub-ranges within disclosed ranges are also disclosed. The subject matter described herein intends to cover and embrace all suitable changes in technology. All references mentioned are hereby incorporated by reference in their entirety.

In example embodiments, as appropriate, each illustrated block or module may represent software, hardware, or a combination of hardware and software. Further, some of the blocks or modules may be combined in other example embodiments, and more or less blocks or modules may be present in other example embodiments. Furthermore, some of the blocks or modules may be separated into a number of sub-blocks or sub-modules in other embodiments.

While some of the present embodiments are described in terms of methods, a person of ordinary skill in the art will understand that present embodiments are also directed to various apparatus such as a server apparatus including components for performing at least some of the aspects and features of the described methods, be it by way of hardware components, software or any combination of the two, or in any other manner. Moreover, an article of manufacture for use with the apparatus, such as a pre-recorded storage device or other similar non-transitory computer readable medium including program instructions recorded thereon, or a computer data signal carrying computer readable program instructions may direct an apparatus to facilitate the practice of the described methods. It is understood that such apparatus, articles of manufacture, and computer data signals also come within the scope of the present example embodiments.

While some of the above examples have been described as occurring in a particular order, it will be appreciated to persons skilled in the art that some of the messages or steps or processes may be performed in a different order provided that the result of the changed order of any given step will not prevent or impair the occurrence of subsequent steps. Furthermore, some of the messages or steps described above may be removed or combined in other embodiments, and some of the messages or steps described above may be separated into a number of sub-messages or sub-steps in other embodiments. Even further, some or all of the steps of the conversations may be repeated, as necessary. Elements described as methods or steps similarly apply to systems or subcomponents, and vice-versa.

In example embodiments, there may be more than one controller present. The one or more controllers can be implemented by or executed by, for example, one or more of the following systems: Programmable Logic Controller (PLC), microprocessor, mobile phone or mobile communication device.

The term "computer readable medium" as used herein includes any medium which can store instructions, program steps, or the like, for use by or execution by a computer or other computing device including, but not limited to: magnetic media, such as a diskette, a disk drive, a magnetic drum, a magneto-optical disk, a magnetic tape, a magnetic core memory, or the like; electronic storage, such as a random access memory (RAM) of any type including static RAM, dynamic RAM, synchronous dynamic RAM (SDRAM), a read-only memory (ROM), a programmable-read-only memory of any type including PROM, EPROM, EEPROM, FLASH, EAROM, a so-called "solid state disk", other electronic storage of any type including a charge-coupled device (CCD), or magnetic bubble memory, a portable electronic data-carrying card of any type including COMPACT FLASH, SECURE DIGITAL (SD-CARD), MEMORY STICK, and the like; and optical media such as a Compact Disc (CD), Digital Versatile Disc (DVD) or BLU-RAY® Disc.

Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art having the benefit of the present disclosure, such variations being within the intended scope of the present disclosure. In particular, features from one or more of the above-described embodiments may be selected to create alternative embodiments comprised of a sub-combination of features which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive.

The invention claimed is:

1. A system for injecting a substance, the system comprising:
    an injecting device, comprising:
        an injecting cartridge comprising: a syringe having a needle and a plunger, and an injecting mechanism for moving the syringe and pushing the plunger of the syringe;
        a biasing mechanism for pivoting the injecting cartridge from a storage position into an injecting position;
        a latch movable from a holding position for holding the biasing mechanism and the injecting cartridge in the storage position to a release position for releasing the biasing mechanism;
        a first actuator;
        a shaft extending from the first actuator and connected to the syringe;
        a second actuator; and
        an arm extending from the second actuator, the second actuator being fixedly connected to the syringe, and the arm being disposed adjacent a top of the plunger of the syringe;
        wherein the first actuator is configured to, in response to a first control signal, cause the shaft to move such that movement of the syringe is effected, causing insertion of the needle of the syringe, and
        wherein the second actuator is configured to, in response to a second control signal, cause the arm to push on the top of the plunger of the syringe, effecting injection of the substance in the syringe.

2. The system of claim 1, wherein the biasing mechanism comprises a spring.

3. The system of claim 2, wherein the biasing mechanism further comprises a bar on which the injecting cartridge is disposed, the bar configured to be biased by the spring; and
wherein, in response to the moving of the latch, the spring biases the injecting cartridge into the injecting position.

4. The system of claim 2, wherein the spring defines a pivot for pivoting of the injecting cartridge.

5. The system of claim 1, further comprising one or more sensors configured to measure physical signs of a user.

6. The system of claim 5, wherein the one or more sensors comprise one or more of:
a heart rate monitor;
an infrared sensor for detecting body temperature of the user;
a blood pressure sensor; or
an oxygen sensor for detecting oxygen level in the user.

7. The system of claim 5, further comprising at least one controller configured to receive data of the physical signs from the one or more sensors.

8. The system of claim 7, wherein the at least one controller is configured to:
analyze the data of the physical signs of the user to determine that the injection of the substance in the syringe is required; and
when the at least one controller determines that the injecting of the substance is required,
activate the biasing mechanism to bias the injecting cartridge to the injecting position; and
activate the injecting mechanism to move the syringe toward the user such that insertion of the needle of the syringe is effected and to push the plunger of the syringe for the injection of the substance.

9. The system of claim 8, wherein the analyzing the data of the physical signs of the user and the determining that the injection of the substance in the syringe is required comprises:
establishing a baseline indicating a normal state of the user based on normal physical signs of the user;
comparing the data of the physical signs of the user to the baseline to obtain a difference between the data of the physical signs and the baseline; and
analyzing the difference using predetermined parameters to determine whether the injection of the substance in the syringe is required.

10. The system of claim 8, further comprising an interface wherein the at least one controller further is configured to use the interface for the user to interrupt the activation of the biasing mechanism and the injecting mechanism.

11. The system of claim 8, wherein the at least one controller is configured to implement a machine learning routine for optimizing the analyzing and the determining.

12. The system of claim 7, wherein the system further comprises a first wearable band, wherein the one or more sensors and the at least one controller are part of the first wearable band.

13. The system of claim 12, wherein the injecting device is a part of the first wearable band.

14. The system of claim 13, wherein the first wearable band comprises resilient strings and resilient crosslinks linking the resilient strings.

15. The system of claim 13, wherein the first wearable band comprises:
one or more strings; and
a string tightening component for pulling the one or more strings, causing the first wearable band to contract.

16. The system of claim 15, wherein, in response to a signal from the at least one controller, the string tightening component pulls the one or more strings such that the first wearable band is secured to the user prior to the injection of the substance.

17. The system of claim 13, wherein the first wearable band comprises:
one or more muscle wires; and
a muscle wire activating unit for causing the one or more muscle wires to contract.

18. The system of claim 17, wherein the muscle wire activating unit, in response to a signal from the at least one controller, causes the one or more muscle wires to contract, such that secure attachment of the first wearable band to the user is effected prior to the injection of the substance.

19. The system of claim 13, wherein the injecting position is perpendicular to an injection surface of the user or a radially inward position with respect to the first wearable band.

20. The system of claim 13, wherein the storage position of the injecting cartridge is parallel to an injection surface of the user or tangential to a circumference of the first wearable band.

21. The system of claim 12, further comprising a second wearable band, wherein the injecting device is a part of the second wearable band.

22. The system of claim 21, wherein the second wearable band comprises resilient strings and resilient crosslinks linking the resilient strings.

23. The system of claim 21, wherein the second wearable band comprises:
one or more strings; and
a string tightening component for pulling the one or more strings, causing the second wearable band to contract.

24. The system of claim 23, wherein, in response to a signal from the at least one controller, the string tightening component pulls the one or more strings such that the second wearable band is secured to the user prior to the injection of the substance.

25. The system of claim 21, wherein the second wearable band comprises:
one or more muscle wires; and
a muscle wire activating unit for causing the one or more muscle wires to contract.

26. The system of claim 25, wherein the muscle wire activating unit, in response to a signal from the at least one controller, causes the one or more muscle wires to contract, such that secure attachment of the second wearable band to the user is effected prior to the injection of the substance.

27. The system of claim 12, wherein the system further comprises a sheet, wherein one of the sheet or the injecting device includes magnetic material, wherein the other of the injecting device or the sheet includes magnetic material or ferromagnetic material, and wherein the injecting device and the sheet magnetically attract each other for attachment to clothing between the injecting device and the sheet.

28. The system of claim 12, wherein the first wearable band further comprises a wireless communication component for communicating, with a communication device or a recipient, a status of the user.

29. The system of claim 28, wherein the first wearable band further comprises a Global Positioning Sensor (GPS) device for the wireless communication component to provide a location of the user to the communication device or the recipient.

30. The system of claim 28, wherein the system further comprises an application on a smartphone or a dedicated device that is configured to communicate with the first wearable band.

31. The system of claim 12, wherein the first wearable band further comprises an audible alarm component for outputting an audible alert when the at least one controller determines that the injection of the substance in the syringe is required.

32. The system of claim 12, wherein the first wearable band further comprises a display for displaying status of the system and/or condition of the user.

33. The system of claim 7, wherein the at least one controller is configured with a checking routine for determining whether there is a false alarm.

34. The system of claim 7, wherein the at least one controller is configured to communicate with a cloud computing environment comprising an artificial intelligence component for optimizing function of the at least one controller.

35. The system of claim 1, further comprising a knob that is connected to the latch for manual release of the latch.

36. The system of claim 1, further comprising a holding mechanism for holding the injecting cartridge in the injecting position.

37. The system of claim 1, wherein the injecting mechanism further comprises:
a bar connected to the plunger of the syringe that is manually movable to push the plunger; and
a handle engageable to the syringe when the handle is moved to a predetermined position,
wherein the handle is manually movable to cause the syringe to move, causing the insertion of the needle of the syringe.

38. The system of claim 1, wherein the first actuator and the shaft are collectively a linear solenoid.

39. The system of claim 1, wherein a syringe rail is configured in the injecting cartridge, the syringe being movably attached to the syringe rail.

40. The system of claim 1, wherein the injecting cartridge comprises a window for viewing an amount of the substance in the syringe.

41. The system of claim 1, wherein the injecting cartridge is removable and replaceable.

42. The system of claim 1, wherein the injecting cartridge is removable and replaceable from the injecting device.

43. The system of claim 1, further comprising:
a wearable band comprising the injecting device for injecting the substance, the wearable band being configured to contract in circumference; and
at least one controller configured to cause the wearable band to contract prior to the injecting of the substance from the injecting device, and configured to control the injecting device to inject the substance after the contracting of the wearable band.

44. The system of claim 43, wherein the wearable band further comprises at least one string, wherein the at least one string is tightened for the contracting of the wearable band.

45. The system of claim 44, wherein the at least one string includes one or more muscle wires, wherein the wearable band further comprises a muscle wire activating unit for causing the one or more muscle wires to contract or recover; wherein the muscle wire activating unit causes the one or more muscle wires to contract for tightening of the at least one string.

46. The system of claim 44, wherein the wearable band further comprises a string tightening actuator for pulling the at least one string, wherein the string tightening actuator pulls the at least one string for the tightening of the at least one string.

47. The system of claim 43, wherein the wearable band further comprises one or more sensors configured to measure physical signs of a user; and wherein the at least one controller is configured to:
receive data of the physical signs from the one or more sensors,
analyze the data of the physical signs to determine that the injecting of the substance from the injecting device is required,
when the at least one controller determines that the injecting of the substance is required, the at least one controller causes the wearable band to perform the contracting of the wearable band and the control of the injection device to inject the substance.

48. The system of claim 43, wherein the at least one controller is configured to, prior to the injecting of the substance, cause the injecting device to pivot to a position perpendicular to an injection surface of a user or a radially inward position with respect to the wearable band.

49. A system for injecting a substance, the system comprising:
an injecting device, comprising:
an injecting cartridge comprising: a syringe having a needle and a plunger, and an injecting mechanism for moving the syringe and pushing the plunger of the syringe;
a biasing mechanism for pivoting the injecting cartridge from a storage position into an injecting position;
a latch movable from a holding position for holding the biasing mechanism and the injecting cartridge in the storage position to a release position for releasing the biasing mechanism;
a bar connected to the plunger of the syringe that is manually movable to push the plunger; and
a handle engageable to the syringe when the handle is moved to a predetermined position,
wherein the handle is manually movable to cause the syringe to move, causing insertion of the needle of the syringe.

* * * * *